United States Patent
Yang et al.

(10) Patent No.: US 11,091,421 B2
(45) Date of Patent: Aug. 17, 2021

(54) BENZENE FUSED HETEROCYCLIC DERIVATIVE AND PHARMACEUTICAL COMPOSITION COMPRISING THE SAME

(71) Applicant: TAIWANJ PHARMACEUTICALS CO., LTD., Zhubei (TW)

(72) Inventors: Syaulan S. Yang, Zhubei (TW); Kuang Yuan Lee, Hsinchu (TW); Meng Hsien Liu, Toufen (TW); Yan-Feng Jiang, Kaohsiung (TW); Yu-Shiou Fan, Taipei (TW); Chi-Han Chen, Taipei (TW); Sheng Hung Liu, Zhubei (TW)

(73) Assignee: TAIWANJ PHARMACEUTICALS CO., LTD., Zhubei (TW)

( * ) Notice: Subject to any disclaimer, the term of this patent is extended or adjusted under 35 U.S.C. 154(b) by 0 days.

(21) Appl. No.: 16/620,608

(22) PCT Filed: Sep. 7, 2018

(86) PCT No.: PCT/US2018/049946
§ 371 (c)(1),
(2) Date: Dec. 9, 2019

(87) PCT Pub. No.: WO2019/051222
PCT Pub. Date: Mar. 14, 2019

(65) Prior Publication Data
US 2020/0190010 A1    Jun. 18, 2020

Related U.S. Application Data

(60) Provisional application No. 62/555,233, filed on Sep. 7, 2017.

(51) Int. Cl.
*C07C 65/00* (2006.01)
*C07C 233/00* (2006.01)
(Continued)

(52) U.S. Cl.
CPC ............ *C07C 65/21* (2013.01); *C07C 49/755* (2013.01); *C07C 65/38* (2013.01); *C07C 69/78* (2013.01);
(Continued)

(58) Field of Classification Search
CPC ....... C07C 65/21; C07C 65/38; C07C 49/755; C07C 69/78; C07C 233/66; C07D 209/48; C07D 217/24
See application file for complete search history.

(56) References Cited

U.S. PATENT DOCUMENTS 5,612,356 A * 3/1997 Yoshimura ........... C07D 311/92
514/338

FOREIGN PATENT DOCUMENTS

WO    WO 90/12010 A1    10/1990
WO    WO 2016/124939 A1    8/2016

OTHER PUBLICATIONS

Hallgas et al., "Comparison of measured and calculated lipophilicity of substituted aurones and related compounds", Journal of Chromatography B, Elsevier, 2004, vol. 801, pp. 229-235.
Haudecoeur et al., "Discovery of Naturally Occurring Aurones That Are Potent Allosteric Inhibitors of Hepatitis C Virus RNA-Dependent RNA Polymerase", Journal of Medicinal Chemistry, 2011, vol. 54, pp. 5395-5402.
International Search Report, issued in PCT/US2018/049946, dated Dec. 12, 2018.
Muzychka et al., "Carboxylated aurone derivatives as potent inhibitors of xanthine oxidase", Bioorganic & Medicinal Chemistry, 2017, vol. 25, pp. 3606-3613.

(Continued)

*Primary Examiner* — Sikarl A Witherspoon
(74) *Attorney, Agent, or Firm* — Birch, Stewart, Kolasch & Birch, LLP

(57) ABSTRACT

The present disclosure provides a benzene fused heterocyclic derivative of Formula (I): ---- is a single or double bond; n is an integer of 0 or 1; A is —$CH_2$—, —CH(OH)—, or —C(O)—; G is C or N; X is —$CH_2$—, O, or —C(O)—; Y is alkyl, aryl, or heterocyclic alkyl optionally substituted with at least one substituent independently selected from a group consisting of: H, halogen, alkyl, alkyl substituted with at least one halogen, aryl, aryl substituted with at least one halogen, —$NR_{y1}R_{y2}$, —$OR_{y1}$, —$R_{y1}C(O)R_{y3}$, —$C(O)R_{y1}$, —$C(O)OR_{y2}$, —$C(O)OR_{y2}Ry3$, —$NR_{y1}C(O)R_{y2}$, —$NR_{y1}C(O)NR_{y2}R_{y3}$, —$NR_{y1}C(O)OR_{y2}R_{y3}$, —$NR_{y1}C(O)R_{y2}OR_{y3}$, $C(O)NR_{y1}(R_{y2}R_{y3})$, —$C(O)NR_{y1}(R_{y2}OR_{y1})$, —$OR_{y2}R_{y3}$, and —$OR_{y2}OR_{y3}$, wherein each of $R_{y1}$ and $R_{y2}$ is independently selected from a group consisting of H, oxygen, alkyl, and aryl, and $R_{y3}$ is aryl optionally substituted with at least one halogen; Z is —$NR_{z1}R_{z2}$, —$NR_{z1}R_{z3}$, —$OR_{z1}$, —$OR_{z1}R_{z3}$, —$C(O)R_{z1}R_{z3}$, —$C(O)OR_{z1}R_{z3}$, —$NR_{z1}C(O)R_{z2}R_{z3}$, —$NR_{z1}C(O)OR_{z2}R_{z3}$, —$C(O)NR_{z1}R_{z3}$, or $OR_{z2}OR_{z3}$, wherein each of $R_{z1}$ and $R_{z2}$ is independently selected from a group consisting of H, oxygen, alkyl and aryl, and $R_{z3}$ is aryl optionally substituted with at least one substituent independently selected from a group consisting of halogen, OH, —$R_{za}COOR_{zb}$, —$OR_{za}COOR_{zb}$, —$R_{za}SO_2R_{zb}$, —$R_{za}SO_2NR_{zb}R_{zc}R_{zd}$, —$R_{za}C(O)R_{zb}R_{zc}$, —$R_{za}C(O)NR_{zb}R_{zc}R_{zd}$, —$RZ_aC(O)NR_{zb}SO_2R_{zc}$, wherein Rza is nil or alkyl, $R_{zb}$ is H or alkyl, each of $R_{zb}$ and $R_{zc}$ is independently selected from a group consisting of H, OH, alkyl, aryl, alkoxyl, or $NR_{zb}R_{zc}$ is a nitrogen-containing heterocyclic alkyl ring, $R_{zd}$ is nil or a sulfonyl alkyl group.

(I)

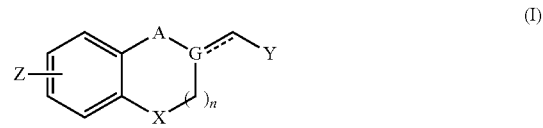

12 Claims, No Drawings

(51) Int. Cl.
| | |
|---|---|
| *C07C 49/00* | (2006.01) |
| *C07D 209/00* | (2006.01) |
| *C07D 217/00* | (2006.01) |
| *C07C 65/21* | (2006.01) |
| *C07C 49/755* | (2006.01) |
| *C07C 65/38* | (2006.01) |
| *C07C 69/78* | (2006.01) |
| *C07C 233/66* | (2006.01) |
| *C07C 233/69* | (2006.01) |
| *C07C 271/30* | (2006.01) |
| *C07C 275/38* | (2006.01) |
| *C07D 209/48* | (2006.01) |
| *C07D 211/32* | (2006.01) |
| *C07D 217/24* | (2006.01) |
| *C07D 295/182* | (2006.01) |
| *C07D 307/83* | (2006.01) |

(52) U.S. Cl.
CPC .......... *C07C 233/66* (2013.01); *C07C 233/69* (2013.01); *C07C 271/30* (2013.01); *C07C 275/38* (2013.01); *C07D 209/48* (2013.01); *C07D 211/32* (2013.01); *C07D 217/24* (2013.01); *C07D 295/182* (2013.01); *C07D 307/83* (2013.01)

(56) References Cited

OTHER PUBLICATIONS

Written Opinion of the International Searhing Authority, issued in PCT/US2018/049946, dated Dec. 12, 2018.
Zheng et al., "Synthesis and Anticanver Effect of B-Ring Trifluoromethylated Flavonoids", Bioorganic & Medicinal Chemistry Letters, 2003, vol. 13, pp. 3423-3427.

* cited by examiner

BENZENE FUSED HETEROCYCLIC DERIVATIVE AND PHARMACEUTICAL COMPOSITION COMPRISING THE SAME

CROSS REFERENCE TO RELATED APPLICATIONS

This application is the National Phase of PCT International Application No. PCT/US2018/049946, filed on Sep. 7, 2018, which claims priority under 35 U.S.C. 119(e) to U.S. Provisional Application No. 62/555,233, filed on Sep. 7, 2017, all of which are hereby expressly incorporated by reference into the present application.

TECHNICAL FIELD

The technical field relates to benzene fused heterocyclic derivatives, and in particular it relates to benzene fused heterocyclic derivatives as autotaxin inhibitors and pharmaceutical compositions comprising the same.

BACKGROUND

Autotaxin (ATX) is an enzyme that in humans is encoded by the ENPP2 gene, and is known as ectonucleotide pyrophosphatase/phosphodiesterase family member 2 (NPP2 or ENPP2) or lysophospholipase D. Autotaxin has lysophospholipase D activity that converts lysophosphatidylcholine into lysophosphatidic acid (LPA). Autotaxin is a ~120 kDa secreted enzyme that is important in generating the lipid signaling molecule LPA.

Autotaxin and LPA have been shown to be involved in many cancers. Moreover, autotaxin and LPA are also involved in numerous inflammatory-driven diseases such as asthma and arthritis.

Non-alcoholic fatty liver disease (NAFLD) is the buildup of extra fat in liver cells that is not caused by alcohol. Non-alcoholic steatohepatitis (NASH) is the most extreme form of NAFLD. Moreover, NASH is regarded as a major cause of cirrhosis of the liver of unknown cause, and ATX-LPA signaling has been implicated in hepatic fibrogenesis.

Idiopathic pulmonary fibrosis (IPF) is a chronic, relentlessly progressive fibrotic disorder of the lungs occurring mainly in older adults. It is reported that in both murine and human fibrotic lungs, increased concentrations of ATX can be detected.

Therefore, development of autotaxin inhibitors for treating diseases, such as cancer, NAFLD, IPF, etc. is needed.

SUMMARY

The present disclosure provides a benzene fused heterocyclic derivative of Formula (I):

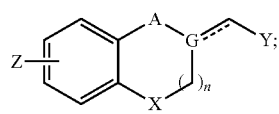

Formula (I)

------- is a single or double bond; n is an integer of 0 or 1; A is —$CH_2$—, —CH(OH)—, or —C(O)—; G is C or N; X is —$CH_2$—, O, or —C(O)—; Y is alkyl, aryl, or heterocyclic alkyl optionally substituted with at least one substituent independently selected from a group consisting of: H, halogen, alkyl, alkyl substituted with at least one halogen, aryl, aryl substituted with at least one halogen, —$NR_{y1}R_{y2}$, —$OR_{y1}$, —$R_{y1}C(O)R_{y3}$, —$C(O)R_{y1}$, —$C(O)OR_{y2}$, —$C(O)OR_{y2}R_{y3}$, —$NR_{y1}C(O)R_{y2}$, —$NR_{y1}C(O)NR_{y2}R_{y3}$, —$NR_{y1}C(O)OR_{y2}R_{y3}$, —$NR_{y1}C(O)R_{y2}OR_{y3}$, —$C(O)NR_{y1}(R_{y2}R_{y3})$, —$C(O)NR_{y1}(R_{y2}OR_{y1})$, —$OR_{y2}R_{y3}$, and —$OR_{y2}OR_{y3}$, wherein each of $R_{y1}$ and $R_{y2}$ is independently selected from a group consisting of H, oxygen, alkyl, and aryl, and $R_{y3}$ is aryl optionally substituted with at least one halogen; Z is —$NR_{z1}R_{z2}$, —$NR_{z1}R_{z3}$, —$OR_{z1}$, —$OR_{z1}R_{z3}$, —$C(O)R_{z1}R_{z3}$, —$C(O)OR_{z1}R_{z3}$, —$NR_{z1}C(O)R_{z2}R_{z3}$, —$NR_{1}C(O)OR_{z2}R_{z3}$, —$C(O)NR_{z1}R_{z3}$, or $OR_{z2}OR_{z3}$, wherein each of $R_{z1}$ and $R_{z2}$ is independently selected from a group consisting of H, oxygen, alkyl and aryl, and $R_{z3}$ is aryl optionally substituted with at least one substituent independently selected from a group consisting of halogen, OH, —$R_{za}CO-OR_{zb}$, —$OR_{za}COOR_{zb}$, —$R_{za}SO_2R_{zb}$, —$R_{za}SO_2NR_{zb}R_{zc}R_{zd}$, —$R_{za}C(O)R_{zb}R_{zc}$, —$R_{za}C(O)NR_{zb}R_{zc}R_{zd}$, —$R_{za}C(O)NR_{zb}SO_2R_{zc}$, wherein $R_{za}$ is nil or alkyl, $R_{zb}$ is H or alkyl, each of $R_{zb}$ and $R_{zc}$ is independently selected from a group consisting of H, OH, alkyl, aryl, alkoxyl, or $NR_{zb}R_{zc}$ is a nitrogen-containing heterocyclic alkyl ring, $R_{zd}$ is nil or a sulfonyl alkyl group.

The present disclosure also provides a pharmaceutical composition, comprising: a therapeutically effective amount of the benzene fused heterocyclic derivative of the present disclosure; and a pharmaceutically acceptable carrier.

The present disclosure further provides a method for inhibiting the activity of autotaxin in environment, comprising: contacting the environment with an effective amount of the benzene fused heterocyclic derivative of the present disclosure or the pharmaceutical composition of the present disclosure.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Definitions of Terms

When a range of values is listed, it is intended to encompass each value and sub-range within the range. For example, "$C_{1-4}$" is intended to encompass, $C_1$, $C_2$, $C_3$, $C_4$, $C_{1-4}$, $C_{1-3}$, $C_{1-2}$, $C_{2-4}$, $C_{2-3}$, and $C_{3-4}$.

Unless otherwise indicated, the term "alkyl" means a straight chain, branched and/or cyclic hydrocarbon having from 1 to 20 (e.g., 1 to 10, 1 to 9, 1 to 8, 1 to 7, 1 to 6, 1 to 5, 1 to 4, 1 to 3, 1 to 2, or 1) carbon atoms. Alkyl moieties having from 1 to 4 carbons ($C_{1-4}$ alkyl) are referred to as "lower alkyl." Examples of alkyl groups include methyl, ethyl, propyl, isopropyl, n-butyl, t-butyl, isobutyl, 2-isopropyl-3-methyl butyl, pentyl, pentan-2-yl, hexyl, isohexyl, heptyl, heptan-2-yl, 4,4-dimethylpentyl, octyl, 2,2,4-trimethylpentyl, nonyl, decyl, undecyl and dodecyl. Unless otherwise specified, each instance of an alkyl group is independently optionally substituted, i.e., unsubstituted (an "unsubstituted alkyl") or substituted (a "substituted alkyl")

with one or more substituents. In certain embodiments, the alkyl group is substituted $C_{2-10}$ alkyl.

"Heterocyclic alkyl" refers to a radical of a 3- to 10-membered non-aromatic ring system having ring carbon atoms and 1 to 4 ring heteroatoms, wherein each heteroatom is independently selected from nitrogen, oxygen, sulfur, phosphorus, and silicon ("3-10 membered heterocyclic alkyl"). In heterocyclyl groups that contain one or more nitrogen atoms, the point of attachment can be a carbon or nitrogen atom, as valency permits. Unless otherwise specified, each instance of heterocyclic alkyl is independently optionally substituted, i.e., unsubstituted (an "unsubstituted heterocyclic alkyl") or substituted (a "substituted heterocyclic alkyl") with one or more substituents. In some embodiments, a heterocyclyl group is a 5-8 membered non-aromatic ring system having ring carbon atoms and 1-4 ring heteroatoms, wherein each heteroatom is independently selected from nitrogen, oxygen, and sulfur. In some embodiments, a heterocyclic alkyl group is a 5-6 membered non-aromatic ring system having ring carbon atoms and 1-4 ring heteroatoms, wherein each heteroatom is independently selected from nitrogen, oxygen, and sulfur. In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclic alkyl has one ring heteroatom selected from nitrogen, oxygen, and sulfur. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl.

Unless otherwise indicated, the term "aryl" means an aromatic ring or a partially aromatic ring system composed of carbon and hydrogen atoms. An aryl moiety may comprise multiple rings bound or fused together. Examples of aryl moieties include naphthyl, and phenyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is a substituted phenyl.

Unless otherwise indicated, the term "heteroaryl" means an aryl moiety wherein at least one of its carbon atoms has been replaced with a heteroatom (e.g., N, O or S). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl.

Unless otherwise indicated, the term "alkoxy" or "alkoxyl" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl), such as —OCH$_3$ and —OCH$_2$CH$_3$.

Unless otherwise indicated, the terms "halogen" and "halo" encompass fluoro, chloro, bromo, and iodo.

The term "amino" refers to a moiety of the formula: —N(R)$_2$, wherein each instance of R is independently a substituent described herein, or two instances of R are connected to form substituted or unsubstituted heterocyclyl. In certain embodiments, the amino is unsubstituted amino (i.e., —NH$_2$). In certain embodiments, the amino is a substituted amino group, wherein at least one instance of R is not hydrogen.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, —OH, —CHO, alkoxy, alkanoyloxy (e.g., —OAc), alkenyl, alkyl (e.g., methyl, ethyl, propyl, t-butyl), aryl, aryloxy, halo, or haloalkyl (e.g., —CCl$_3$, —CF$_3$, —C(CF$_3$)$_3$).

In a particular embodiment, the term "substituted," when used to describe a chemical structure or moiety, refers to a derivative of that structure or moiety wherein one or more of its hydrogen atoms is substituted with one or more of: alkoxy, alkanoyloxy, alkyl, aryl, halo, haloalkyl, or hydroxyl.

Unless otherwise indicated, one or more adjectives immediately preceding a series of nouns is to be construed as applying to each of the nouns. For example, the phrase "optionally substituted alky, cycloalkyl, heterocyclic alkyl, aryl, or heteroaryl" has the same meaning as "optionally substituted alky, optionally substituted cycloalkyl, optionally substituted heterocyclic alkyl, optionally substituted aryl, or optionally substituted heteroaryl."

The present disclosure is not intended to be limited in any manner by the above exemplary listing of substituents.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2H$_2$O) and hexahydrates (R·6H$_2$O)).

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Unless otherwise indicated, "an effective amount" of a compound is an amount sufficient to provide a therapeutic or positive benefit in the treatment or management of a disease, environment or condition, or to delay or minimize one or more symptoms associated with the disease, environment or condition. An effective amount of a compound is an amount of therapeutic agent, alone or in combination with other therapies, which provides a therapeutic benefit in the treatment or management of the disease, environment or condition. The term "effective amount" can encompass an amount that improves overall therapy, reduces or avoids symptoms or causes of a disease, environment or condition, or enhances the therapeutic efficacy of another therapeutic agent.

Unless otherwise indicated, the terms "treat," "treating" and "treatment" contemplate an action that occurs while a subject (such as patient) is suffering from the specified disease or disorder, which reduces the severity of the disease or disorder, or one or more of its symptoms, or retards or slows the progression of the disease or disorder.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically acceptable carrier" refers to a carrier, whether diluent or excipient, that is compatible with the other ingredients of a formulation and not deleterious to the recipient thereof. A usable pharmaceutically acceptable carrier are disclosed in various references including *Handbook of Pharmaceuticals Excipients* edited by Raymond C Rowe, Paul J Sheskey, and Marian E Quinn. In a unlimited embodiment, said pharmaceutically acceptable carrier can be selected from the group consisting of inert diluents, dispersing and/or granulating agents, surface active agents and/or emulsifiers, disintegrating agents, binding agents, preservatives, buffering agents, lubricating agents, and/or oils. Said compositions optionally further comprise at least one of additional biologically active compounds or agents.

The terms "administration" or "administering" a composition are defined to include providing the compound or the pharmaceutical composition of the present disclosure to the subject in need of treatment or control. In an alternative embodiment, said administering is conducted through oral, intravenous, intramuscular, cutaneous, subcutaneous, intrathecal, transdermal, implantation, sublingual, buccal, rectal, vaginal, ocular, otic, nasal, inhalation, or nebulization route.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in the respective testing measurements. Accordingly, unless indicated to the contrary, the numerical parameters set forth in the present disclosure and attached claims are approximations that can vary as desired. At the very least, each numerical parameter should at least be constructed in light of the number of reported significant digits and by applying ordinary rounding techniques.

The singular forms "a", "and", and "the" are used herein to include plural referents unless the context clearly dictates otherwise.

Novel Compound

The present disclosure provides a benzene fused heterocyclic derivative of Formula (I):

Formula (I)

- - - - is a single or double bond; n is an integer of 0 or 1; A is —$CH_2$—, —CH(OH)—, or —C(O)—; G is C or N; X is —$CH_2$—, O, or —C(O)—; Y is alkyl, aryl, or heterocyclic alkyl optionally substituted with at least one substituent independently selected from a group consisting of: H, halogen, alkyl, alkyl substituted with at least one halogen, aryl, aryl substituted with at least one halogen, —$NR_{y1}R_{y2}$, —$OR_{y1}$, —$R_{y1}C(O)R_{y3}$, —$C(O)R_{y1}$, —$C(O)OR_{y2}$, —$C(O)OR_{y2}R_{y3}$, —$NR_{y1}C(O)R_{y2}$, —$NR_{y1}C(O)NR_{y2}R_{y3}$, —$NR_{y1}C(O)OR_{y2}R_{y3}$, —$NR_{y1}C(O)R_{y2}OR_{y3}$, —$C(O)NR_{y1}(R_{y2}R_{y3})$, —$C(O)NR_{y1}(R_{y2}OR_{y1})$, —$OR_{y2}R_{y3}$, and —$OR_{y2}OR_{y3}$, wherein each of $R_{y1}$ and $R_{y2}$ is independently selected from a group consisting of H, oxygen, alkyl, and aryl, and $R_{y3}$ is aryl optionally substituted with at least one halogen; Z is —$NR_{z1}R_{z2}$, —$NR_{z1}R_{z3}$, —$OR_{z1}$, —$OR_{z1}R_{z3}$, —$C(O)R_{z1}R_{z3}$, —$C(O)OR_{z1}R_{z3}$, —$NR_{z1}C(O)R_{z2}R_{z3}$, —$NR_{z1}C(O)OR_{z2}R_{z3}$, —$C(O)NR_{z1}R_{z3}$, or $OR_{z2}OR_{z3}$, wherein each of $R_{z1}$ and $R_{z2}$ is independently selected from a group consisting of H, oxygen, alkyl and aryl, and $R_{z3}$ is aryl optionally substituted with at least one substituent independently selected from a group consisting of halogen, OH, —$R_{za}CO-OR_{zb}$, —$OR_{za}COOR_{zb}$, —$R_{za}SO_2R_{zb}$, —$R_{za}SO_2NR_{zb}R_{zc}R_{zd}$, —$R_{za}C(O)R_{zb}R_{zc}$, —$R_{za}C(O)NR_{zb}R_{zc}R_{zd}$, —$R_{za}C(O)NR_{zb}SO_2R_{zc}$, wherein $R_{za}$ is nil or alkyl, $R_{zb}$ is H or alkyl, each of $R_{zb}$ and $R_{zc}$ is independently selected from a group consisting of H, OH, alkyl, aryl, alkoxyl, or $NR_{zb}R_{zc}$ is a nitrogen-containing heterocyclic alkyl ring, $R_{zd}$ is nil or a sulfonyl alkyl group.

The benzene fused heterocyclic derivatives in the present disclosure have the effect of inhibiting the activity of autotaxin, and can be used as autotaxin inhibitors.

The benzene fused heterocyclic derivatives in the present disclosure can be prepared by any methods known in the art. For example, the following schemes illustrate the typical synthetic routes for preparing the benzene fused heterocyclic derivatives in the present disclosure.

A. Preparation for Compounds

1. Compounds 3-21

Scheme 1

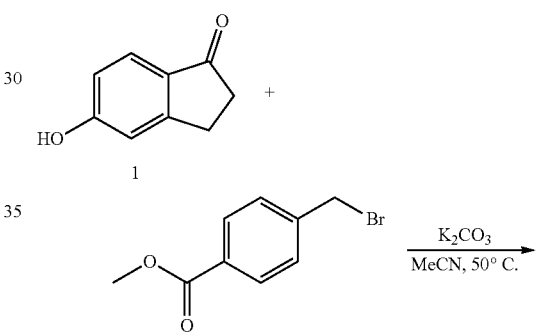

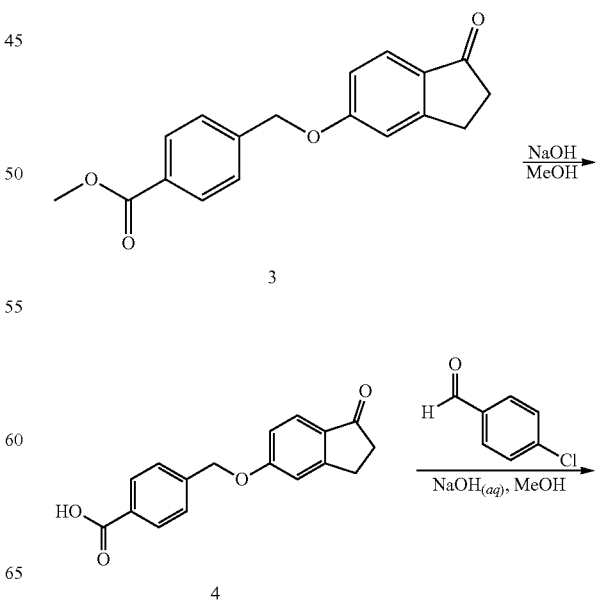

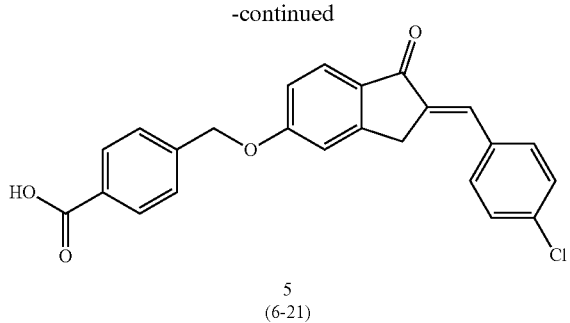

5
(6-21)

For the preparation of Compounds 3-5, please refer to Scheme 1.

A mixture solution of the 5-hydroxyindanone (1) (2.5 g, 16.9 mmol), alkyl bromide (2) (3.86 g, 16.9 mmol) and the $K_2CO_3$ (4.7 g, 33.8 mmol) in ACN (50 mL) was stirred at 50° C. for 16 hours. After cooling to room temperature, DCM (50 mL) was added to the mixture and the mixture was filtered through celite. The filtrate was concentrated and the resulting material was washed with ether to provide a product as a solid product 3. The solid product 3 was compound 3, and the yield thereof was 3.2 g (10.8 mmol).

1N NaOH solution (5 mL) was added to a solution of the Compound 3 (2.5 g, 8.4 mmol) in the co-solvent of THF:MeOH=1.1 (50 mL) at room temperature for 5 hours. The reaction mixture was concentrated to remove the organic solvent. The residue was diluted with water and acidified to pH 4 with 2N $HCl_{(aq)}$. The resulting white precipitate was filtered, washed with $H_2O$ and ether, and dried in vacuo to provide a product as a solid product 4. The solid product 4 was Compound 4, and the yield thereof was 1.4 g (5.0 mmol).

1N NaOH solution (2 mL) was added to a mixture of the Compound 4 (100 mg, 0.4 mmol) and 4-chlorobenzaldehyde (55.0 mg, 0.4 mmol) in the MeOH (2 mL) at room temperature for 16 hours. The reaction mixture was concentrated to remove the organic solvent. The residue was diluted with water and acidified to pH 4 with 2N $HCl_{(aq)}$. The resulting white precipitate was filtered, washed with $H_2O$ and ether, and dried in vacuo to provide a product as a solid product 5. The solid product 5 was Compound 5, and the yield thereof was 52.3 g (0.13 mmol). Compound 5, $^1$H-NMR (300 MHz, DMSO): δ 7.96 (d, 2H), 7.80-7.76 (m, 3H), 7.55 (d, 4H), 7.45 (s, 1H), 7.26 (s, 1H), 7.13 (d, 1H), 5.34 (s, 2H), 4.07 (s, 2H). ESI-MS m/z calcd for $C_{24}H_{17}ClO_4$ 404.08, found 405.1 $[M+H]^+$.

Compounds 6-21 were also produced according to Scheme 1 shown above.

6

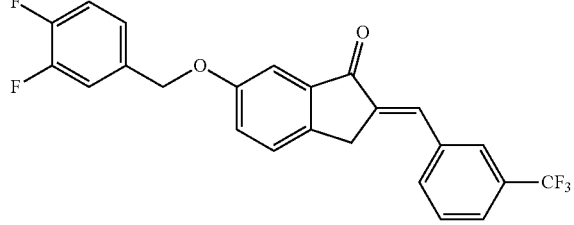

Compound 6, $^1$H-NMR (300 MHz, $CDCl_3$): δ 7.78-7.72 (m, 4H), 7.67 (s, 1H), 7.49 (d, 1H), 7.40 (s, 1H), 7.32-7.28 (m, 2H), 7.21-7.16 (m, 2H), 5.08 (s, 2H), 4.00 (s, 2H). ESI-MS m/z calcd for $C_{24}H_{15}F_5O_2$ 430.10, found 453.1 $[M+Na]^+$.

7

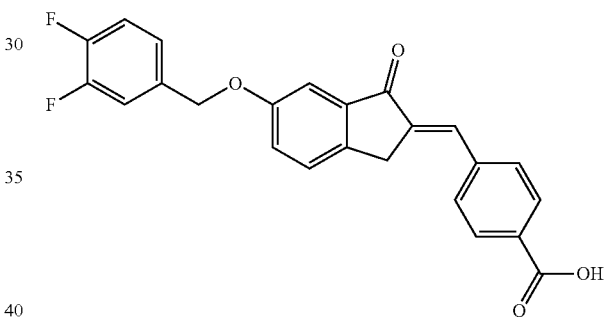

Compound 7, $^1$H-NMR (400 MHz, $CDCl_3$): δ 7.90 (s, 1H), 7.82 (d, 1H), 7.66-7.65 (m, 2H), 7.61-7.57 (m, 1H), 7.50 (d, 1H), 7.39 (s, 1H), 7.31-7.26 (m, 2H), 7.20-7.16 (m, 2H), 5.08 (s, 2H), 4.00 (s, 2H). ESI-MS m/z calcd for $C_{24}H_{15}F_5O_2$ 430.10, found 453.1 $[M+Na]^+$.

8

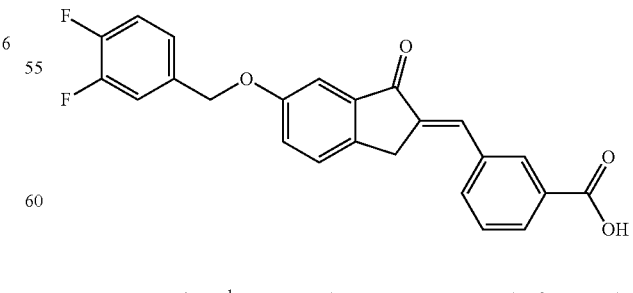

Compound 8, $^1$H-NMR (400 MHz, DMSO): δ 8.04-8.02 (d, 2H), 7.91-7.88 (d, 2H), 7.63-7.35 (m, 7H), 5.20 (s, 2H), 4.09 (s, 2H). ESI-MS m/z calcd for $C_{24}H_{16}F_2O_4$ 406.10, found 407.1 $[M+H]^+$.

9

Compound 9, $^1$H-NMR (400 MHz, DMSO): δ 8.30 (s, 1H), 8.00-7.98 (d, 2H), 7.66-7.35 (m, 8H), 5.21 (s, 2H), 4.08 (s, 2H). ESI-MS m/z calcd for $C_{24}H_{16}F_2O_4$ 406.10, found 407.1 $[M+H]^+$.

10

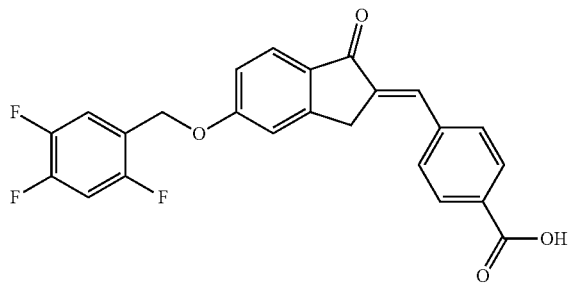

Compound 10, ¹H-NMR (400 MHz, DMSO): δ 8.02 (d, 2H), 7.87 (d, 2H), 7.77 (d, 2H), 7.66 (s, 1H), 7.51 (s, 1H), 7.32 (s, 1H), 7.15 (d, 1H), 5.25 (s, 2H), 4.14 (s, 2H). ESI-MS m/z calcd for $C_{24}H_{15}F_3O_4$ 424.09, found 425.2 $[M+H]^+$.

11

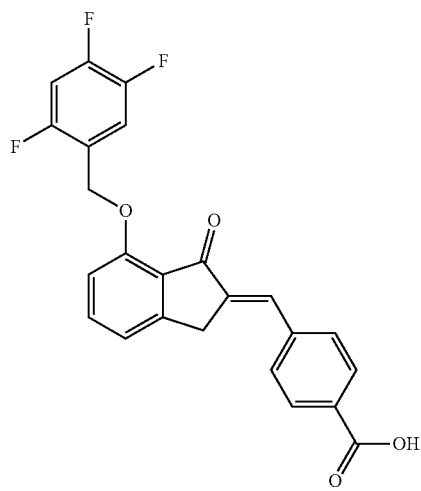

Compound 11, ¹H-NMR (300 MHz, DMSO): δ 8.03-7.84 (m, 5H), 7.67-7.65 (m, 2H), 7.48 (s, 1H), 7.24 (d, 1H), 7.16 (d, 1H), 5.28 (s, 2H), 4.13 (s, 2H). ESI-MS m/z calcd for $C_{24}H_{15}F_3O_4$ 424.09, found 425.1 $[M+H]^+$.

12

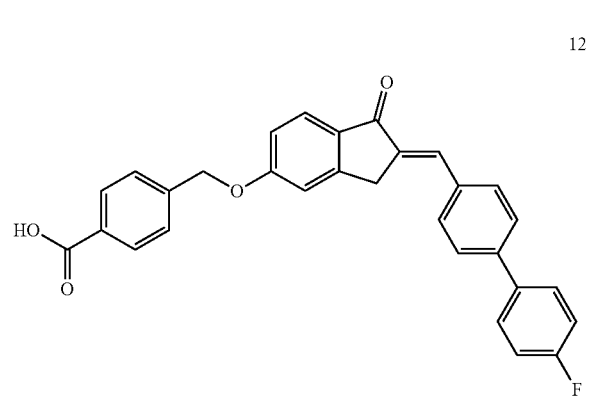 [SMILES: O=C(O)c1ccc(COc2ccc3c(c2)C/C(=C\c2ccc(-c4ccc(F)cc4)cc2)C3=O)cc1]

Compound 12, ¹H-NMR (300 MHz, DMSO): δ 8.00-7.97 (d, 2H), 7.87-7.74 (m, 8H), 7.62-7.59 (d, 2H), 7.51 (s, 1H), 7.36-7.30 (m, 3H), 7.16-7.12 (m, 1H), 5.36 (s, 2H), 4.12 (s, 2H). ESI-MS m/z calcd for $C_{30}H_{21}FO_4$ 464.14, found 465.3 $[M+H]^+$.

13

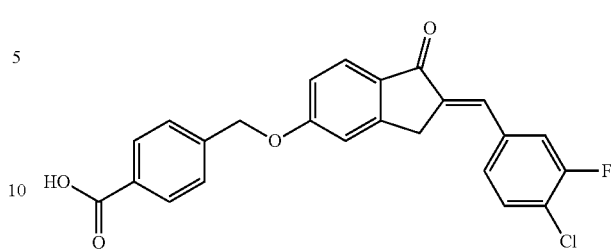

Compound 13, ¹H-NMR (300 MHz, DMSO): δ 7.98 (d, 2H), 7.83-7.69 (m, 3H), 7.64-7.58 (m, 3H), 7.44 (s, 1H), 7.26 (s, 1H), 7.13 (d, 1H), 5.36 (s, 2H), 4.09 (s, 2H). ESI-MS m/z calcd for $C_{24}H_{16}ClFO_4$ 422.07, found 423.1 $[M+H]^+$.

14

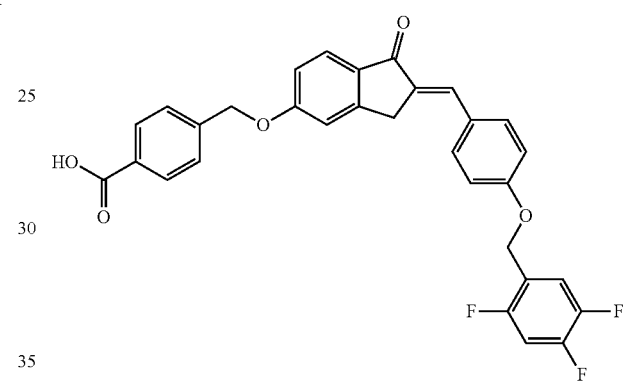

Compound 14, ¹H-NMR (400 MHz, DMSO): δ 7.86 (d, 2H), 7.80-7.70 (m, 4H), 7.69-7.62 (m, 1H), 7.43 (s, 1H), 7.35 (d, 2H), 7.26 (s, 1H), 7.17 (d, 2H), 7.10 (d, 1H), 5.24 (s, 2H), 5.18 (s, 2H), 4.04 (s, 2H). ESI-MS m/z calcd for $C_{31}H_{21}F_3NO_5$ 530.13, found 531.2 $[M+H]^+$.

15

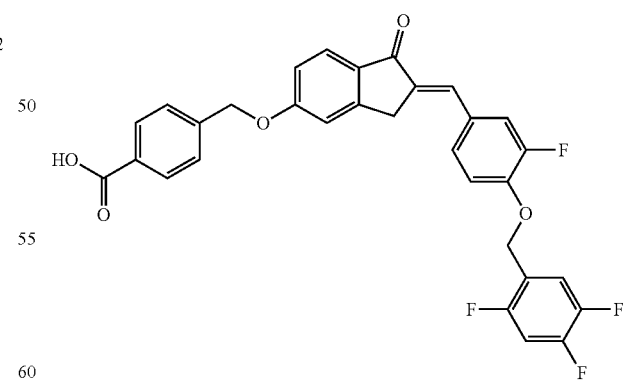

Compound 15, ¹H-NMR (300 MHz, DMSO): δ 7.98 (d, 2H), 7.79-7.69 (m, 4H), 7.64-7.57 (m, 3H), 7.45-7.41 (m, 2H), 7.26 (s, 1H), 7.12 (d, 1H), 5.35 (s, 2H), 5.25 (s, 2H), 4.05 (s, 2H). ESI-MS m/z calcd for $C_{31}H_{20}F_4O_5$ 548.12, found 549.3 $[M+H]^+$.

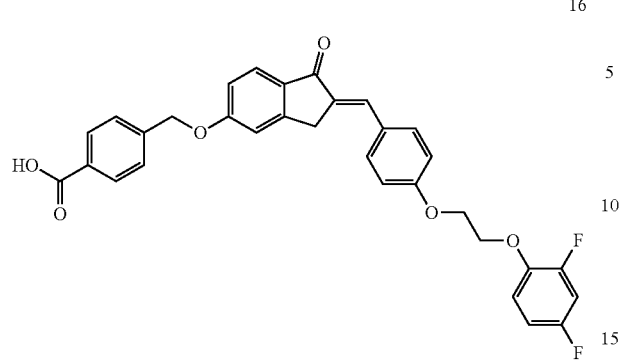

16

Compound 16, $^1$H-NMR (300 MHz, DMSO): δ 7.97 (d, 2H), 7.30 (d, 3H), 7.58 (d, 2H), 7.44 (s, 1H), 7.35-7.24 (m, 3H), 7.12 (d, 3H), 7.06-7.01 (m, 1H), 5.34 (s, 2H), 4.41 (s, 4H), 4.03 (s, 2H). ESI-MS m/z calcd for $C_{32}H_{24}F_2O_6$ 542.15, found 543.2 [M+H]$^+$.

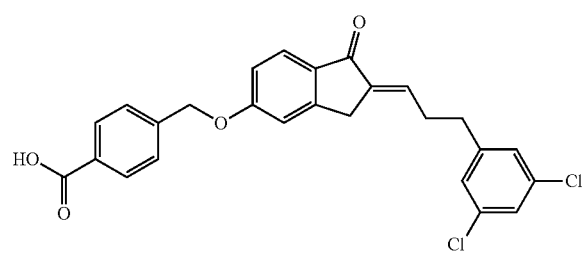

17

Compound 17, $^1$H-NMR (400 MHz, CD$_3$OD): δ 8.05 (d, 2H), 7.73 (d, 1H), 7.57 (d, 3H), 7.25 (s, 2H), 7.17 (s, 1H), 7.15-7.05 (m, 1H), 6.76-6.73 (m, 1H), 5.30 (s, 2H), 3.56 (s, 2H), 2.86 (t, 2H), 2.64 (t, 2H). ESI-MS m/z calcd for $C_{26}H_{20}Cl_2O_4$ 466.07, found 489.1 [M+Na]$^+$.

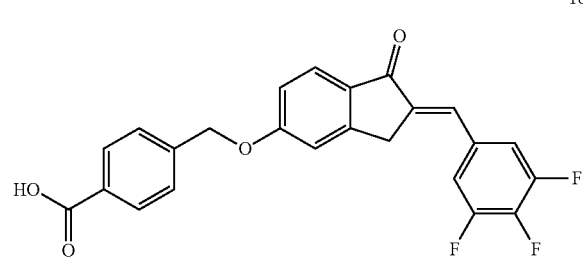

18

Compound 18, $^1$H-NMR (300 MHz, DMSO): δ 7.94 (d, 2H), 7.76-7.72 (m, 3H), 7.55 (d, 2H), 7.50 (s, 1H), 7.26 (s, 1H), 7.13 (d, 1H), 5.28 (s, 2H), 4.11 (s, 2H). ESI-MS m/z calcd for $C_{24}H_{15}F_3O_4$ 424.09, found 425.2 [M+H]$^+$.

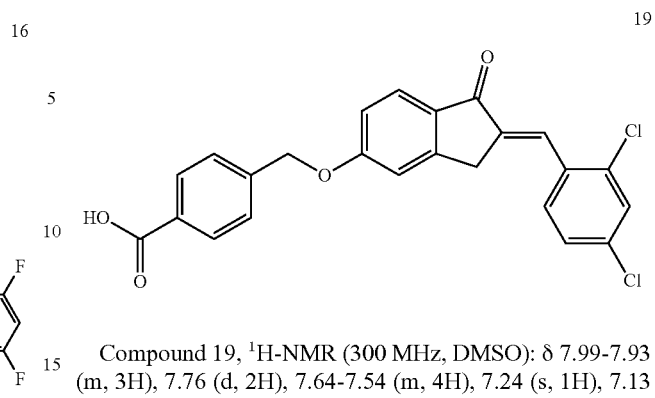

19

Compound 19, $^1$H-NMR (300 MHz, DMSO): δ 7.99-7.93 (m, 3H), 7.76 (d, 2H), 7.64-7.54 (m, 4H), 7.24 (s, 1H), 7.13 (d, 1H), 5.35 (s, 2H), 4.03 (s, 2H). ESI-MS m/z calcd for $C_{24}H_{16}Cl_2O_4$ 438.04, found 439.1 [M+H]$^+$.

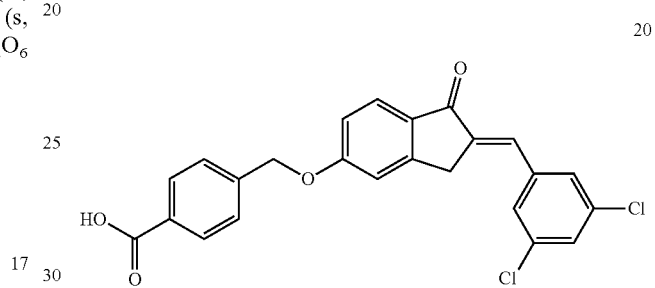

20

Compound 20, $^1$H-NMR (300 MHz, DMSO): δ 8.11 (d, 2H), 7.80 (s, 2H), 7.72 (d, 1H), 7.68 (s, 1H), 7.58 (d, 2H), 7.42 (s, 1H), 7.32 (s, 1H), 7.10 (d, 1H), 5.36 (s, 2H), 4.12 (s, 2H). ESI-MS m/z calcd for $C_{24}H_{16}Cl_2O_4$ 438.04, found 439.2 [M+H]$^+$.

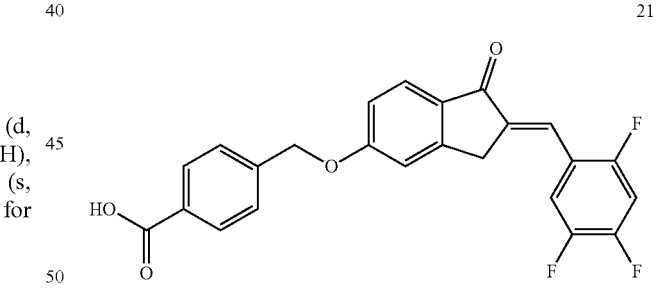

21

Compound 21, $^1$H-NMR (300 MHz, DMSO): δ 7.91-7.86 (m, 3H), 7.88-7.69 (m, 2H), 7.44 (s, 1H), 7.36 (d, 2H), 7.25 (s, 1H), 7.11 (d, 1H), 5.25 (s, 2H), 4.09 (s, 2H). ESI-MS m/z calcd for $C_{24}H_{15}F_3O_4$ 424.09, found 425.2 [M+Na]$^+$.

2. Compounds 24-28

Scheme 2

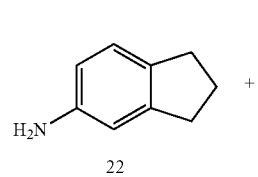

22

-continued

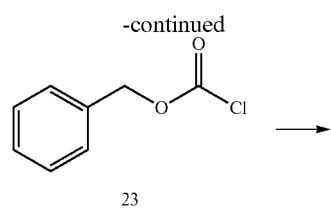

23

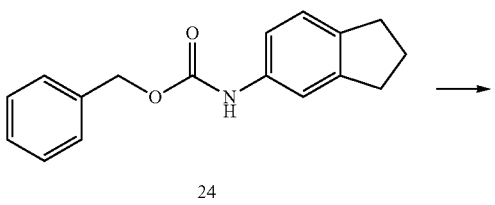

24

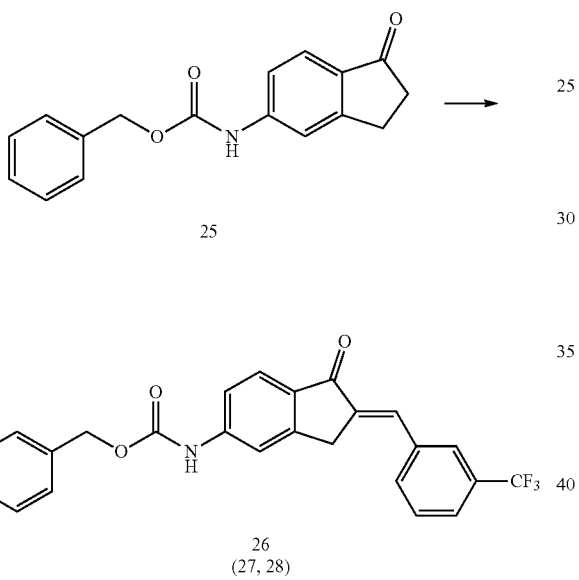

25

26
(27, 28)

For the preparation of Compounds 24-26, please refer to Scheme 2.

NaHCO₃ (2.02 g, 24.0 mmol) was added to a solution of aniline derivative (22) (2.04 g, 21.9 mmol) in 50 mL THF at 0° C., and then benzyl chloroformate (23) (3.4 mL, 24.0 mmol) was added therein. After 30 minutes, the reaction mixture was warmed to room temperature, and stirred overnight.

The reaction mixture was quenched with H₂O and extracted with 3×20 mL of EtOAc. The combined organic layers were dried over MgSO₄ and concentrated in vacuo to afford benzyl phenylcarbamate derivative (Compound 24) as a white solid that was used without further purification. The yield of Compound 24 was 4.97 g (21.9 mmol).

CrO₃ (2.57 g, 25.7 mmol) which dissolved in AcOH aqueous solution (10 mL, 50%) was slowly added to a solution of Compound 24 (2.00 g, 8.5 mmol) in AcOH (10 mL) at 0° C. The reaction mixture was warmed to room temperature, and stirred for 1 hour.

The reaction mixture was concentrated in vacuo, then basified with 1N NaOH and extracted with 3×30 mL of EtOAc. The combined organic layers were dried over MgSO₄ and concentrated in vacuo to afford 1-indanone derivative (Compound 25) as a white solid that was used without further purification. The yield of Compound 25 was 1.81 g (6.4 mmol).

1N NaOH (0.5 mL) was added to a mixture of Compound 25 (50 mg, 0.178 mmol) and 3-(trifluoromethyl)-benzaldehyde (33 mg, 0.190 mmol) in MeOH (5 mL). The reaction mixture was stirred at room temperature overnight. The reaction mixture was diluted with cold water. The precipitate solid was collected by filtration and washed with MeOH. The resulting product was Compound 26, and the yield thereof was 56 mg (0.128 mmol). Compound 26, $^1$H-NMR (400 MHz, CDCl₃): δ 7.89-7.80 (m, 4H), 7.66-7.56 (m, 3H), 7.44-7.36 (m, 4H), 7.26-7.23 (m, 1H), 6.99 (s, 1H), 5.25 (s, 2H), 4.03 (s, 2H). ESI-MS m/z calcd for $C_{25}H_{18}F_3NO_3$ 437.12, found 438.2 [M+H]⁺.

Compounds 27 and 28 were also produced according to Scheme 2 shown above.

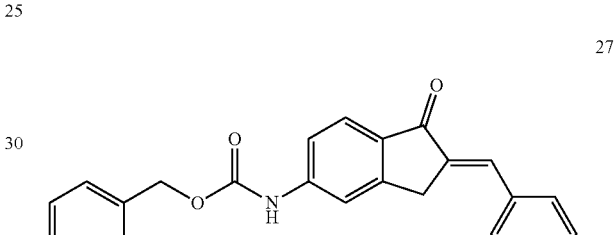

27

Compound 27, $^1$H-NMR (400 MHz, CDCl₃): δ 7.87-7.85 (m, 1H), 7.72-7.70 (m, 4H), 7.58 (s, 1H), 7.40-7.37 (m, 4H), 7.27-7.22 (m, 3H), 7.01 (s, 1H), 5.24 (s, 2H), 4.03 (s, 2H). ESI-MS m/z calcd for $C_{25}H_{18}F_3NO_5$ 437.12, found 438.2 [M+H]⁺.

28

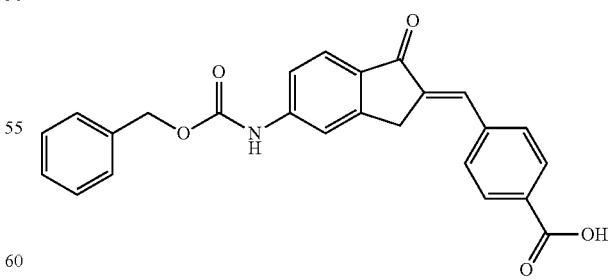

Compound 28, $^1$H-NMR (400 MHz, DMSO): δ 10.39 (s, 1H), 8.03-8.01 (d, 2H), 7.90-7.88 (d, 2H), 7.85 (s, 1H), 7.75-7.73 (d, 1H), 7.55-7.36 (m, 7H), 5.21 (s, 2H), 4.13 (s, 2H). ESI-MS m/z calcd for $C_{25}H_{19}NO_5$ 413.13, found 414.2 [M+H]⁺.

3. Compounds 30-37

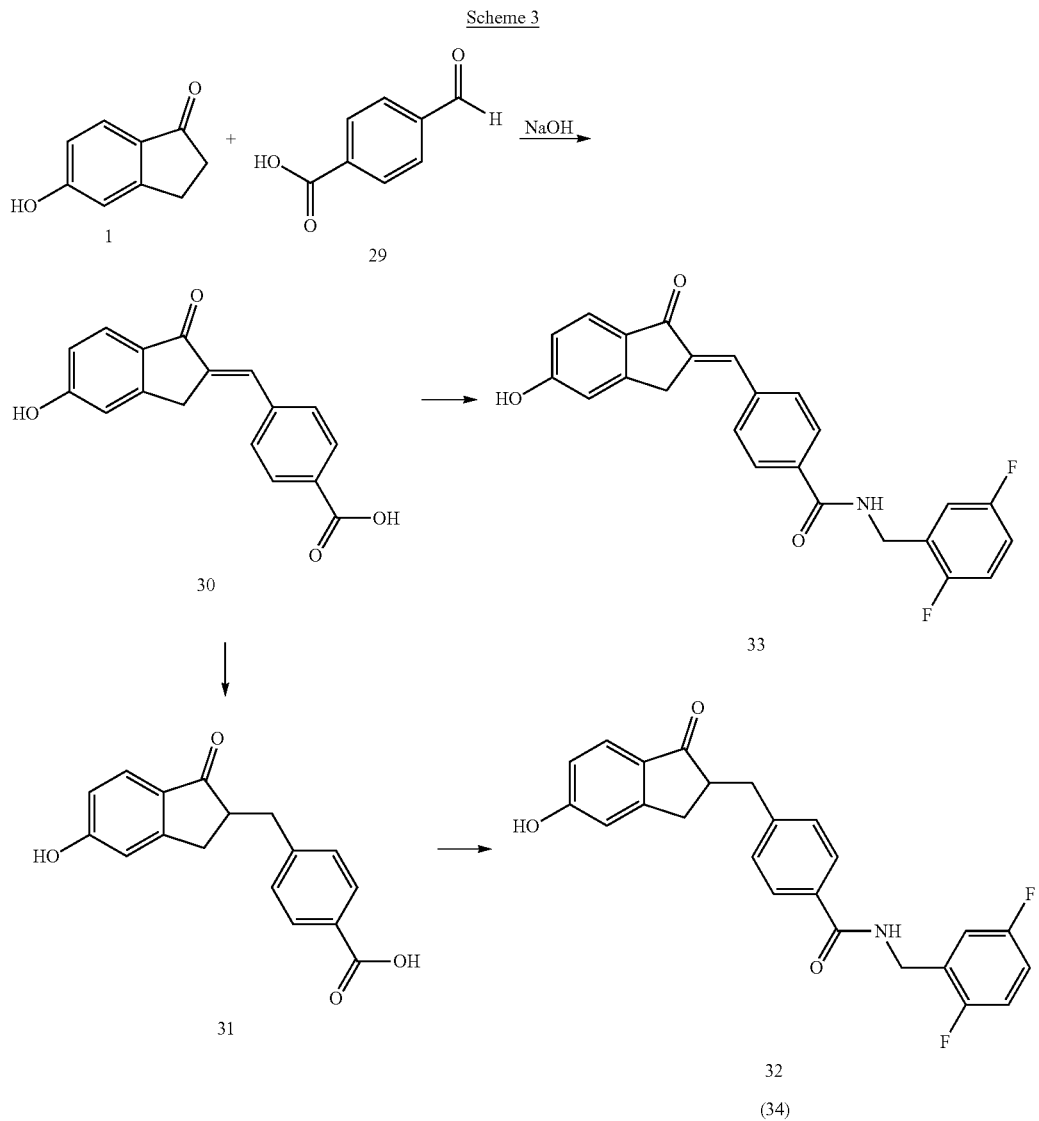

Scheme 3

For the preparation of Compounds 30-33, please refer to Scheme 3.

1N NaOH was added to a solution of 5-hydroxyindanone (1) and aldehyde (29) in MeOH. The solution was stirred at room temperature overnight. The reaction mixture was neutralized with 1N HCl, and the precipitate was collected and washed with MeOH. The solid (30) which was used without further purification.

A MeOH (100 mL) solution of benzoic acid (500 mg, 1.78 mmol) and Pd—C (100 mg) was stirred at room temperature for 3 hours under hydrogen atmosphere. Then the mixture was filtered and the filtrate was evaporated to afford a solid (Compound 31) which was used without further purification. The yield of Compound 31 was 465 mg (1.65 mmol).

TEA (0.1 mL, 0.71 mmol) and EDCI (102 mg, 0.53 mmol) were added to a mixture of Compound 31 (100 mg, 0.35 mmol), (2,5-difluorophenyl)-methanamine (76 mg, 0.53 mmol) and HOBt (24 mg, 0.18 mmol) in DCM/DMF (6 mL, 5:1) at 0° C. After the addition, the reaction mixture was slowly warmed to room temperature and stirred overnight.

The solvent was evaporated under reduced pressure. The crude residue was dissolved in EtOAc and sequentially washed with saturated NH$_4$Cl, saturated NaHCO$_3$ and brine. The combined organic layers were dried over MgSO$_4$ and concentrated under reduced pressure. The crude was purified on a silica gel column using 1:2 hexane-EtOAc as the eluant. The resulting product was Compound 32, and the yield thereof was 51 mg (0.125 mmol). Compound 32, $^1$H-NMR (300 MHz, DMSO): δ 9.00 (s, 1H), 7.83-7.80 (d, 2H), 7.52-7.49 (d, 1H), 7.39-7.36 (d, 2H), 7.29-7.08 (m, 3H), 6.80 (s, 1H), 6.77 (s, 1H), 4.49-4.47 (d, 2H), 3.22-3.16 (dd, 1H), 3.05-2.89 (m, 2H), 2.73-2.65 (m, 2H). ESI-MS m/z calcd for C$_{24}$H$_{19}$F$_2$NO$_3$ 407.13, found 430.2 [M+Na]$^+$.

TEA (0.1 mL, 0.71 mmol) and EDCI (102 mg, 0.53 mmol) were added to a mixture of Compound 30 (100 mg, 0.35 mmol), (2,5-difluorophenyl)-methanamine (76 mg, 0.53 mmol) and HOBt (24 mg, 0.18 mmol) in DMF (3 mL) at 0° C. After the addition, the reaction mixture was slowly warmed to room temperature and stirred overnight. The reaction mixture was diluted with saturated NH$_4$Cl. The precipitate thus formed was collected, and washed with ether and methanol. The resulting product was Compound 33, and the yield thereof was 40 mg (0.099 mmol). Compound 33, $^1$H-NMR (400 MHz, DMSO): δ 9.20-9.17 (m, 2H), 8.00-7.98 (d, 2H), 7.95 (s, 1H), 7.86-7.84 (d, 2H), 7.66-7.64 (d, 1H), 7.45 (s, 1H), 7.29-7.08 (m, 3H), 6.96 (s, 1H), 6.69-6.65 (d, 1H), 4.51 (s, 2H), 4.06 (s, 1H). ESI-MS m/z calcd for C$_{24}$H$_{17}$F$_2$NO$_3$ 405.12, found 406.2 [M+H]$^+$.

Compound 34 were also produced according to Scheme 3 shown above.

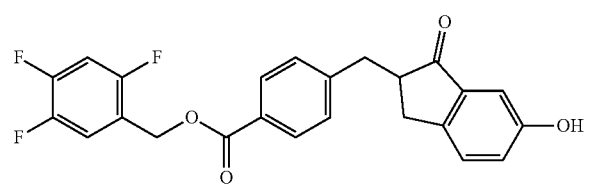

34

Compound 34, $^1$H-NMR (400 MHz, CDCl$_3$): δ 7.92 (d, 2H), 7.33-7.25 (m, 3H), 6.98-6.92 (m, 2H), 6.73 (s, 1H), 6.63 (d, 1H), 6.44 (s, 1H), 5.30 (s, 2H), 4.64 (s, 1H), 3.13-2.84 (m, 4H). ESI-MS m/z calcd for C$_{24}$H$_{17}$F$_3$O$_4$ 426.11, found 427.1 [M+H]$^+$.

4. Compounds 37-38

Scheme 4

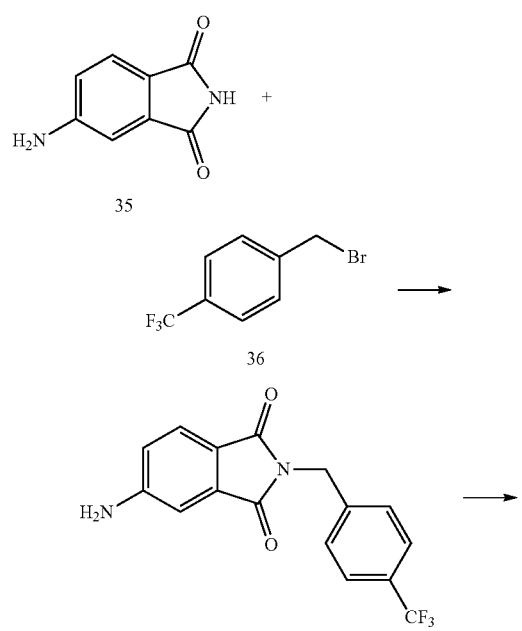

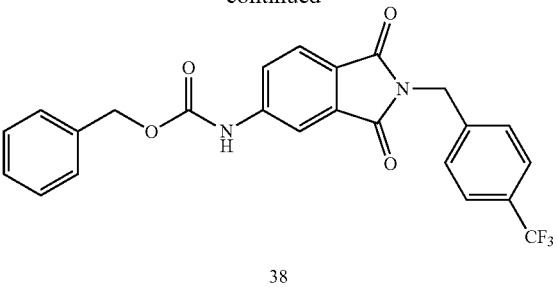

38

For the preparation of Compounds 37-38, please refer to Scheme 4.

Potassium hydroxide (0.415 g, 7.4 mmol) was added to a solution of 4-aminophthalimide (35) (1.00 g, 6.17 mmol) in dimethylformamide (50 ml) and the mixture was stirred at ambient temperature. After 2 hours, 4-trifluoromethylbenzylbromide (36) (1.9 mL, 12.34 mmol) was further added to the mixture and the mixture was stirred for another 18 hours. Water (100 ml) and ethyl acetate (100 ml) was added and the resulting phases separated. The organic phase was washed with brine, dried over sodium sulfate and concentrated in vacuum. Purification by chromatography on silica gel (Gradient: 0-50% ethyl acetate in cyclohexane) afforded Compound 37 as a yellow solid (0.750 g, 38% yield): Rf=0.2 (hexane/ethyl acetate 2:1 v/v). The Compound 37 (0.20 g, 0.62 mmol.) was dissolved in dichloromethane (5 ml) and purged with argon. Benzyl chloroformate (0.1 mL, 0.74 mmol) and triethylamine (0.60 mmol) were added to the amine solution and the resulting mixture was stirred for 2 hours at ambient temperature. After removal of the dichloromethane in vacuum, ethyl acetate (20 ml) and 10% citric acid (20 ml) were added thereto and the resulting phases were separated. The organic phase was washed with 10% sodium bicarbonate (20 ml) and brine (20 ml), dried over sodium sulfate and concentrated in vacuum. The residue was purified by chromatography on silica gel, and the resulting product was Compound 38. Compound 38, $^1$H-NMR (400 MHz, CDCl$_3$): δ 7.93 (s, 1H), 7.75 (dd, 2H), 7.55 (dd, 4H), 7.41-7.38 (m, 5H), 7.03 (s, 1H), 5.24 (s, 2H), 4.87 (s, 2H). ESI-MS m/z calcd for C$_{24}$H$_{17}$F$_3$N$_2$O$_4$ 454.11, found 477.1 [M+Na]$^+$.

5. Compounds 41-45

Scheme 5

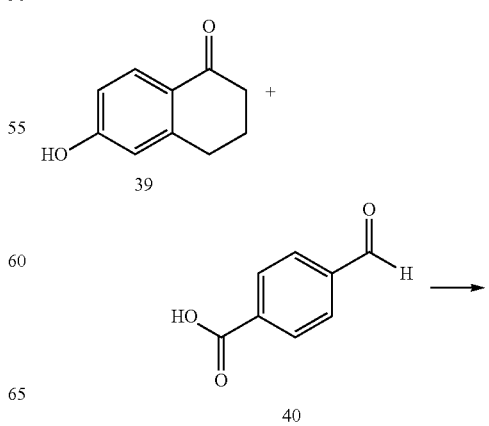

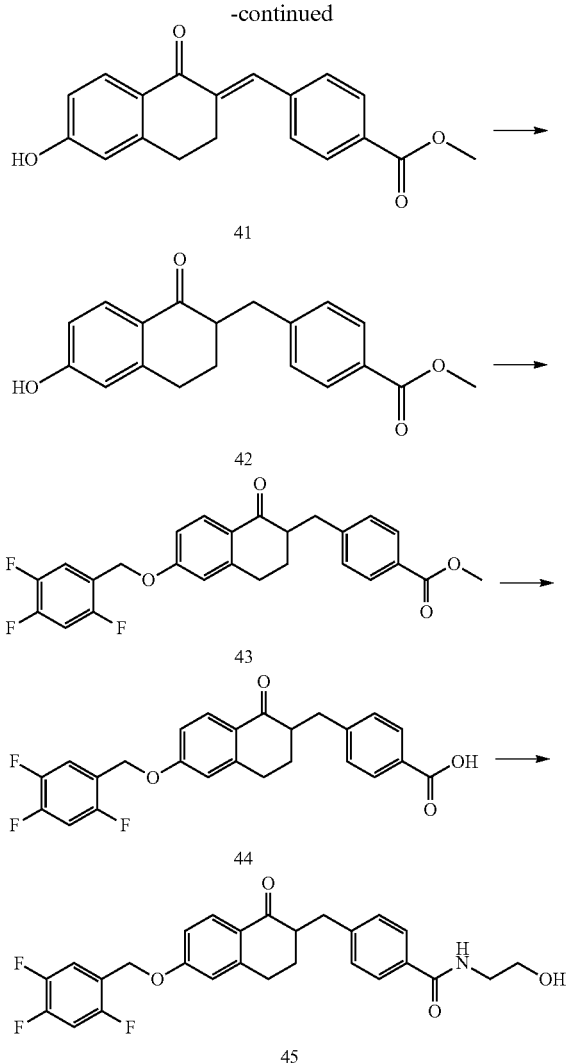

For the preparation of Compounds 41-45, please refer to Scheme 5.

A mixture of 6-hydroxy-1-tetralone (39) (1.0 g, 6.16 mmol), 4-carboxylbenzaldehyde (1.0 g, 6.66 mmol) and concentrated HCl (50.0 mL) in methanol (75.0 mL) was heated at reflux for 18 hours. The mixture was allowed to cool to room temperature and then filtered. The residue was washed with a small amount of methanol and dried in vacuo to give Compound 41 (1.40 g, 74%) as a pale brown solid.

A mixture of Compound 41 (1.40 g, 4.54 mmol) and 10% palladium on charcoal (0.15 g) in methanol (200 mL) was stirred in an atmosphere of hydrogen at room temperature for 18 hours. Palladium was removed by filtration through a bed of Celite, and the filtrate was concentrated in vacuo. Purification by column chromatography (Hexane/EA=2:1) gave an off-white fluffy solid, Compound 42 (1.35 g, 96%).

Potassium carbonate (0.30 g, 2.2 mmol) was added to a solution of compound 42 (1.0 mmol) and 2,4,5-trifluorobenzyl bromide (0.27 g, 1.2 mmol) in acetonitrile (15 mL), and the mixture was stirred overnight at 20° C. The reaction mixture was concentrated under reduced pressure and diluted with water, and the organic material was extracted with ethyl acetate (2×20 mL). The organic layers were washed with water (2×20 mL) and brine (20 mL), dried over anhydrous MgSO₄, and filtered, and the solvent was removed under reduced pressure. The product was purified by column chromatography (ethyl acetate/hexane, 1:4) to give Compound 43, and the yield thereof was 80%.

Aqueous sodium hydroxide (1 N, 1.0 mL, 1.0 mmol) was added to a solution of Compound 43 (200 mg, 0.44 mmol) in THF (5.0 mL) to form a mixture and stirred at room temperature. After 24 hours, the reaction mixture was evaporated under a reduced pressure. The residue was diluted with water (5.0 mL), acidified with 1 N aqueous HCl (2.0 mL) and to afford white solid, Compound 44, 150 mg (77%). Compound 44, $^1$H-NMR (300 MHz, DMSO): δ 7.87 (d, 1H), 7.75 (d, 3H), 7.69-7.60 (m, 1H), 7.10 (d, 2H), 7.01-6.98 (m, 2H), 5.17 (s, 2H), 3.27 (dd, 1H), 2.90 (s, 2H), 2.81-2.73 (m, 1H), 2.57 (dd, 1H), 1.97-1.91 (m, 1H), 1.68-1.60 (m, 1H). ESI-MS m/z calcd for $C_{25}H_{19}F_3O_4$ 440.12, found 441.1 [M+H]⁺.

A mixture of carboxylic acid (44) (50.0 mg), EDCI (39.1 mg), HOBt (31.1 mg) and NMM (25.0 μl) in dichloromethane (10 mL) was magnetically stirred at 25° C. under an atmosphere of nitrogen. After the mixture was stirred at 25° C. for 10 minutes, 2-aminoethan-1-ol (7.6 μl) was added to the mixture in one portion. The reaction mixture was stirred for another 16 hours. The resulting mixture was extracted with $NH_4Cl_{(aq)}$ and dichloromethane (3×50 mL). The combined extracts were dried over MgSO₄, filtered, and concentrated. The residue thus obtained was purified by washing with ether to give Compound 45 (12.3 mg, 22% yield) as a solid. Compound 45, $^1$H-NMR (300 MHz, DMSO): δ 8.36 (t, 1H), 7.87 (d, 1H), 7.79-7.60 (m, 4H), 7.32 (d, 2H), 7.02-6.98 (m, 2H), 5.17 (s, 2H), 4.71 (t, 1H), 3.49 (q, 2H), 3.27-3.20 (m, 2H), 2.92-2.89 (m, 2H), 2.86-2.80 (m, 1H), 2.73-2.49 (m, 1H), 1.96-1.90 (m, 1H), 1.70-1.62 (m, 1H). ESI-MS m/z calcd for $C_{27}H_{24}F_3NO_4$ 483.17, found 506.2 [M+Na]⁺.

Compounds 46 and 47 were also produced with the similar method according to Scheme 5 shown above.

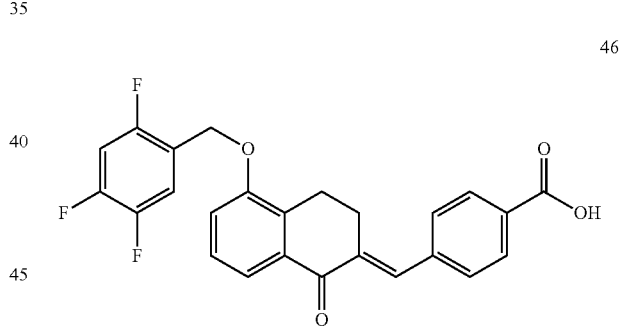

Compound 46, $^1$H-NMR (400 MHz, DMSO): δ 8.01-7.99 (d, 2H), 7.77-7.62 (m, 6H), 7.42 (s, 1H), 7.41-7.40 (d, 1H), 5.19 (s, 2H), 3.08-3.05 (t, 2H), 2.92-2.89 (t, 2H). ESI-MS m/z calcd for $C_{25}H_{17}F_3O_4$ 438.11, found 439.2 [M+H]⁺.

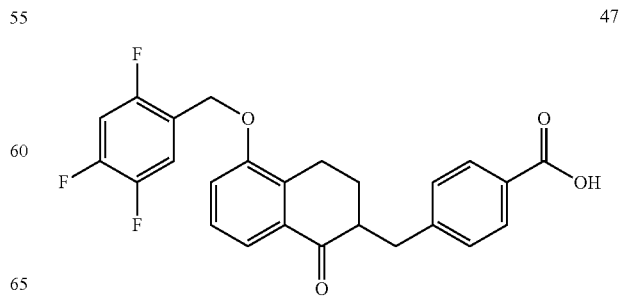

Compound 47, $^1$H-NMR (400 MHz, CDCl$_3$): δ 8.04-8.02 (d, 2H), 7.73-7.72 (d, 1H), 7.40-7.38 (d, 2H), 7.35-7.28 (m, 2H), 7.08-7.06 (d, 1H), 7.01-6.95 (m, 1H), 5.06 (s, 2H), 3.53-4.49 (dd, 1H), 3.16-3.10 (dt, 1H), 2.83-2.69 (m, 3H), 2.18-2.12 (m, 2H). ESI-MS m/z calcd for C$_{25}$H$_{19}$F$_3$O$_4$ 440.12, found 463.2 [M+Na]$^+$.

6. Compounds 49-53

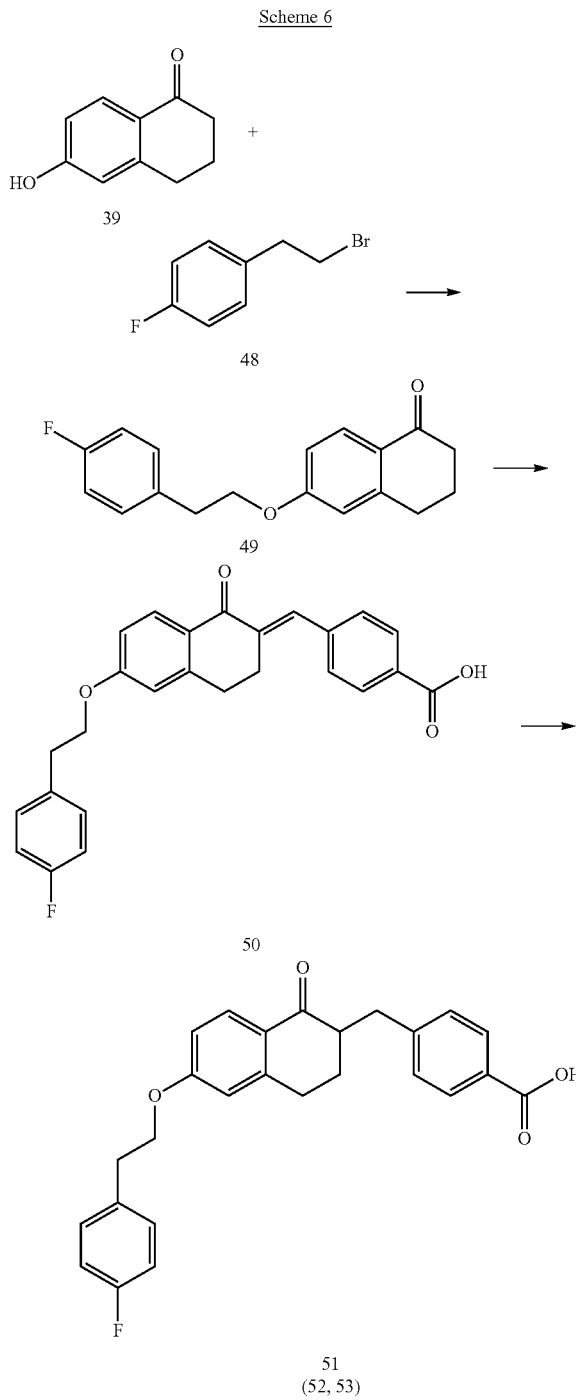

Scheme 6

For the preparation of Compounds 49-51, please refer to Scheme 6.

6-Hydroxy-1-tetralone (39) (1.0 g, 6.16 mmol) was suspended in DMF (15 mL) containing K$_2$CO$_3$ (2.0 g, 14.46 mmol) and KI (0.5 g). The reaction solution was treated with 4-fluorophenethybromide (48) (1.5 g, 7.38 mmol) and heated under 80° C. for 16 hours. The reaction progress was monitored using silica gel TLC with ethyl acetate:hexane (1:3). Upon completion, the reaction was filtered through a pad of celite and concentrated in vacuo. The crude thus obtained was purified by column chromatography (ethyl acetate/hexane, 1:4) to give Compound 49 (1.2 g, 68%).

2 mL of 2N NaOH was added to a stirring solution of Compound 49 (0.5 g, 1.76 mmol) and 4-carboxylbenzaldehyde (0.26 g, 1.76 mmol) in 10 mL of EtOH. The solution was stirred at room temperature for 20 hours and the resulting was acidified by 10% HCl, and precipitate was collected and washed well with water and then cold EtOH. The obtained solid was dried in vacuo to afford the Compound 50, 0.51 g (69%) as an off-white solid. Compound 50, $^1$H-NMR (300 MHz, DMSO): δ 8.01-7.98 (d, 2H), 7.94-7.91 (d, 1H), 7.67 (s, 1H), 7.63-7.60 (d, 2H), 7.40-7.35 (m, 2H), 7.17-7.11 (m, 2H), 6.97-6.93 (m, 2H), 4.31-4.26 (t, 2H), 3.08-3.04 (m, 4H), 2.93-2.89 (t, 2H). ESI-MS m/z calcd for C$_{26}$H$_{21}$FO$_4$ 416.14, found 417.2 [M+H]$^+$.

A mixture of Compound 50 (0.50 g, 1.2 mmol) and 10% palladium on charcoal (0.1 g) in methanol (100 mL) was stirred in an atmosphere of hydrogen at room temperature for 18 hours. Palladium was removed by filtration through a bed of Celite, and the filtrate was concentrated in vacuo. Purification by column chromatography (Hexane/EA=1:6) gave a white solid, Compound 51 (0.35 g, 70%). Compound 51, $^1$H-NMR (400 MHz, CDCl$_3$): δ 8.05-8.02 (m, 3H), 7.34-7.32 (d, 2H), 7.25-7.22 (m, 2H), 7.03-6.98 (m, 2H), 6.84-6.81 (dd, 1H), 6.65-6.64 (d, 1H), 4.20-4.17 (t, 2H), 3.56-3.53 (m, 1H), 3.09-3.06 (t, 2H), 2.89-2.86 (m, 2H), 2.76-2.69 (m, 2H), 2.07-2.03 (m, 1H), 1.79-1.73 (m, 1H). ESI-MS m/z calcd for C$_{26}$H$_{23}$FO$_4$ 418.16, found 419.2 [M+H]$^+$.

Compounds 52 and 53 were also produced according to Scheme 6 shown above.

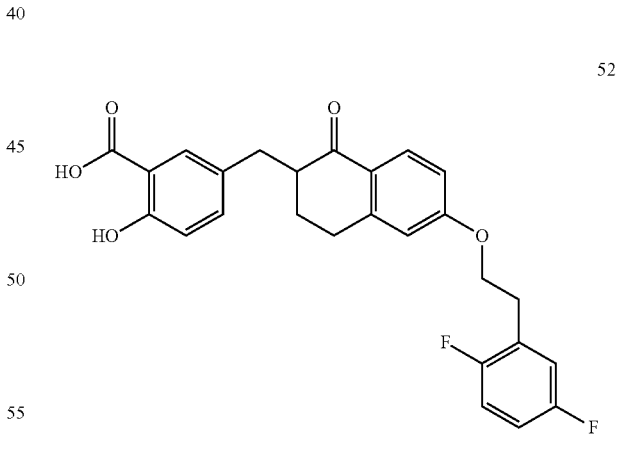

52

Compound 52, $^1$H-NMR (400 MHz, CD$_3$OD): δ 7.94-7.91 (d, 1H), 7.71-7.70 (d, 1H), 7.17-7.05 (m, 3H), 7.00-6.94 (m, 1H), 6.86-6.83 (dd, 1H), 6.77-6.76 (d, 1H), 6.75-6.73 (d, 1H), 4.29-4.25 (t, 2H), 3.27-3.26 (d, 1H), 3.14-3.11 (t, 2H), 2.98-2.83 (m, 2H), 2.71-2.51 (m, 2H), 2.08-2.01 (m, 1H), 1.75-1.69 (m, 1H). ESI-MS m/z calcd for C$_{26}$H$_{22}$F$_2$O$_5$ 452.14, found 453.2 [M+H]$^+$.

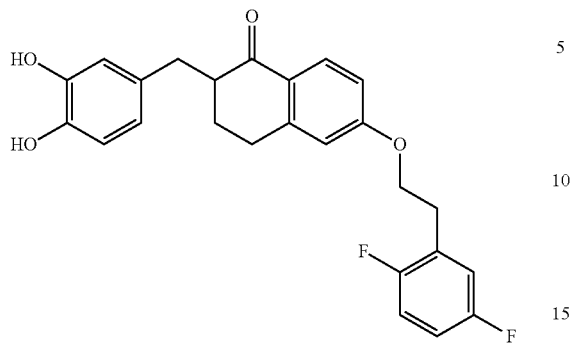
Compound 53, ¹H-NMR (300 MHz, CDCl₃): δ 8.03-8.00 (d, 1H), 7.04-6.88 (m, 3H), 6.83-6.63 (m, 5H), 5.20 (br, 2H), 4.31-4.27 (t, 2H), 3.35-3.29 (dd, 1H), 3.14-3.09 (t, 2H), 2.89-2.84 (m, 2H), 2.67-2.51 (m, 2H), 2.12-2.03 (m, 1H), 1.80-1.69 (m, 1H). ESI-MS m/z calcd for $C_{25}H_{22}F_2O_4$ 424.15, found 425.2 [M+H]⁺.
7. Compounds 54-62
Scheme 7
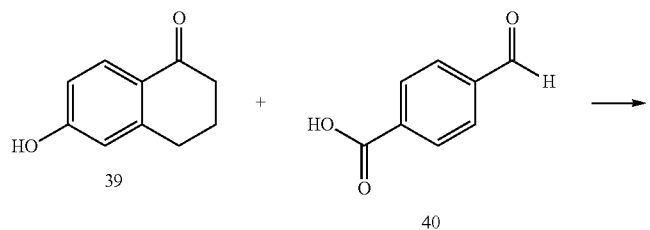
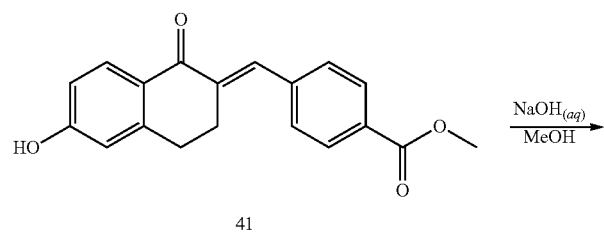
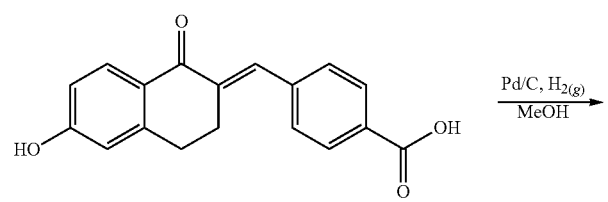

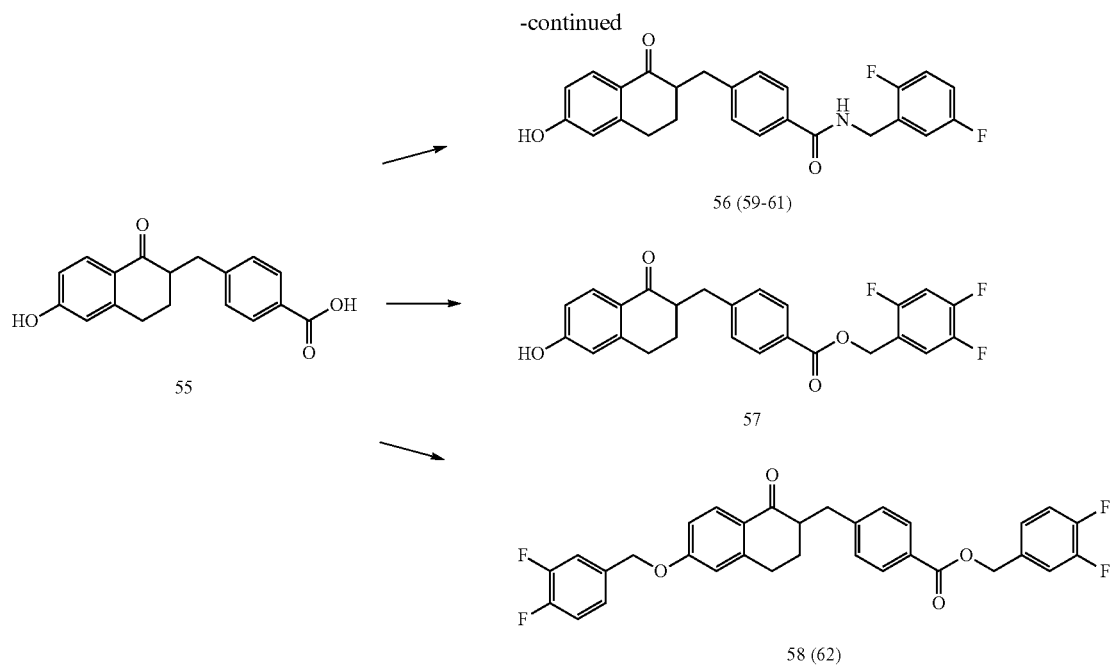

For the preparation of Compounds 54-58, please refer to Scheme 7.

A mixture of 6-hydroxy-1-tetralone (39) (1.0 g, 6.16 mmol), 4-carboxylbenzaldehyde (40) (1.0 g, 6.66 mmol) and concentrated HCl (50.0 mL) in methanol (75.0 mL) was heated at reflux for 18 hours. The mixture was allowed to cool to room temperature and then filtered. The residue was washed with a small amount of methanol and dried in vacuo to give Compound 41 (1.40 g, 74%) as a pale brown solid.

2N NaOH solution (5 mL) was added to a solution of the Compound 41 (2.5 g, 8.4 mmol) in the co-solvent of THF:MeOH=1.1 (50 mL) at room temperature for 5 hours. The reaction mixture was concentrated to remove the organic solvent. The residue was diluted with water and acidified to pH 4 with 2N HCl$_{(aq)}$. The resulting white precipitate was filtered, washed with H$_2$O and ether, and dried in vacuo to provide the product as a solid product, Compound 54, and the yield thereof was 1.4 g (5.0 mmol).

A mixture of Compound 54 (1.6 g, 5.4 mmol) and 10% Pd/C (dry, 0.5 g) in MeOH (100 mL) was stirred under an atmosphere of H$_2$ (1 atm) at room temperature for 16 hours. The mixture was filtered through celite and the filtrate was concentrated. The residue was not purified to provide a product, Compound 55, and the yield thereof was 1.6 g (5.4 mmol).

EDC-HCl (123.9 mg, 0.65 mmol), (2,5-difluorophenyl) methanamine (108.3 μl, 0.92 mmol), and HOBt (99 mg, 0.65 mmol) were added to a mixture solution of Compound 55 (137.0 mg, 0.46 mmol), NMM (76.2 μl, 0.69 mmol) and DMF (0.2 mL) in DCM (2.0 mL). The reaction mixture was stirred at room temperature for 16 hours. After that, the mixture was extracted with EtOAc and H$_2$O. The organic layer was dried (MgSO$_4$) and concentrated in vacuo to provide the product as a solid product (Compound 56). The yield thereof was 60 mg (0.142 mmol). Compound 56, $^1$H-NMR (400 MHz, CD$_3$OD): δ 7.87 (d, 1H), 7.80 (d, 2H), 7.36 (d, 2H), 7.14-7.08 (m, 2H), 7.05-6.99 (m, 1H), 6.71 (dd, 1H), 6.61 (s, 1H), 4.60 (s, 2H), 3.41 (d, 1H), 2.89-2.85 (m, 2H), 2.78-2.71 (m, 2H), 2.05-2.01 (m, 1H), 1.77-1.69 (m, 1H). ESI-MS m/z calcd for C$_{25}$H$_{21}$F$_2$NO$_3$ 421.15, found 422.5 [M+H]$^+$.

A mixture solution of Compound 55 (200 mg, 0.7 mmol), 1-(bromomethyl)-2,4,5-trifluorobenzene (99.0 μl, 0.5 mmol), KI (100.0 mg, 0.6 mmol) and the K$_2$CO$_3$ (206.0 mg, 1.5 mmol) in MeCN (5 mL) was stirred at room temperature for 16 hours. The mixture was diluted with H$_2$O and EtOAc. The organic layer was separated, dried (MgSO$_4$), and concentrated. The resulting material was purified by silica gel column chromatograph (EA:Hex=1:1) to provide a product, Compound 57, and the yield thereof was 10 mg (0.02 mmol). Compound 57, $^1$H-NMR (400 MHz, CDCl$_3$): δ 8.02-7.98 (m, 3H), 7.36-7.29 (m, 3H), 7.01-6.94 (m, 1H), 6.76 (dd, 1H), 6.30 (s, 1H), 5.46 (s, 1H), 5.35 (s, 2H), 3.54-3.51 (m, 1H), 2.88-2.85 (m, 2H), 2.76-2.71 (m, 2H), 2.06-2.02 (m, 1H), 2.01-1.76 (m, 1H). ESI-MS m/z calcd for C$_{25}$H$_{19}$F$_3$O$_4$ 440.12, found 441.2 [M+H]$^+$.

A mixture solution of Compound 55 (100 mg, 0.3 mmol), 4-(bromomethyl)-1,2-difluorobenzene (54.7 mg, 0.4 mmol) and the K$_2$CO$_3$ (103.0 mg, 1.1 mmol) in DMF (2 mL) was stirred at room temperature for 16 hours. The mixture was diluted with H$_2$O and EtOAc. The organic layer was separated, dried (MgSO$_4$), and concentrated. The resulting material was purified by silica gel column chromatograph (EA:Hex=1:4) to provide the product, Compound 58, and the yield thereof was 20 mg (0.04 mmol). Compound 58, $^1$H-NMR (300 MHz, CDCl$_3$): δ 8.06-7.98 (m, 3H), 7.33-7.20 (m, 4H), 7.19-7.16 (m, 4H), 6.88 (d, 1H), 6.72 (s, 1H), 5.30 (s, 2H), 5.05 (s, 2H), 3.52 (q, 1H), 2.91-2.87 (m, 2H), 2.74 (d, 2H), 2.08-2.02 (m, 1H), 1.83-1.69 (m, 1H). ESI-MS m/z calcd for C$_{32}$H$_{24}$F$_4$O$_4$ 548.16, found 549.3 [M+H]$^+$.

Compounds 59-62 were also produced according to Scheme 7 shown above.

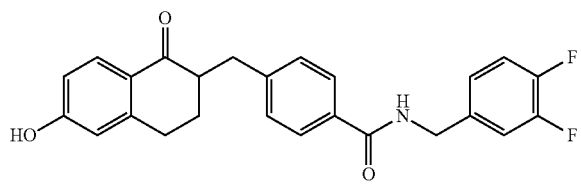

59

Compound 59, ¹H-NMR (300 MHz, CD₃OD): δ 7.86 (d, 1H), 7.78 (d, 2H), 7.34 (d, 2H), 7.24-7.15 (m, 3H), 6.70 (dd, 1H), 6.60 (s, 1H), 4.52 (s, 2H), 3.40-3.25 (m, 1H), 2.87-2.84 (m, 2H), 2.75-2.71 (m, 2H), 2.05-1.97 (m, 1H), 1.77-1.64 (m, 1H). ESI-MS m/z calcd for C$_{25}$H$_{21}$F$_2$NO$_3$ 421.15, found 422.2 [M+H]⁺.

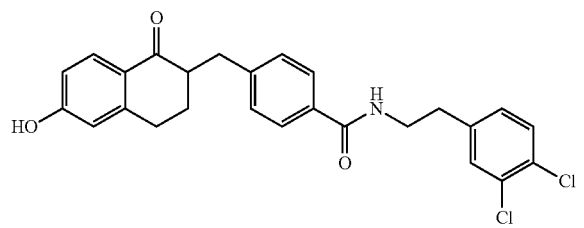

60

Compound 60, ¹H-NMR (400 MHz, CD₃OD): δ 7.88-7.86 (d, 1H), 7.71-7.69 (m, 2H), 7.44-7.42 (m, 2H), 7.34-7.32 (d, 2H), 7.20-7.17 (dd, 1H), 6.73-6.70 (dd, 1H), 6.62-6.61 (d, 1H), 3.60-3.57 (t, 2H), 3.41-3.38 (d, 1H), 2.92-2.86 (m, 4H), 2.77-2.73 (m, 2H), 2.06-1.95 (m, 1H), 1.76-1.67 (m, 1H). ESI-MS m/z calcd for C$_{26}$H$_{23}$Cl$_2$NO$_3$ 467.11, found 468.2 [M+H]⁺.

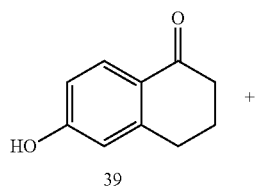

61

Compound 61, ¹H-NMR (400 MHz, CDCl₃): δ 7.97-7.95 (d, 1H), 7.40-7.38 (d, 2H), 7.29-7.27 (d, 2H), 7.00-6.95 (m, 2H), 6.72-6.70 (dd, 1H), 6.51-6.50 (d, 1H), 4.75 (br, 2H), 3.51-3.46 (m, 1H), 2.99 (s, 3H), 2.77-2.62 (m, 4H), 2.05-1.98 (m, 1H), 1.74-1.69 (m, 1H). ESI-MS m/z calcd for C$_{26}$H$_{22}$F$_3$NO$_3$ 453.16, found 476.2 [M+Na]⁺.

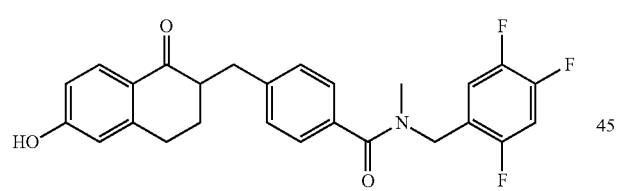

62

Compound 62, ¹H-NMR (300 MHz, CDCl₃): δ 8.07-8.00 (m, 3H), 7.32 (d, 2H), 7.26-7.16 (m, 2H), 7.10-6.96 (m, 4H), 6.93-6.90 (m, 1H), 7.50 (s, 1H), 5.39 (s, 2H), 5.15 (s, 2H), 3.53 (q, 1H), 2.95-2.88 (m, 2H), 2.72 (d, 2H), 2.08-2.02 (m, 1H), 1.83-1.73 (m, 1H). ESI-MS m/z calcd for C$_{32}$H$_{24}$F$_4$O$_4$ 548.16, found 549.3 [M+H]⁺.

8. Compounds 64-72

Scheme 8

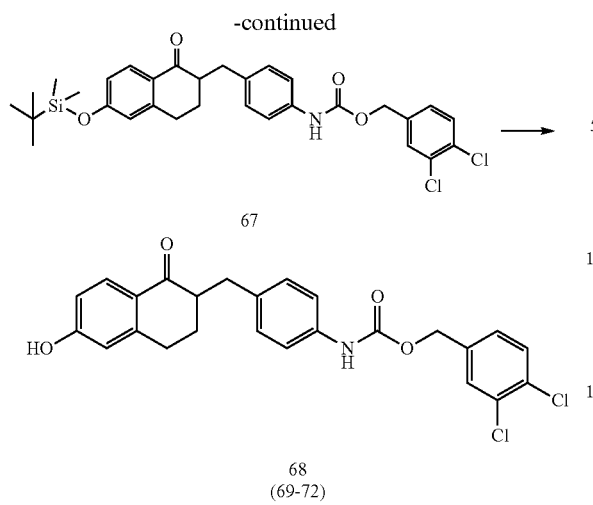

For the preparation of Compounds 64-68, please refer to Scheme 8.

A mixture of 6-hydroxy-1-tetralone (39) (1.0 g, 6.16 mmol), 4-nitrobenzaldehyde (63) (1.0 g, 6.61 mmol) and concentrated HCl (50.0 mL) in methanol (75.0 mL) was heated at reflux for 18 hours. The mixture was allowed to cool to room temperature and then filtered. The residue was washed with a small amount of methanol and dried in vacuo to give Compound 64 (1.54 g, 85%) as a pale brown solid.

Chloro-tert-butyldimethylsilane (1.15 g, 7.62 mmol) was added to a mixture of 6-hydroxy-1-tetralone (1.5 g, 5.08 mmol), imidazole (0.69 g, 10.16 mmol) in DMF (20 mL). The reaction mixture was stirred at room temperature for 4 hours. Saturated NH$_4$Cl (50 mL) was added to the reaction mixture, and then the precipitate solid was collected and washed with cold water. The obtained crude white solid was used without further purification as Compound 65, and the yield thereof was 2.04 g (4.98 mmol).

A MeOH (150 mL) solution of Compound 65 (1.20 g, 2.93 mmol) and Pd—C (240 mg) was stirred at room temperature for 3 hours under hydrogen atmosphere. Then the mixture was filtered and the filtrate was evaporated to give a product, crude brown oil. The crude brown oil was used without further purification as Compound 66, and the yield thereof was 1.09 g (2.87 mmol).

DIPEA (0.36 mL, 2.10 mmol) and triphosgene (230 mg, 0.77 mmol) was added to a solution of Compound 66 (268 mg, 0.70 mmol) in dichloromethane (10 mL) at 0° C. The reaction mixture was stirred for 1 hour at the same temperature. After that, the reaction mixture was warmed to room temperature, and stirred for further 2 hours. The solvent was evaporated under reduced pressure. The crude reaction mixture was dissolved in dichloromethane (10 mL) and cooled to 0° C., and then 3,4-dichlorobenzyl alcohol (186 mg, 1.05 mmol) and DIPEA (0.36 mL, 2.10 mmol) were added therein. After the addition, the reaction mixture was slowly warmed to room temperature and stirred overnight. The reaction mixture was quenched with saturated NH$_4$Cl and extracted with 3×20 mL of EtOAc. The combined organic layers were dried over MgSO$_4$ and concentrated under reduced pressure. The crude was purified on a silica gel column using 4:1 hexane-EtOAc as the eluant. The resulting product was Compound 67, and the yield thereof was 249 mg (0.43 mmol).

1 M tetra-butylammonium fluoride in THF (0.90 mL) was added to a solution of Compound 67 (175 mg, 0.30 mmol) in THF (5 mL). The reaction mixture was stirred for 3 hours. The solvent was evaporated under reduced pressure. The crude residue was dissolved in EtOAc and washed with 3×10 mL of saturated NH$_4$Cl. The combined organic layers were dried over MgSO$_4$ and concentrated under reduced pressure. The crude product was purified on a silica gel column using 1:1 hexane-EtOAc as the eluant. The resulting product was Compound 68, and the yield thereof was 72 mg (0.154 mmol).

Compounds 69-72 were also produced according to Scheme 8 shown above.

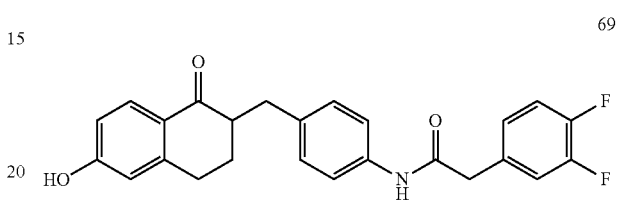

Compound 69, $^1$H-NMR (400 MHz, CD$_3$OD): δ 7.87-7.85 (d, 1H), 7.48-7.46 (d, 2H), 7.27-7.14 (m, 3H), 7.19-7.17 (d, 2H), 6.72-6.69 (dd, 1H), 6.61-6.60 (d, 1H), 3.66 (s, 2H), 3.28-3.27 (d, 1H), 2.91-2.78 (m, 2H), 2.72-2.62 (m, 2H), 2.06-1.98 (m, 1H), 1.74-1.59 (m, 1H). ESI-MS m/z calcd for C$_{25}$H$_{21}$F$_2$NO$_3$ 421.15, found 444.2 [M+Na]$^+$.

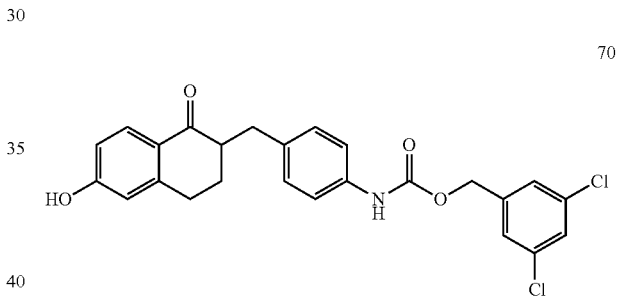

Compound 70, $^1$H-NMR (300 MHz, CD$_3$OD): δ 7.88-7.85 (d, 1H), 7.39-7.35 (m, 5H), 7.17-7.14 (d, 2H), 6.73-6.69 (dd, 1H), 6.61-6.60 (d, 1H), 5.15 (s, 2H), 3.27-3.26 (d, 1H), 2.89-2.82 (m, 2H), 2.70-2.57 (m, 2H), 2.05-1.99 (m, 1H), 1.73-1.66 (m, 1H). ESI-MS m/z calcd for C$_{25}$H$_{21}$Cl$_2$NO$_4$ 469.08, found 492.1 [M+Na]$^+$.

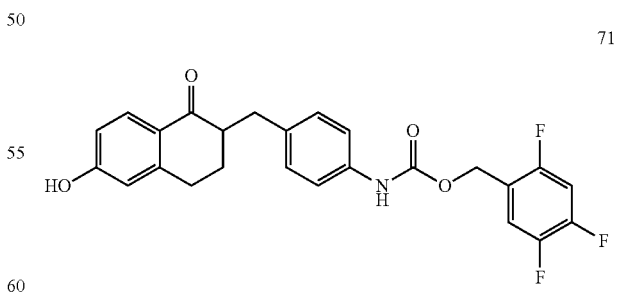

Compound 71, $^1$H-NMR (300 MHz, CDCl$_3$): δ 8.02-7.99 (d, 1H), 7.32-7.25 (m, 2H), 7.19-7.16 (d, 2H), 7.12-6.91 (m, 1H), 6.77-6.73 (dd, 1H), 6.63-6.62 (d, 2H), 5.19 (s, 2H), 3.43-3.40 (m, 1H), 2.88-2.83 (m, 2H), 2.65-2.61 (m, 2H), 2.10-2.02 (m, 1H), 1.74-1.65 (m, 1H). ESI-MS m/z calcd for C$_{25}$H$_{20}$F$_3$NO$_4$ 455.13, found 478.2 [M+Na]$^+$.

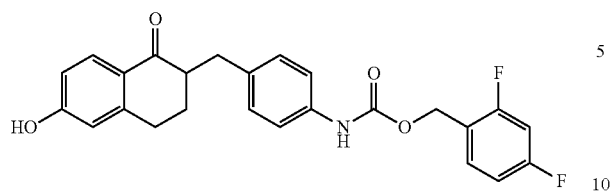

72

Compound 72, $^1$H-NMR (400 MHz, CD$_3$OD): δ 7.94-7.91 (d, 1H), 7.71-7.70 (d, 1H), 7.17-7.05 (m, 3H), 7.00-6.94 (m, 1H), 6.86-6.83 (dd, 1H), 6.77-6.76 (d, 1H), 6.75-6.73 (d, 1H), 4.29-4.25 (t, 2H), 3.27-3.26 (d, 1H), 3.14-3.11 (t, 2H), 2.98-2.83 (m, 2H), 2.71-2.51 (m, 2H), 2.08-2.01 (m, 1H), 1.75-1.69 (m, 1H). ESI-MS m/z calcd for C$_{26}$H$_{22}$F$_2$O$_5$ 452.14, found 453.2 [M+H]$^+$.

9. Compounds 74-77

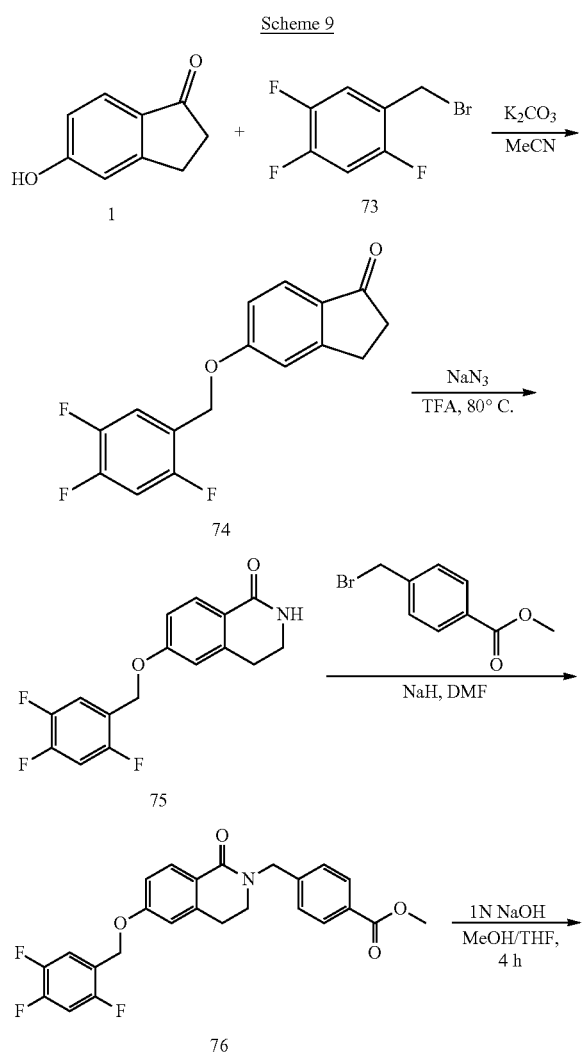

Scheme 9

77

For the preparation of Compounds 74-77, please refer to Scheme 9.

A mixture solution of the 5-hydroxyindanone (1) (1.0 g, 6.4 mmol), alkyl bromide (73) (941 μl, 7.1 mmol) and the K$_2$CO$_3$ (2.0 g, 14.1 mmol) in MeCN (50 mL) was stirred at room temperature for 16 hours. The mixture was concentrated to remove the organic solvent. After that, DCM (10 mL) was added to the mixture and filtered to remove K$_2$CO$_3$. The filtrate was concentrated without further purification to provide a product as a solid product, Compound 74, and the yield thereof was 1.4 g (4.8 mmol).

NaN$_3$ was added to a solution of Compound 73 (0.5 g, 1.7 mmol) in TFA (15 mL) to form a mixture and the mixture was stirred at 80° C. for 3 hours. After cooling to room temperature, H$_2$O (10 mL) was added to the mixture and the mixture was concentrated. The residue was extracted with EA and NaHCO$_3$. The combined organic layer were dried over MgSO$_4$, filtered and concentrate without further purification to provide the product as a solid product, Compound 75, and the yield thereof was 200.0 mg (0.7 mmol).

NaH (60%, 40 mg, 1.3 mmol) was slowly added to a solution of Compound 75 (200 mg, 0.65 mmol) in DMF (10 mL) at room temperature to form a mixture and the mixture was stirred for 10 minutes. Next, alkyl bromide (180 mg, 0.8 mmol) was added to the mixture. After that, the reaction mixture was stirred for 16 hours. The mixture was extracted with EtOAc and NaHCO$_3$. The organic layer was concentrated to dryness. The resulting material was purified by silica gel column chromatograph (EA:Hex=1:1) to provide the product, Compound 76, and the yield thereof was 180.0 mg (0.4 mmol).

1N NaOH solution (10 mL) was added to a solution of Compound 76 (180.0 mg, 0.4 mmol) in the co-solvent of THF:MeOH=1:1 (10 mL) at room temperature for 4 hours. The reaction mixture was concentrated to remove the organic solvent. The residue was diluted with water and acidified to pH 4 with 2N HCl$_{(aq)}$. The resulting white precipitate was filtered, washed with H$_2$O and ether, and dried in vacuo to provide the product as a solid product, Compound 77, and the yield thereof was 143.0 mg (0.32 mmol). Compound 77, $^1$H-NMR (400 MHz, CD$_3$OD): δ 8.02-7.95 (m, 3H), 7.52-7.43 (m, 3H), 7.27-7.20 (m, 1H), 7.10 (d, 1H), 6.90 (s, 1H), 5.16 (s, 2H), 4.84 (s, 2H), 3.55 (t, 2H), 2.99 (t, 2H). ESI-MS m/z calcd for C$_{24}$H$_{18}$F$_3$NO$_4$ 441.12, found 442.2 [M+H]$^+$.

10. Compounds 79-81

Scheme 10

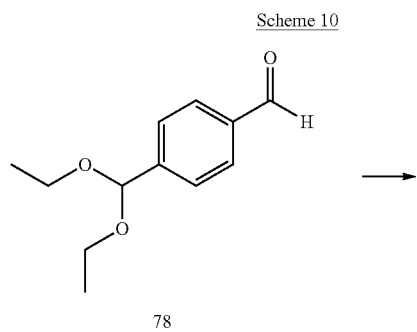

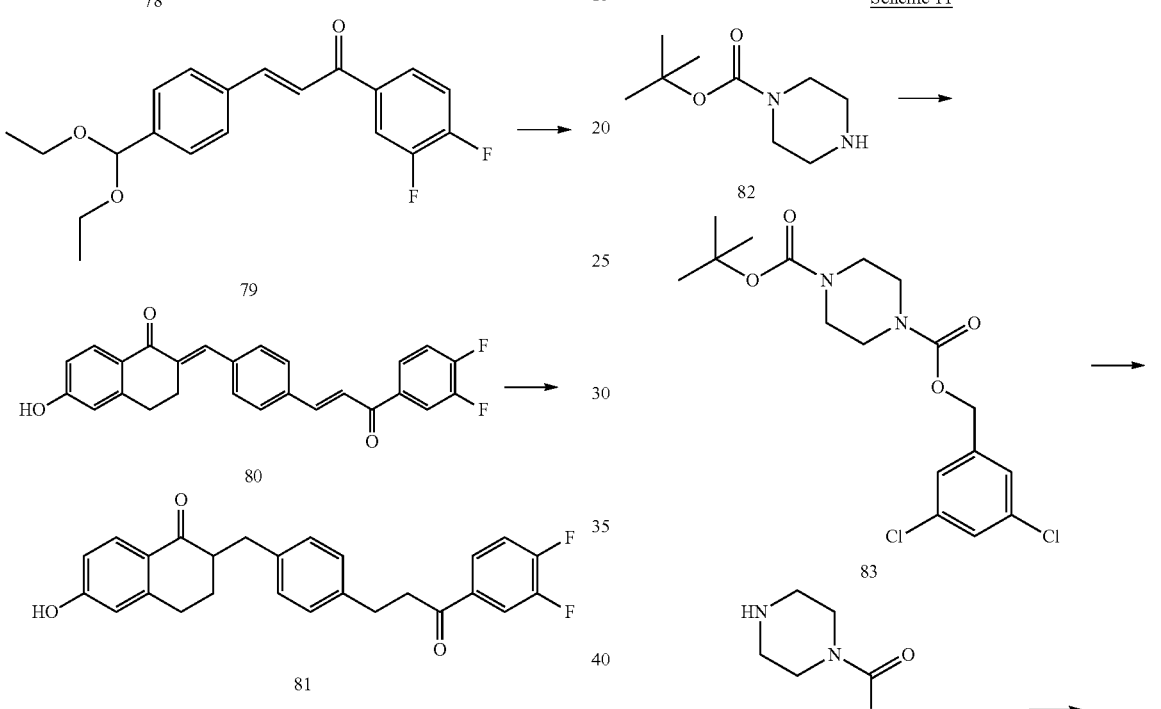

For the preparation of Compounds 79-81, please refer to Scheme 10.

Terephthalaldehyde monodiethylacetal (78) (0.63 g, 3.0 mmol) and 3,4-difluoroacetophenone (0.45 g, 2.9 mmol) were mixed and dissolved in 15 mL of methanol and stirred at 5° C. for a few minutes. 4 mL of 1N NaOH solution (aq) was added into the above solution by dropping over several minutes. The mixture obtained was stirred at room temperature (27° C.) for 18 hours. Product formation was indicated by the appearance of precipitate and change in color of the reaction mixture. TLC was used to monitor the reaction and upon completion, acidified ice was added to the mixture for quenching the reaction. The precipitate was collected as yellow powder (Compound 79) (0.78 g, 78%). The crude yellow powder (Compound 79) was used in the next step without further purification.

A mixture of 6-hydroxy-1-tetralone (0.33 g, 2 mmol), The yellow powder (Compound 79) (0.77 g, 2.22 mmol) and concentrated HCl (5.0 mL) in methanol (7.50 mL) was heated at reflux for 18 hours. The mixture was allowed to cool to room temperature and then filtered. The residue was washed with a small amount of methanol and dried in vacuo to give Compound 80 (0.54 g, 65%) as a pale yellow solid.

A mixture of Compound 80 (0.3 g, 0.72 mmol) and 10% palladium on charcoal (0.1 g) in methanol (20 mL) was stirred in an atmosphere of hydrogen at room temperature for 18 hours. Palladium was removed by filtration through a bed of Celite, and the filtrate was concentrated in vacuo. Purification by column chromatography (Hexane/EA=3:1) gave a brown solid, Compound 81 (0.14 g, 47%). Compound 81, $^1$H-NMR (300 MHz, CDCl$_3$): δ 8.01-7.98 (d, 1H), 7.81-7.69 (m, 2H), 7.27-7.12 (m, 5H), 6.81-6.77 (dd, 1H), 6.66 (s, 1H), 3.44-3.39 (dd, 1H), 3.27-3.22 (m, 2H), 3.05-3.00 (m, 2H), 2.88-2.83 (m, 2H), 2.71-2.58 (m, 2H), 2.08-2.02 (m, 1H), 1.81-1.70 (m, 1H). ESI-MS m/z calcd for C$_{26}$H$_{22}$F$_2$O$_3$ 420.15, found 421.2 [M+H]$^+$.

11. Compounds 83-85

For the preparation of Compounds 83-85, please refer to Scheme 11.

DIPEA (1.86 mL, 10.72 mmol) and triphosgene (0.80 g, 2.68 mmol) were added to a solution of the piperazine (82) (0.50 g, 2.68 mmol) in dichloromethane (20 mL) at 0° C. The reaction mixture was stirred for 1 hour at the same temperature. Then, the reaction mixture was warmed to room temperature, and stirred for further 2 hours. The solvent was evaporated under reduced pressure. After that, the reaction mixture was dissolved in dichloromethane (20 mL), and 3,5-dichlorobenzyl alcohol (0.71 g, 4.02 mmol) and DIPEA (1.86 mL, 10.72 mmol) were added therein. After the addition, the reaction mixture was heated to reflux overnight. The reaction mixture was quenched with saturated NH$_4$Cl and extracted with 3×20 mL of dichloromethane. The combined organic layers were dried over MgSO$_4$ and concentrated under reduced pressure. The crude was purified on a silica gel column using 4:1 hexane-EtOAc as the eluant. The resulting product was Compound 83, and the yield thereof was 0.87 g (2.22 mmol).

4M HCl in 1,4-dioxane (5 mL) was added to the Compound 83 (0.87 g, 2.22 mmol) at 0° C. and the reaction mixture was stirred at room temperature for 3 hours. The solvent was evaporated under reduced pressure. The crude white solid was used as such for the next step without further purification as Compound 84, and the yield thereof was 0.75 g (2.09 mmol).

Concentrated HCl (0.1 mL) was added to a mixture of 6-hydroxy-1-tetralone (41 mg, 0.25 mmol), paraformaldehyde (77 mg, 1.25 mmol), and piperazine hydrogen chloride salt (364 mg, 1.00 mmol) in i-PrOH (5 mL), and then, the mixture was heated at 80° C. overnight. The solvent was evaporated under reduced pressure. The crude residue was dissolved in EtOAc and washed with saturated NaHCO$_3$. The combined organic layers were dried over MgSO$_4$ and concentrated under reduced pressure. The crude was purified on a silica gel column using 1:1 hexane-EtOAc as the eluant. The resulting product was Compound 85, and the yield thereof was 30 mg (0.065 mmol). Compound 85, $^1$H-NMR (300 MHz, CDCl$_3$): δ 7.96-7.93 (d, 1H), 7.31-7.30 (t, 1H), 7.22-7.21 (d, 2H), 6.76-6.72 (dd, 1H), 6.66-6.65 (d, 1H), 5.07 (s, 2H), 3.54-3.47 (m, 5H), 2.95-2.90 (m, 4H), 2.67-2.51 (m, 3H), 2.44-2.30 (m, 2H), 1.96-1.88 (m, 1H). ESI-MS m/z calcd for C$_{23}$H$_{24}$Cl$_2$N$_2$O$_4$ 462.11, found 463.2 [M+H]$^+$.

12. Compounds 87-89

Scheme 12

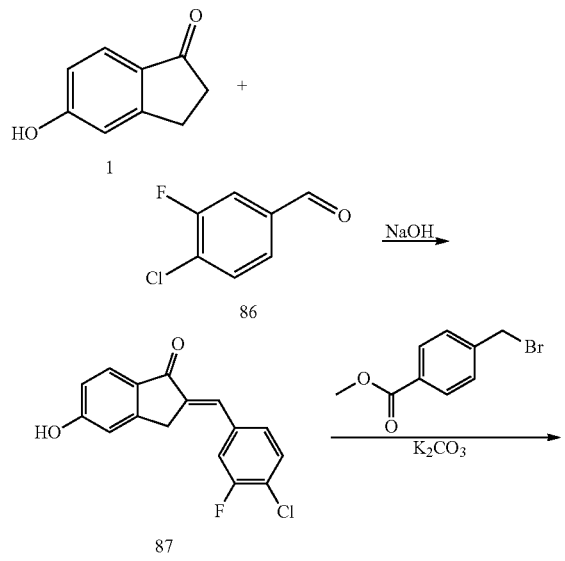

For the preparation of Compounds 87-88, please refer to Scheme 12.

1N NaOH solution (2 mL) was added to a mixture of the 5-hydroxyindanone (1) (1.0 g, 6.41 mmol) and aldehyde (86) (1.02 g, 7.05 mmol) in the MeOH (2 mL) at room temperature and stirred for 16 hours. The reaction mixture was concentrated to remove the organic solvent. The residue was purified by silica gel column chromatograph (EA: Hex=1:1) to provide a product, Compound 87, and the yield thereof was 1.1 g (4.06 mmol).

A mixture solution of Compound 87 (1.0 mg, 1.74 mmol), methyl 4-bromomethylbenzoate (0.14 ml, 0.61 mmol) and the K$_2$CO$_3$ (210.8 mg, 1.53 mmol) in DMF (10 mL) was stirred at room temperature for 16 hours. The mixture was concentrated to remove the organic solvent. After that, EA (10 mL) was added to the mixture and the mixture was filtered to remove K$_2$CO$_3$. The filtrate was extracted with EA and NaHCO$_3$. The organic layer dried over MgSO$_4$ and concentrated without further purification to provide the product as a solid product, Compound 88, and the yield thereof was 84.0 mg (0.20 mmol). Compound 88, $^1$H-NMR (300 MHz, DMSO): δ 8.01 (d, 2H), 7.81 (dd, 1H), 7.78 (dd, 1H), 7.73 (dd, 1H), 7.69-7.62 (m, 3H), 7.44 (s, 1H), 7.27 (s, 1H), 7.15 (d, 1H), 5.37 (s, 2H), 4.09 (s, 2H), 3.86 (s, 3H). ESI-MS m/z calcd for C$_{25}$H$_{18}$ClFO$_4$ 436.09, found 438.2 [M+H]$^+$.

Compound 89 was also produced according to Scheme 12 shown above.

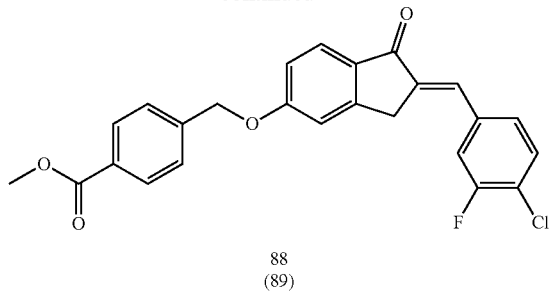

88
(89)

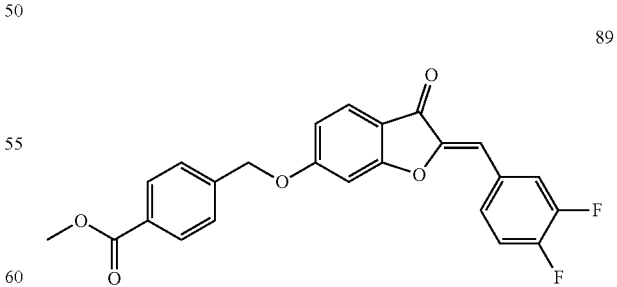

89

Compound 89, $^1$H-NMR (300 MHz, DMSO): δ 8.08-7.98 (m, 3H), 7.86-7.83 (m, 1H), 7.84 (d, 1H), 7.63 (d, 3H), 7.31 (d, 1H), 6.97 (d, 1H), 6.90 (s, 1H), 5.41 (s, 2H), 3.34 (s, 3H). ESI-MS m/z calcd for C$_{24}$H$_{16}$F$_2$O$_5$ 422.10, found 445.1 [M+Na]$^+$.

13. Compounds 91-93

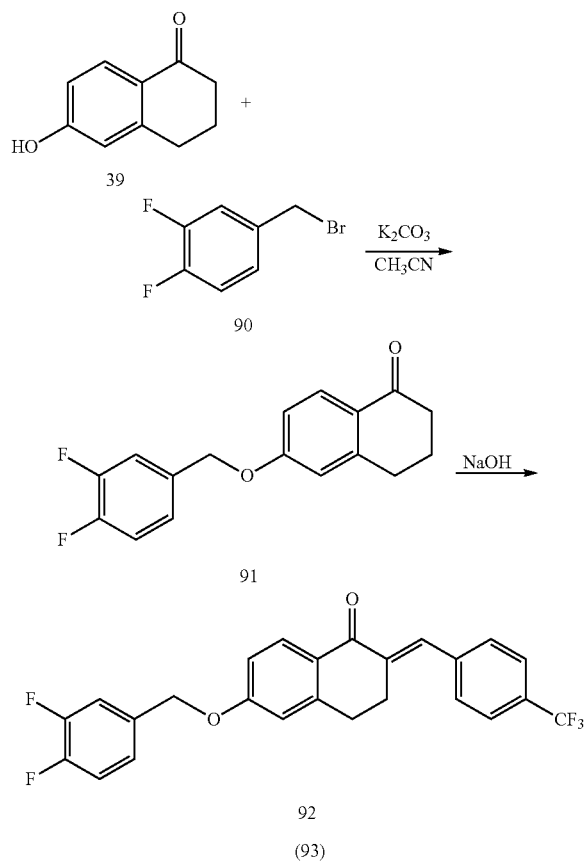

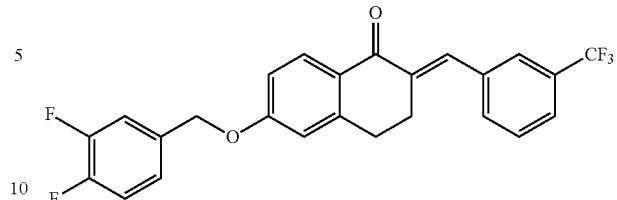

Compound 93, ¹H-NMR (400 MHz, CDCl₃): δ 8.13 (d, 1H), 7.82 (s, 1H), 7.65 (s, 1H), 7.61-7.52 (m, 3H), 7.30-7.16 (m, 3H), 6.94 (d, 1H), 6.78 (s, 1H), 5.08 (s, 2H), 3.10-3.07 (m, 2H), 2.95-2.92 (m, 2H). ESI-MS m/z calcd for $C_{25}H_{17}F_5O_2$ 444.11, found 467.1 [M+Na]⁺.

14. Compounds 95-96

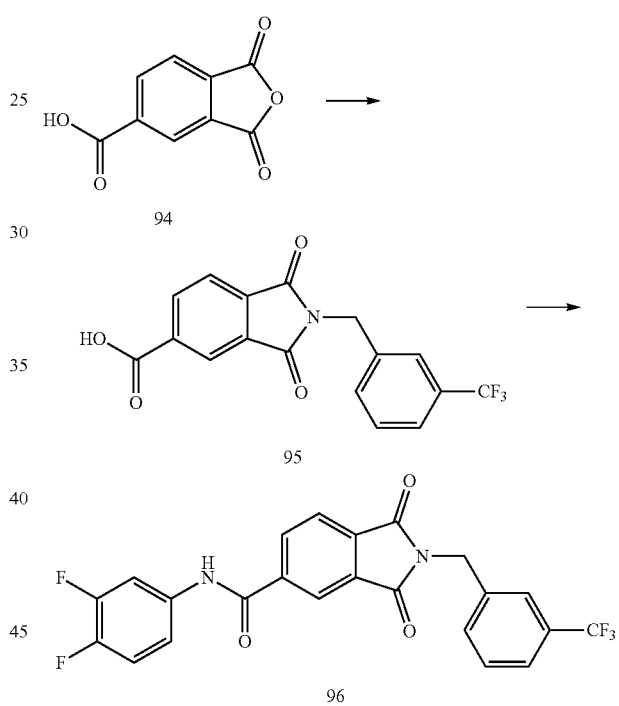

For the preparation of Compounds 91-92, please refer to Scheme 14.

A mixture solution of the 5-hydroxyindanone (1) (288.0 mg, 1.74 mmol), alkyl bromide (90) (0.25 ml, 1.91 mmol) and the K₂CO₃ (483.7 mg, 3.5 mmol) in MeCN (50 mL) was stirred at room temperature for 16 hours. The mixture was concentrated to remove the organic solvent. After that. DCM (10 mL) was added to the mixture and the mixture was filtered to remove K₂CO₃. The filtrate was concentrated without further purification to provide a product as a solid product, Compound 91, and the yield thereof was 0.4 g (1.21 mmol).

1N NaOH solution (2 mL) was added to a mixture of Compound 91 (100 mg, 0.35 mmol) and 4-trifluoromethyl benzaldehyde (0.05 mL, 0.35 mmol) in the MeOH (2 mL) at room temperature and the mixture was stirred for 16 hours. The reaction mixture was concentrated to remove the organic solvent. The residue was purified by silica gel column chromatograph (EA:Hex=1:3) to provide the product, Compound 92, and the yield thereof was 25.3 mg (0.06 mmol). Compound 92, ¹H-NMR (400 MHz, CDCl₃): δ 8.13 (d, 1H), 7.82 (s, 1H), 7.67 (d, 2H), 7.51 (d, 2H), 7.23-7.16 (m, 2H), 6.96-6.93 (m, 2H), 6.78 (s, 1H), 5.09 (s, 2H), 3.10-3.07 (m, 2H), 2.95-2.92 (m, 2H). ESI-MS m/z calcd for $C_{25}H_{17}F_5O_2$ 444.11, found 467.1 [M+Na]⁺.

Compound 93 was also produced according to Scheme 13 shown above.

For the preparation of Compounds 95-96, please refer to Scheme 15.

1,2,4-Benzenetricarboxylic acid anhydride (94) (1.76 g, 10 mmole) was treated with 3-trifluoromethylbenzylamine (1.92 g, 10 mmole) in acetic acid 10 mL under refluxing conditions. After 18 hours, acetic acid was removed by vacuo. The obtained solid was washed by H₂O, filtered and dried to get a carboxylic acid, Compound 95.

The carboxylic acids 95 (0.1 g, 0.286 mmol) was converted to the corresponding acyl halides by using oxalyl chloride (0.43 mmol, 2 eq) and a catalytic amount of DMF in anhydrous CH₂Cl₂ 10 mL at 0° C., and then warmed to room temperature, stirred overnight. Excess oxalyl chloride and CH₂Cl₂ was removed by vacuo. The crude acyl halide was dissolved in new CH₂Cl₂ and 3,4-difluoroaniline (0.044 g, 0.34 mmole), and Et₃N (0.4 mmole) were added therein and stirred for 3 hours. The reaction mixture was concentrated to remove the organic solvent. The residue was purified by silica gel column chromatograph (EA:Hex=3:1) to provide a product, Compound 96. Compound 96, $^1$H-NMR (300 MHz, CDCl$_3$): δ 8.31-8.28 (m, 2H), 8.02-7.99 (m, 1H), 7.90 (s, 1H), 7.80-7.73 (m, 1H), 7.69 (s, 1H), 7.65-7.63 (d, 1H), 7.58-7.55 (d, 1H), 7.49-7.44 (t, 1H), 7.26-7.17 (m, 2H), 4.93 (s, 2H). ESI-MS m/z calcd for C$_{23}$H$_{13}$F$_5$N$_2$O$_3$ 460.08, found 483.1 [M+Na]$^+$.

15. Compounds 98-102

Scheme 15

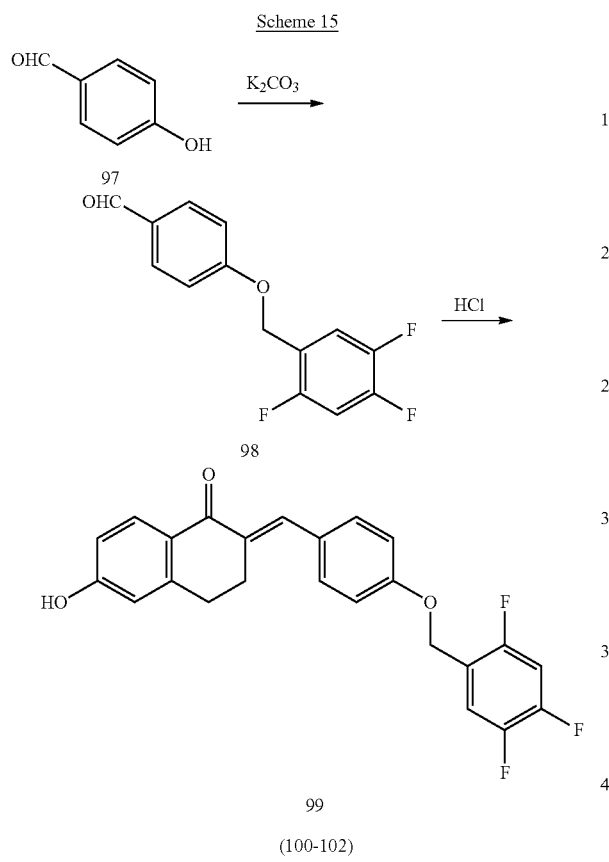

(100-102)

For the preparation of Compounds 98-99, please refer to Scheme 15.

K$_2$CO$_3$ (3.4 g, 24.6 mmol) and 2,4,5-tifluorobenzyl bromide (2.3 g, 10.0 mmol) were added to a stirred solution of 4-hydroxybenzaldehyde (97) (1.0 g, 8.2 mmol) in anhydrous CH$_3$CN. The resulting solution was heated at 80° C. overnight. After consumption of the starting material as confirmed by TLC, the reaction was quenched by addition of saturated ammonium chloride. The resulting suspension was extracted with CH$_2$Cl$_2$ (3×100 mL). The combined organic extracts were dried over MgSO$_4$ and concentrated in vacuo. The crude material was purified by recrystallization in hexane/ethanol (1:1) to obtain Compound 98, 1.6 g.

A mixture of 6-hydroxy-1-tetralone (0.5 g, 3.08 mmol), Compound 98 (0.9 g, 3.39 mmol) and concentrated HCl (15.0 mL) in methanol (21.0 mL) was heated at reflux for 18 hours. The mixture was allowed to cool to room temperature and then filtered. The residue was washed with a small amount of methanol and dried in vacuo to give a solid product, Compound 99 (0.46 g, 36%). Compound 99, $^1$H-NMR (300 MHz, DMSO): δ 10.39 (s, 1H), 7.84 (d, 1H), 7.81-7.60 (m, 3H), 7.50 (d, 2H), 7.12 (d, 2H), 6.76 (dd, 1H), 6.67 (s, 1H), 5.15 (s, 2H), 3.03 (t, 2H), 2.83 (t, 2H). ESI-MS m/z calcd for C$_{24}$H$_{17}$F$_3$O$_3$ 410.11, found 411.2 [M+H]$^+$.

Compounds 100-102 were also produced according to Scheme 15 shown above.

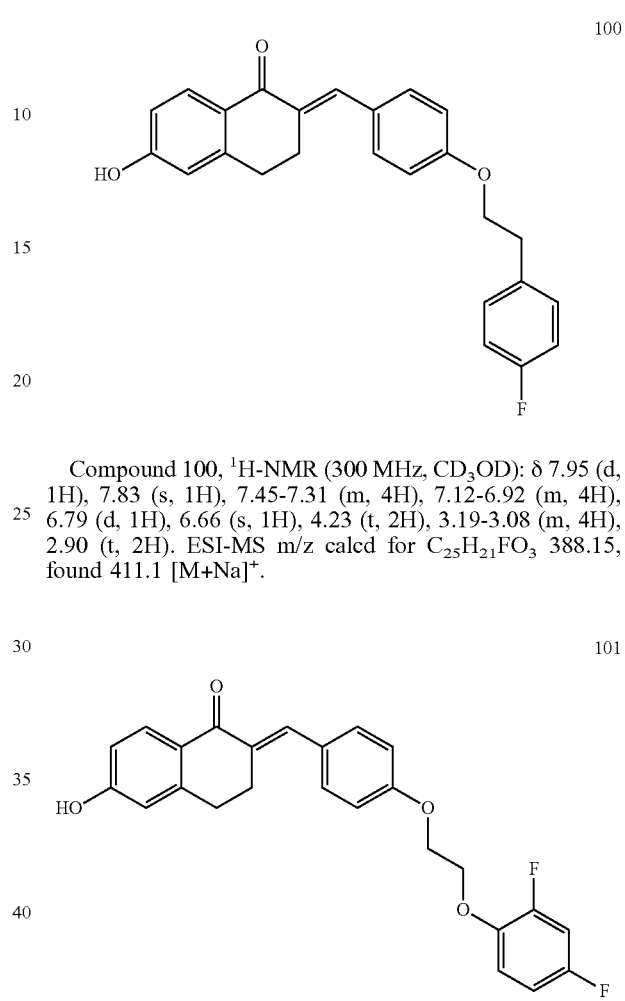

Compound 100, $^1$H-NMR (300 MHz, CD$_3$OD): δ 7.95 (d, 1H), 7.83 (s, 1H), 7.45-7.31 (m, 4H), 7.12-6.92 (m, 4H), 6.79 (d, 1H), 6.66 (s, 1H), 4.23 (t, 2H), 3.19-3.08 (m, 4H), 2.90 (t, 2H). ESI-MS m/z calcd for C$_{25}$H$_{21}$FO$_3$ 388.15, found 411.1 [M+Na]$^+$.

Compound 101, $^1$H-NMR (300 MHz, DMSO): δ 10.40 (s, 1H), 7.87 (d, 1H), 7.61 (s, 1H), 7.50-7.47 (d, 2H), 7.34-7.23 (m, 2H), 7.08-7.03 (m, 3H), 6.76 (dd, 1H), 6.67 (s, 1H), 4.39 (s, 4H), 3.03 (t, 2H), 2.83 (t, 2H). ESI-MS m/z calcd for C$_{25}$H$_{20}$F$_2$O$_4$ 422.13, found 423.2 [M+H]$^+$.

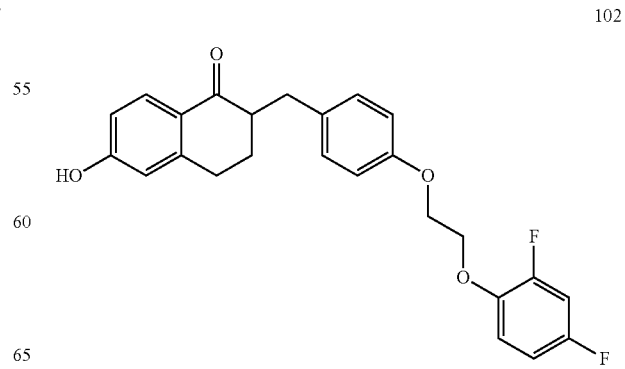

Compound 102, $^1$H-NMR (300 MHz, CDCl$_3$): δ 8.01 (d, 1H), 7.15 (d, 2H), 7.04-6.96 (m, 1H), 6.88 (d, 3H), 6.84-6.74 (m, 2H), 6.63 (s, 1H), 5.54 (s, 1H), 4.38-4.28 (m, 4H), 3.38 (d, 1H), 2.88-2.84 (m, 2H), 2.66-2.63 (m, 2H), 2.09-2.04 (m, 1H), 1.81-1.71 (m, 1H). ESI-MS m/z calcd for C$_{25}$H$_{22}$F$_2$O$_4$ 424.15, found 425.2 [M+H]$^+$.

16. Compound 110

TEA (10.4 mL) and di-tert-butyl dicarbonate (9.83 g, 45.1 mmol) was added to a solution of 5-aminoindan 22 (5.00 g, 37.5 mmol) in DCM (100 mL), and then stirred at room temperature for 3 hours.

The solvent was removed under reduced pressure, and then the residue was diluted with H$_2$O and extracted with EA several times. The combined organic layers were washed Scheme 16

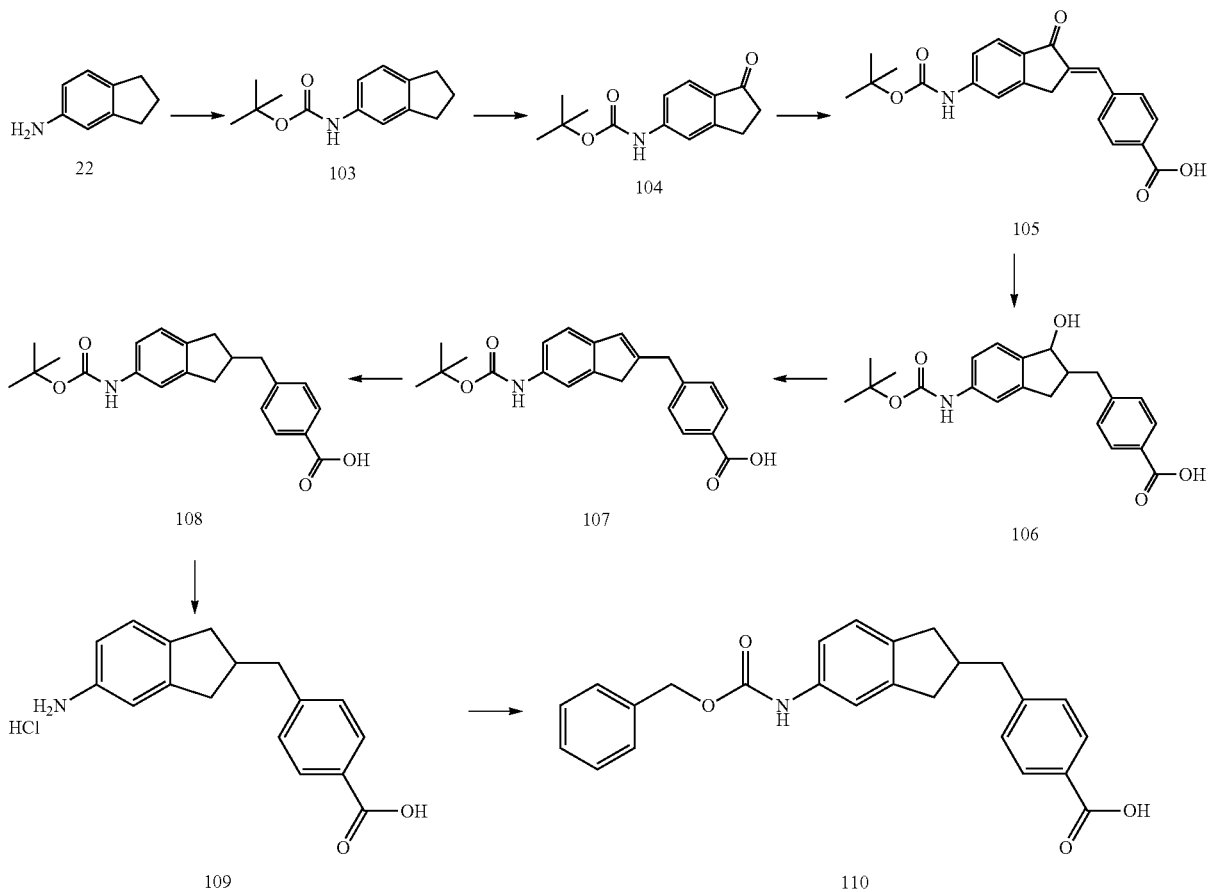

For the preparation of Compound 100, please refer to Scheme 16.

with brine and dried over MgSO$_4$, and then concentrated in vacuo to afforded tert-butyl N-(indan-5-yl) carbamate as a white solid that was used without further purification. Tert-butyl N-(indan-5-yl) carbamate was Compound 103, and the yield thereof was 8.61 g (36.9 mmol).

Scheme 16-1

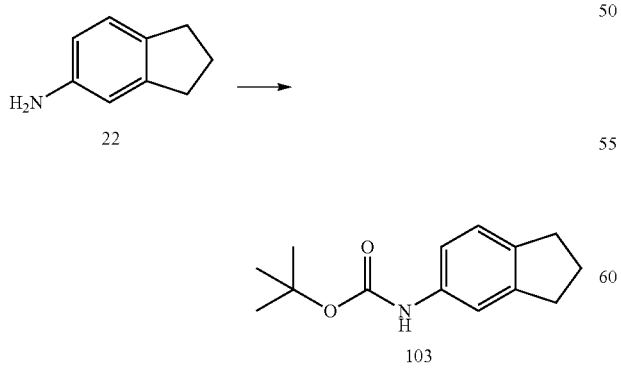

For details of the preparation of Compound 103, refer to Scheme 16-1 and the following.

Scheme 16-2

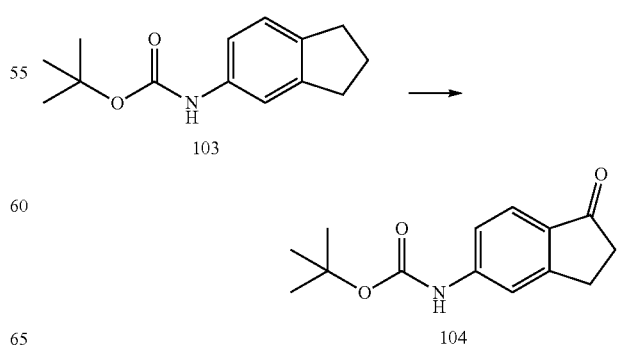

For details of the preparation of Compound 104, refer to Scheme 16-2 and the following.

CrO$_3$ (2.57 g, 25.7 mmol) which dissolved in AcOH aqueous solution (10 mL, 50%) was slowly added to a solution of Compound 103 (2.00 g, 8.6 mmol) in AcOH (10 mL) at 0° C. The reaction mixture was warmed to room temperature, and stirred for 1 hour.

The reaction mixture was concentrated in vacuo, and then basified with 1N NaOH and extracted with 3×30 mL of EtOAc. The combined organic layers were dried over MgSO$_4$ and concentrated in vacuo to afford 1-Indanone as a white solid that was used without further purification. 1-Indanone was Compound 104, and the yield thereof was 1.60 g (6.5 mmol).

Scheme 16-3

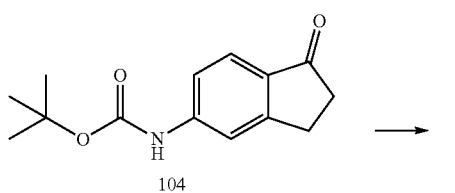
104

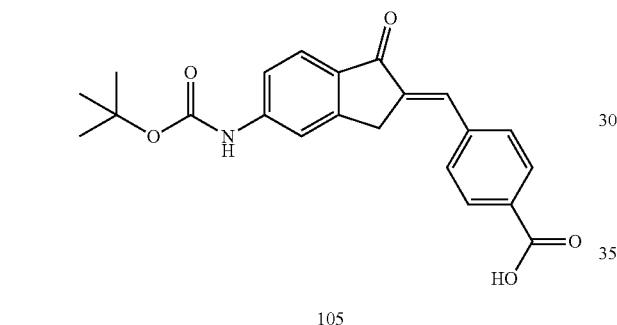
105

For details of the preparation of Compound 105, refer to Scheme 16-3 and the following.

1N NaOH (3.7 mL) was added to a mixture of Compound 104 (0.31 g, 1.3 mmol) and aldehyde (0.19 g, 1.3 mmol) in MeOH (20 mL). The reaction mixture was stirred at room temperature overnight.

The solvent was removed under reduced pressure. Then, the reaction mixture was acidified with 1N HCl. The precipitate solid was collected by filtration and washed with MeOH. The resulting product was Compound 105, and the yield thereof was 0.44 g (1.2 mmol).

Scheme 16-4

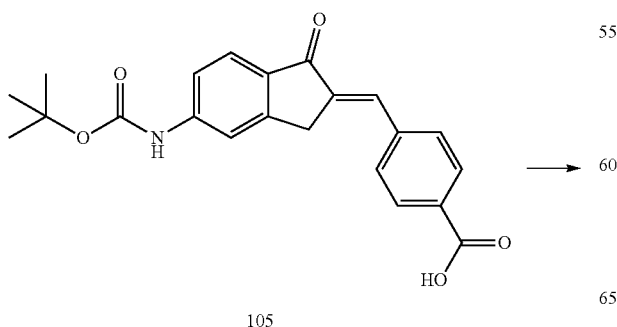
105

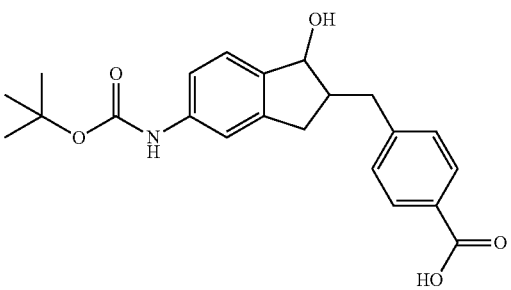
106

For details of the preparation of Compound 106, refer to Scheme 16-4 and the following.

A MeOH (150 mL) solution of Compound 105 (0.40 g, 1.05 mmol) and Pd—C (0.08 g) was stirred at room temperature overnight under hydrogen atmosphere. Then, the mixture was filtered and the filtrate was evaporated to give product. The crude product was used without further purification as Compound 106, and the yield thereof was (0.35 g, 0.91 mmol).

Scheme 16-5

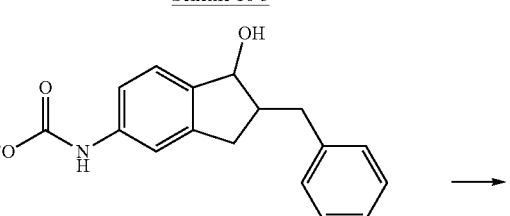
106

107

For details of the preparation of Compound 107, refer to Scheme 16-5 and the following.

3 drops of sulfuric acid was added to a solution of Compound 106 (0.35 g, 0.91 mmol) in toluene (10 mL), and then the solution was refluxed for 4 hours.

The solvent was removed under reduced pressure, and then the residue was diluted with saturated NH$_4$Cl aqueous solution and extracted with 3×20 mL of EtOAc. The combined organic layers were dried over MgSO$_4$. The crude product was used without further purification as Compound 107, and the yield thereof was 0.26 g (0.71 mmol).

Scheme 16-6

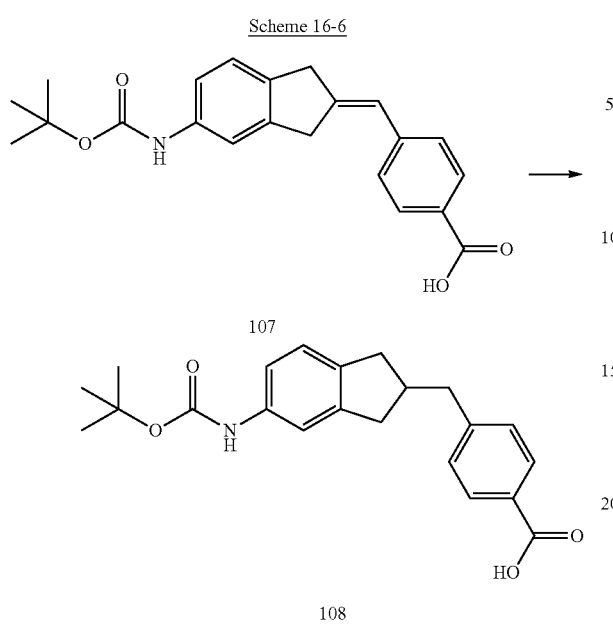

107

108

For details of the preparation of Compound 108, refer to Scheme 16-6 and the following.

A MeOH (50 mL) solution of Compound 107 (0.26 g, 0.71 mmol) and Pd—C (0.05 g) were stirred at room temperature overnight under hydrogen atmosphere. Then, the mixture was filtered and the filtrate was evaporated to give a crude product. The crude product was used without further purification as Compound 108, and the yield thereof was 0.21 g (0.57 mmol).

Scheme 16-7

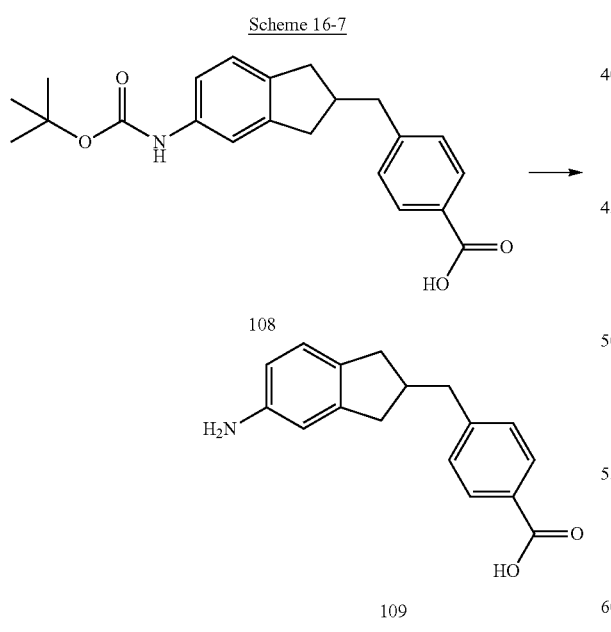

108

109

For details of the preparation of Compound 109, refer to Scheme 16-7 and the following.

4M HCl in 1,4-dioxane (5 mL) was added to the Compound 108 (0.21 g, 0.57 mmol) at 0° C. and the reaction mixture was stirred at room temperature for 3 hours. The solvent was evaporated under reduced pressure. The crude white solid was used as such for next step without further purification as Compound 109, and the yield thereof 0.14 g (0.46 mmol).

Scheme 16-8

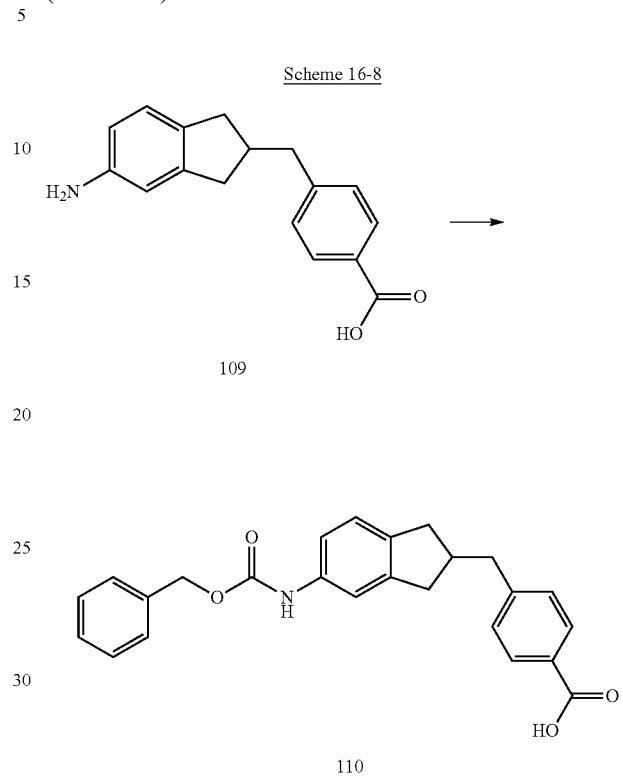

109

110

For details of the preparation of Compound 110, refer to Scheme 16-8 and the following.

A solution of 2 N NaOH (1 mL) was added to an ice-cold solution of compound 109 (0.14 g, 0.46 mmol) in 1:1 dioxane-water (10 mL) to form a mixture. This mixture was treated with benzylchloroformate (0.09 g, 0.5 mmol) and then stirred in an ice-bath for 2 hours. The reaction mixture was acidified with an aqueous solution of 1 N HCl, extracted with ethyl acetate, dried over MgSO$_4$, and concentrated in vacuo to give a solid as a crude product. The crude product was purified on a silica gel column using 1:1 hexane-EtOAc as the eluant. The resulting product was Compound 110, and the yield thereof was 32.5 mg (0.08 mmol).

110

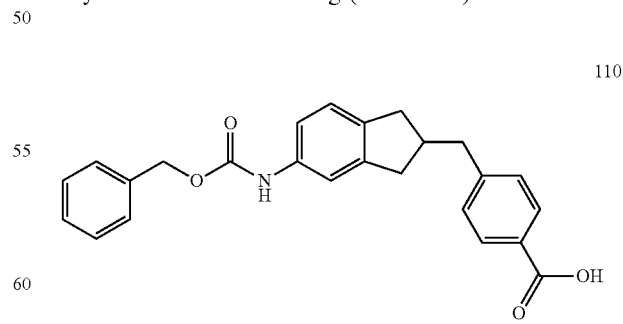

Compound 110, $^1$H-NMR (400 MHz, CDCl$_3$): δ 8.05-8.03 (d, 2H), 7.39-7.30 (m, 7H), 7.12-7.04 (m, 2H), 6.62 (s, 1H), 5.19 (s, 2H), 3.02-2.58 (m, 7H). ESI-MS m/z calcd for C$_{25}$H$_{23}$NO$_4$ 401.16, found 424.2 [M+Na]$^+$.

17. Compound 117

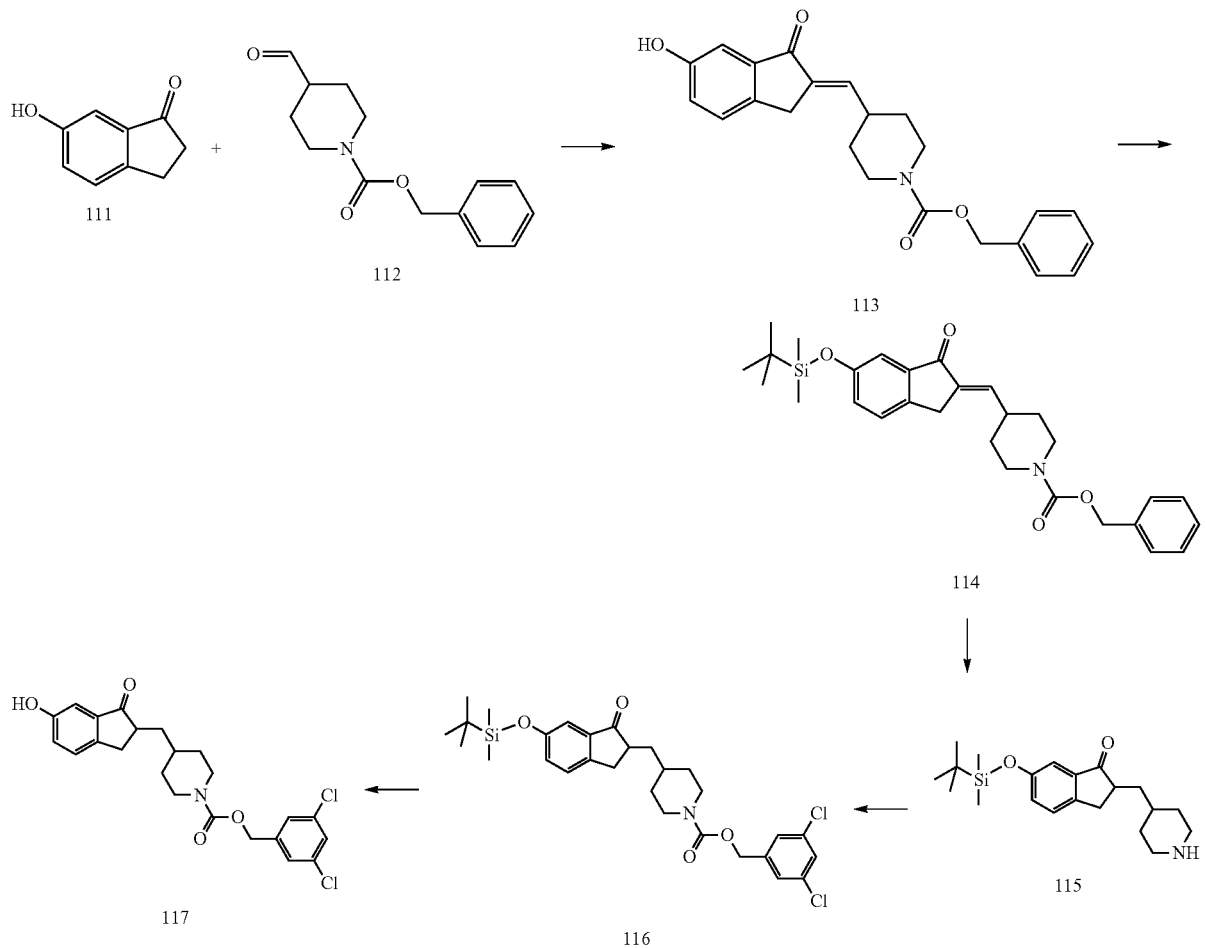

For the preparation of Compound 117, please refer to Scheme 17.

Scheme 17-1

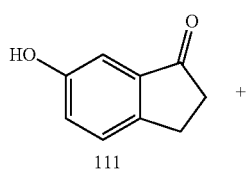

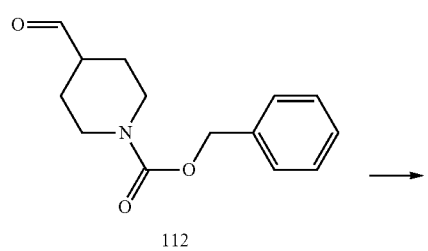

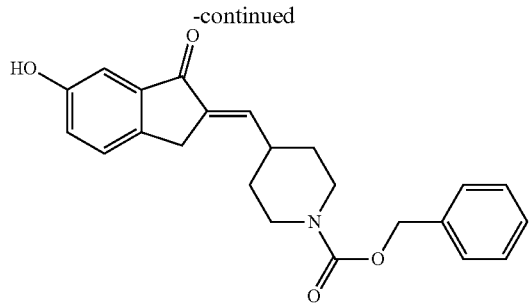

For details of the preparation of Compound 113, refer to Scheme 17-1 and the following.

1N NaOH (6.4 mL) was added to a mixture of Compound 111 (235 mg, 1.55 mmol) and Compound 112 (590 mg, 2.38 mmol) in MeOH (10.0 mL). The reaction mixture was stirred at room temperature overnight.

The solvent was removed under reduced pressure. The residue was diluted with cold water and acidified with 1N HCl, then extracted with ethyl acetate, dried over $MgSO_4$, and concentrated in vacuo to give a solid as a crude product. The crude product was Compound 113, and the yield thereof was 480 mg (1.27 mmol).

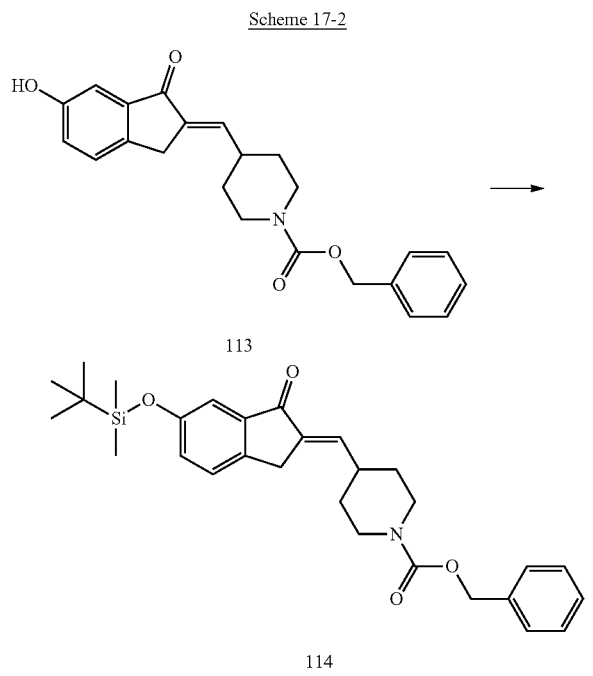

For details of the preparation of Compound 114, refer to Scheme 17-2 and the following.

Chloro-tert-butyldimethylsilane (287 mg, 1.91 mmol) was added to a mixture of Compound 113 (480 mg, 1.27 mmol) and imidazole (173 mg, 2.54 mmol) in DMF (10 mL). The reaction mixture was stirred at room temperature for 4 hours. After that, saturated NH$_4$Cl (50 mL) was added to the reaction mixture, and the precipitate solid was collected and washed with cold water. The resulting crude white solid was used without further purification as Compound 114, and the yield thereof was 482 mg (0.98 mmol).

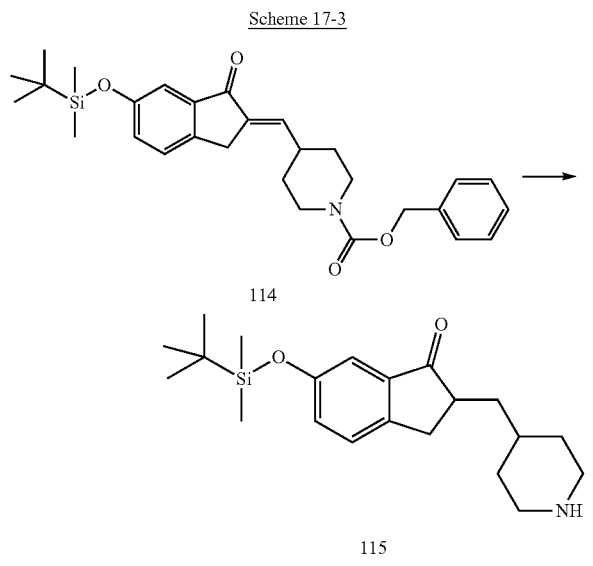

For details of the preparation of Compound 115, refer to Scheme 17-3 and the following.

A MeOH (100 mL) solution of Compound 114 (482 mg, 0.98 mmol) and Pd—C (96 mg) were stirred at room temperature overnight under hydrogen atmosphere. Then, the mixture was filtered and the filtrate was evaporated to give a crude product. The crude product was used without further purification as Compound 115, and the yield thereof was 317 mg (0.88 mmol).

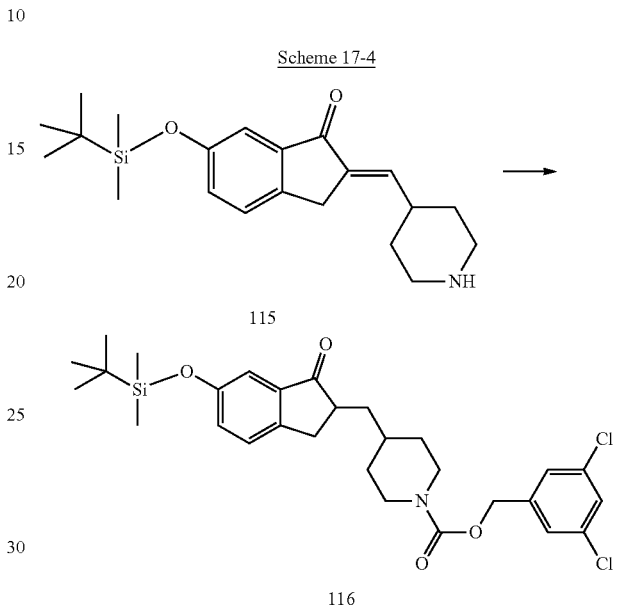

For details of the preparation of Compound 116, refer to Scheme 17-4 and the following.

Triphosgene (54 mg, 0.18 mmol) was added to a solution of 3,5-dichlorobenzyl alcohol (96 mg, 0.54 mmol) and DIPEA (70 mg, 0.54 mmol) in DCM (5 mL) at ice-bath. The reaction mixture was stirred at the same temperature for 1 hour.

A solution of Compound 115 (65 mg, 0.18 mmol) and DIPEA (70 mg, 0.54 mmol) in DCM (5 mL) was added into the reaction mixture at ice-bath. After the addition, the reaction mixture was allowed to warm to room temperature and stirred overnight.

The solvent was removed under reduced pressure, and then the residue was extracted with EA and saturated NH$_4$Cl. The combined organic layers were dried over MgSO$_4$ and concentrated in vacuo to give a solid as crude product. The crude product was used without further purification as Compound 116, and the yield thereof was 80 mg (0.14 mmol).

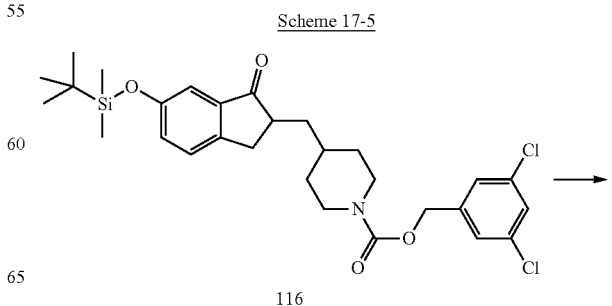

-continued

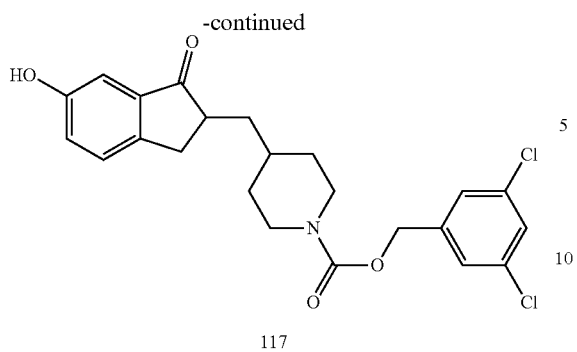

117

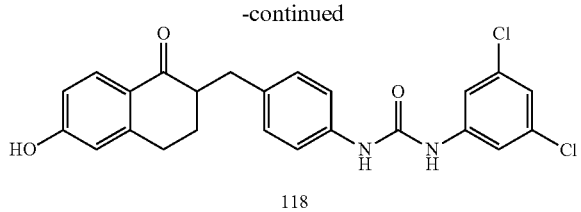

118

For details of the preparation of Compound 117, refer to Scheme 17-5 and the following.

1M TBAF (1 mL) was added to a solution of Compound 116 (80 mg, 0.14 mmol) in THF (5 mL) to form a mixture, and the mixture was stirred at room temperature for 30 minutes.

The solvent was removed under reduced pressure. The residue was extracted with EA and saturated NH$_4$Cl. The combined organic layers were dried over MgSO$_4$ and concentrated in vacuo to give a solid as a crude product. The crude product was purified on a silica gel column using 10:1 hexane-EtOAc as the eluant. The resulting product was Compound 117, and the yield thereof was 32 mg (0.07 mmol).

To a solution of 2-(4-aminobenzyl)-6-((tert-butyldimethylsilyl)oxy)-3,4-dihydronaphthalen-1(2H)-one (Compound 66, 0.08 g, 0.21 mmol) and TEA (0.04 g, 0.43 mmol) in DCM (20 mL) was added phenyl isocyanate (0.04 g, 0.23 mmol). After addition, the reaction mixture was stirred for 30 min.

After reaction was completed, the solvent was removed under reduced pressure. The residual was dissolved in THF (20 mL) and added TBAF (0.4 mL). After addition, the reaction mixture was stirred for 30 min.

After reaction was completed, the solvent was removed under reduced pressure. The residual was diluted with EtOAc, washed with Sat. NH$_4$Cl and brine. The combined organic layers were dried over MgSO$_4$ and concentrated in vacuo. The crude product was purified via flash column chromatography on a silica gel column using 10:3 Hex-EtOAc as the eluent to give the compound 118. Yield 0.08 g (0.17 mmol).

117

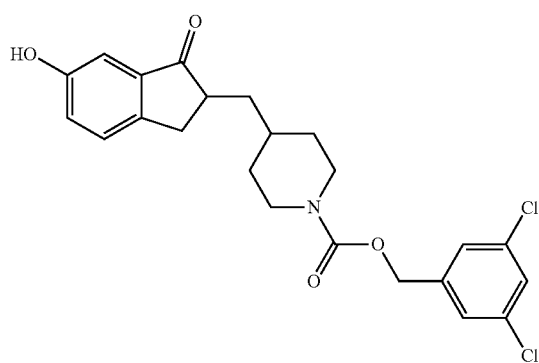

118

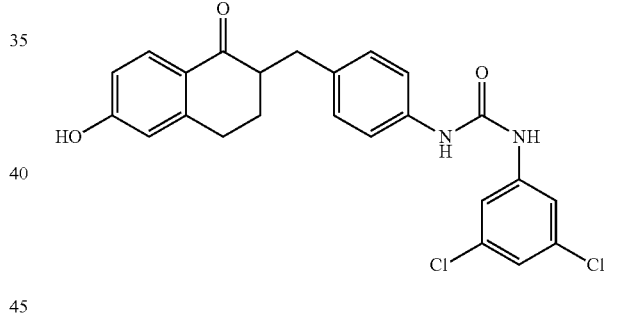

Compound 117, $^1$H-NMR (300 MHz, CDCl$_3$): δ 7.33-7.29 (m, 2H), 7.23-7.22 (m, 2H), 7.18-7.12 (m, 2H), 5.08-5.06 (d, 2H), 4.16 (br, 2H), 3.32-3.24 (m, 1H), 2.82 (br, 2H), 2.79-2.67 (m, 2H), 1.95-1.86 (m, 1H), 1.79-1.72 (m, 4H), 1.38-1.33 (m, 1H), 1.24-1.18 (m, 1H). ESI-MS m/z calcd for C$_{23}$H$_{23}$Cl$_2$NO$_4$ 447.10, found 470.20 [M+Na]$^+$.

18. Compound 118,

Compound 118, $^1$H-NMR (400 MHz, CD$_3$OD): δ 7.88-7.86 (d, 1H), 7.48-7.47 (d, 2H), 7.36-7.34 (d, 2H), 7.20-7.18 (d, 2H), 7.04-7.03 (t, 1H), 6.72-6.69 (dd, 1H), 6.61-6.60 (d, 1H), 3.29-3.28 (m, 1H), 2.94-2.84 (m, 2H), 2.82-2.66 (m, 1H), 2.08-2.01 (m, 1H), 1.77-1.67 (m, 1H), 1.57-1.51 (m, 1H). ESI-MS m/z calcd for C$_{24}$H$_{20}$Cl$_2$N$_2$O$_3$ 454.03, found 477.1 [M+Na]$^+$.

19. Compound 119

Scheme 18

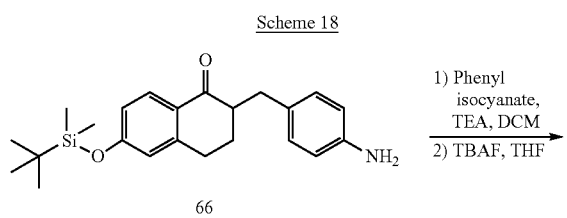

Scheme 19

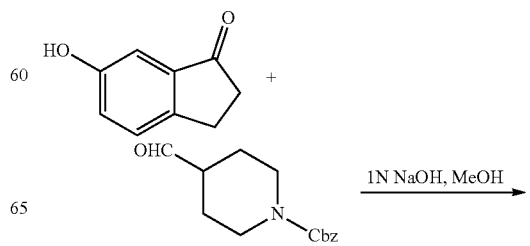

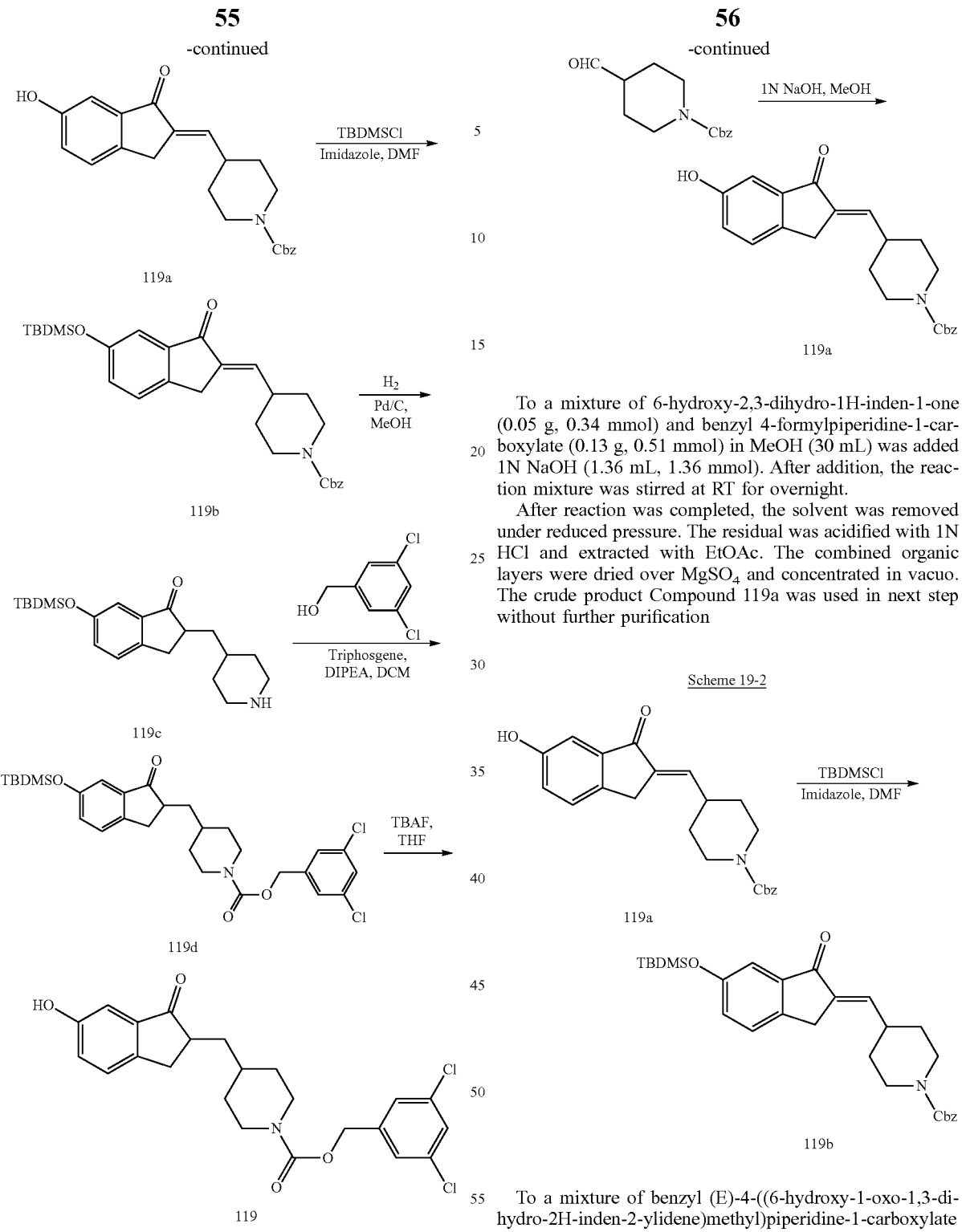

To a mixture of 6-hydroxy-2,3-dihydro-1H-inden-1-one (0.05 g, 0.34 mmol) and benzyl 4-formylpiperidine-1-carboxylate (0.13 g, 0.51 mmol) in MeOH (30 mL) was added 1N NaOH (1.36 mL, 1.36 mmol). After addition, the reaction mixture was stirred at RT for overnight.

After reaction was completed, the solvent was removed under reduced pressure. The residual was acidified with 1N HCl and extracted with EtOAc. The combined organic layers were dried over MgSO₄ and concentrated in vacuo. The crude product Compound 119a was used in next step without further purification Scheme 19-2

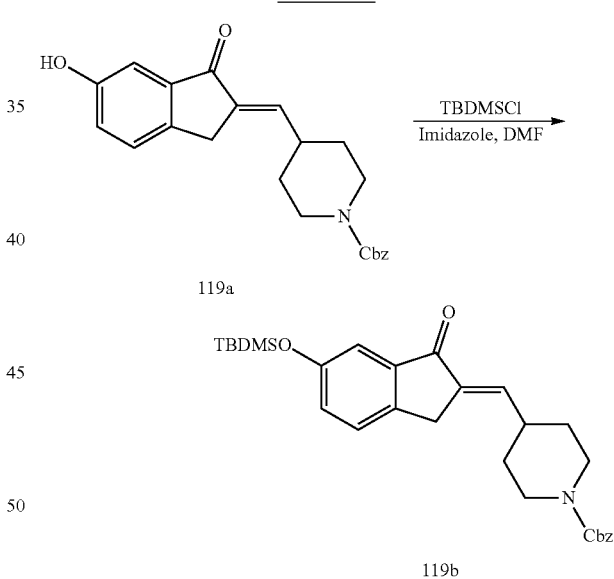

To a mixture of benzyl (E)-4-((6-hydroxy-1-oxo-1,3-dihydro-2H-inden-2-ylidene)methyl)piperidine-1-carboxylate (Compound 119a, 0.17 g, 0.45 mmol) and imidazole (0.06 g, 0.90 mmol) in DMF (5 mL) was added TBDMSCl (0.10 mL, 0.68 mmol) at 0° C. And then the reaction mixture was allowed to warm to RT and stirred for overnight.

After reaction was completed, the solvent was removed. The residual was diluted with water and extracted with EtOAc. The combined organic layers were dried over MgSO₄ and concentrated in vacuo. The crude product was purified via flash column chromatography on a silica gel column using 10:1 Hex-EtOAc as the eluent to give the compound 119b. Yield 0.11 g (0.22 mmol).

Scheme 19-3

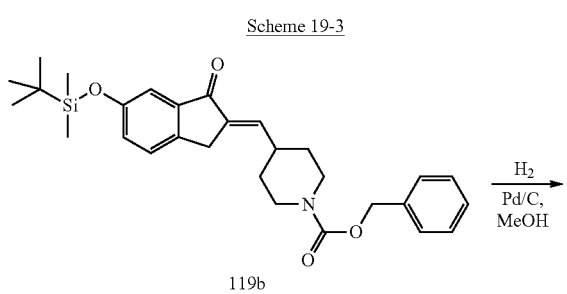

119b

119c

To a solution of benzyl (E)-4-((6-((tert-butyldimethylsilyl)oxy)-1-oxo-1,3-dihydro-2H-inden-2-ylidene)methyl)piperidine-1-carboxylate (Compound 119b, 0.11 g, 0.22 mmol) in MeOH (20 mL) was added Pd/C (0.02 g), and then the reaction mixture was stirred under $H_2$ for overnight.

After reaction was completed, the solvent was removed under reduced pressure. The residual was filtered through celite, washed with EtOAc and then concentrated in vacuo. The crude product Compound 119c was used in the next step without further purification.

Scheme 19-4

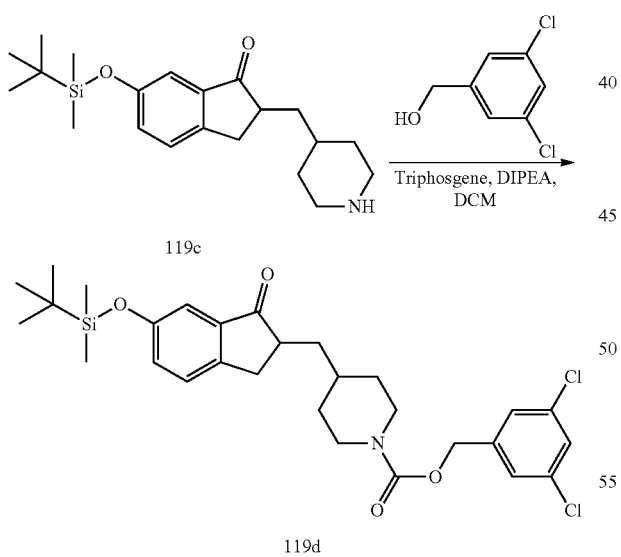

119c

119d

To a solution of (3,5-dichlorophenyl)methanol (Compound 119c, 0.09, 0.54 mmol) and DIPEA (0.07 g, 0.54 mmol) in DCM (50 mL) was added triphosgene (0.05 g, 0.18 mmol) at 0° C. After addition, the reaction mixture was stirred at the same temperature for 1 hr.

To the reaction mixture was added a solution of 6-((tert-butyldimethylsilyl)oxy)-2-(piperidin-4-ylmethyl)-2,3-dihydro-1H-inden-1-one (0.06 g, 0.18 mmol) and DIPEA (0.07 g, 0.54 mmol) in DCM (10 mL). After addition, the reaction mixture was slowly warmed to RT and stirred for overnight.

After reaction was completed, the solvent was removed under reduced pressure. The residual was diluted with water and extracted with EtOAc. The combined organic layers were dried over $MgSO_4$ and concentrated in vacuo. The crude product was purified via flash column chromatography on a silica gel column using 10:1 Hex-EtOAc as the eluent to give the compound 119d (0.08 g).

Scheme 19-5

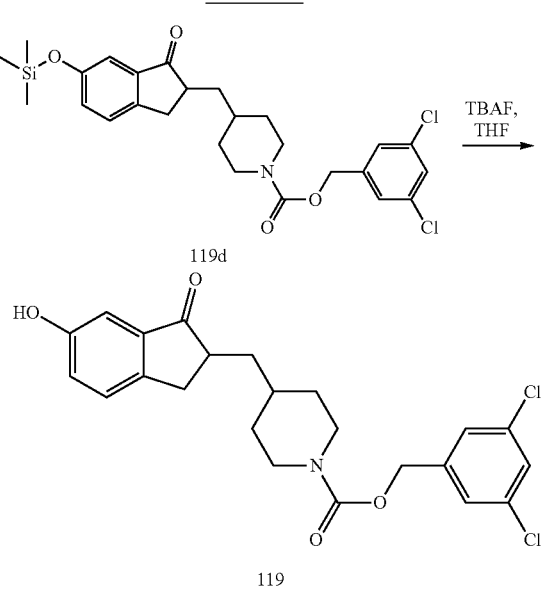

119d

119

To a solution of 3,5-dichlorobenzyl 4-((6-((tert-butyldimethylsilyl)oxy)-1-oxo-2,3-dihydro-1H-inden-2-yl)methyl)piperidine-1-carboxylate (Compound 119d, 0.08 g, 0.14 mmole) in THF (5 mL) was added TBAF (0.5 mL). After addition, the reaction mixture was stirred at RT for 30 min.

After reaction was completed, the solvent was removed under reduced pressure. The residual was diluted with water and extracted with EtOAc. The combined organic layers were dried over $MgSO_4$ and concentrated in vacuo. The crude product was purified via flash column chromatography on a silica gel column using 10:1 Hex-EtOAc as the eluent to give the compound 119. Yield 0.03 g (0.07 mmol)

Compound 119 ¹H-NMR (300 MHz, CDCl₃): δ 7.33-7.12 (m, 6H), 5.08-5.06 (d, 2H), 4.16-4.09 (m, 2H), 3.32-3.24 (m, 1H), 2.82-2.67 (m, 4H), 1.95-1.86 (m, 1H), 1.79-1.64 (m, 4H), 1.38-1.18 (m, 2H). ESI-MS m/z calcd for $C_{23}H_{23}Cl_2NO_4$ 447.10, found 470.2 [M+Na]⁺.

20. Compound 120-121, 125, and 127

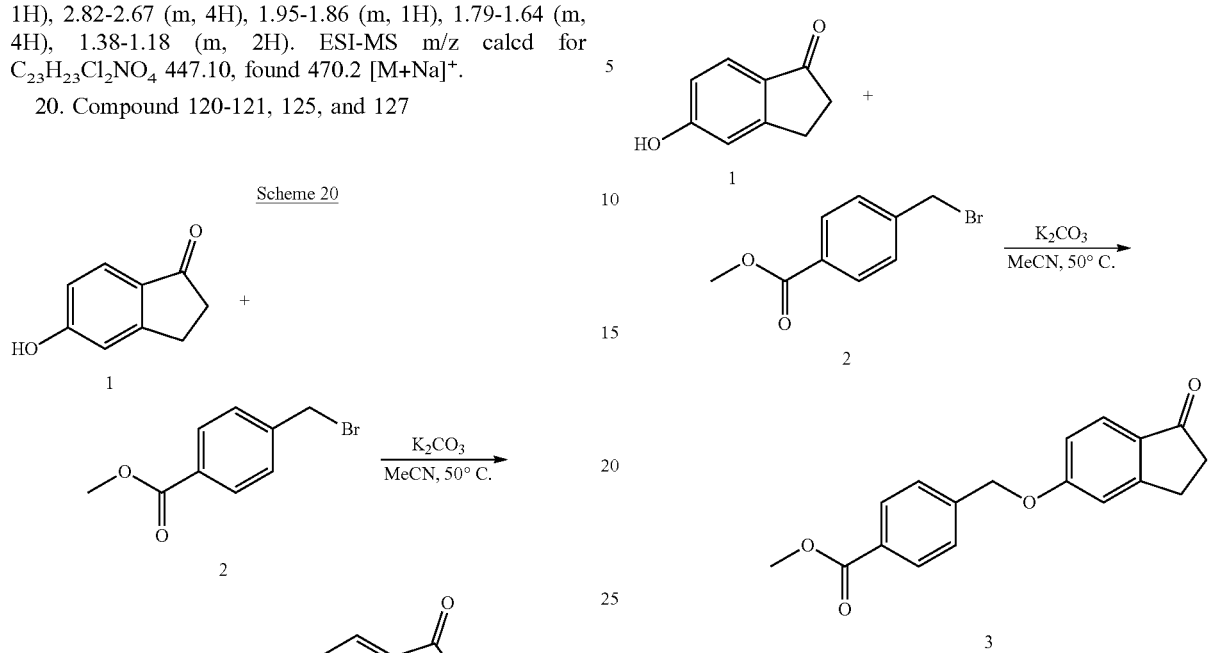

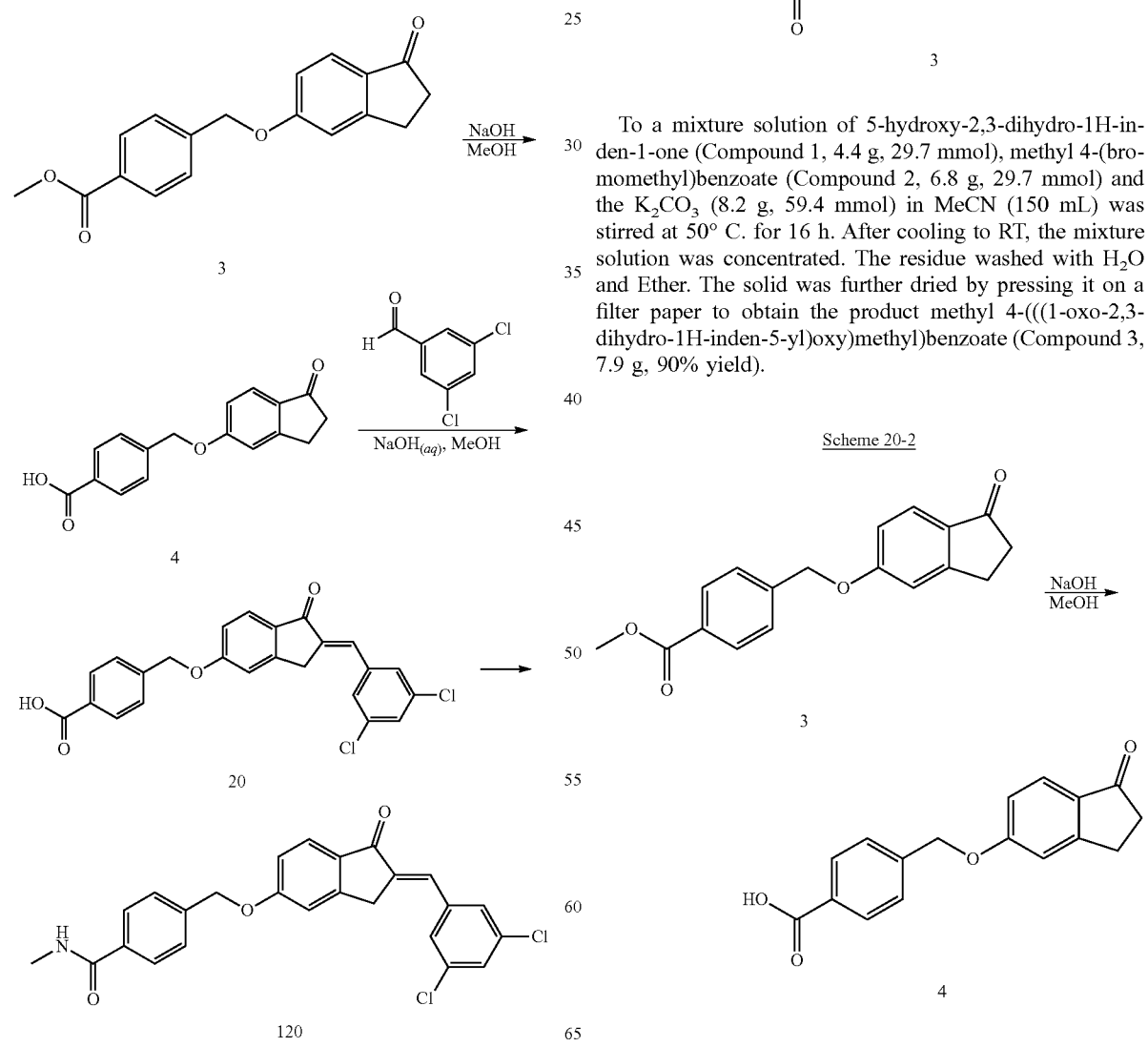

To a mixture solution of 5-hydroxy-2,3-dihydro-1H-inden-1-one (Compound 1, 4.4 g, 29.7 mmol), methyl 4-(bromomethyl)benzoate (Compound 2, 6.8 g, 29.7 mmol) and the $K_2CO_3$ (8.2 g, 59.4 mmol) in MeCN (150 mL) was stirred at 50° C. for 16 h. After cooling to RT, the mixture solution was concentrated. The residue washed with $H_2O$ and Ether. The solid was further dried by pressing it on a filter paper to obtain the product methyl 4-(((1-oxo-2,3-dihydro-1H-inden-5-yl)oxy)methyl)benzoate (Compound 3, 7.9 g, 90% yield).

To a solution of the methyl 4-(((1-oxo-2,3-dihydro-1H-inden-5-yl)oxy)methyl) benzoate (Compound 3, 7.9 g, 26.7 mmol) in the MeOH (100 mL) was added 1N NaOH solution (80 mL) at 50° C. for overnight. The reaction mixture was concentrated to remove the organic solvent. The residue was diluted with water and acidified to pH 4 with 2N HCl$_{(aq)}$. The resulting white precipitate was filtered, washed with H$_2$O and ether. The solid was further dried by pressing it on a filter paper to obtain the white powder product 4-(((1-oxo-2,3-dihydro-1H-inden-5-yl)oxy)methyl)benzoic acid (Compound 4, 7.0 g, 93% yield).

Scheme 20-3

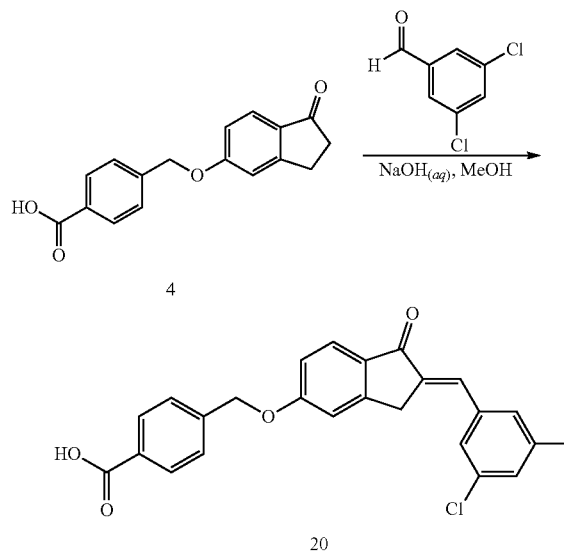

4

20

The 1N NaOH solution (560 mL) was added to a mixture of the 4-(((1-oxo-2,3-dihydro-1H-inden-5-yl)oxy)methyl) benzoic acid (Compound 4, 7.0 g, 24.8 mmol) and 3,5-dichlorobenzaldehyde (5.2 g, 29.7 mmol) in the MeOH (100 mL) at RT for 16 h. The reaction mixture was concentrated to remove the organic solvent. The residue was diluted with water and acidified to pH 4 with 2N HCl(aq). The resulting white precipitate was filtered, washed with H$_2$O and ether, and dried by pressing it on a filter paper to obtain the product as a powder to provide crude product as a solid (12.2 g). The crude product was added the co-solvent of MeOH:Toluene=1:6 and stirred at 60° C. for 4 h. When the temperature cooling to r.t the mixture filtered and washed with H$_2$O and ether. The solid was further dried by pressing it on a filter paper to obtain the product (E)-4-(((2-(3,5-dichlorobenzylidene)-1-oxo-2,3-dihydro-1H-inden-5-yl)oxy)methyl) benzoic acid as a white powder (Compound 20, 7.1 g, 65% yield).

Scheme 20-4

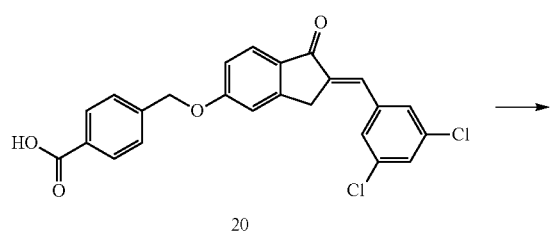

20

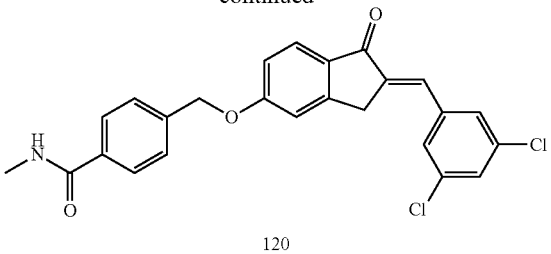

120

To a mixture solution of the (E)-4-(((2-(3,5-dichlorobenzylidene)-1-oxo-2,3-dihydro-1H-inden-5-yl)oxy)methyl) benzoic acid (Compound 20, 100.0 mg, 0.23 mmol) DMAP (56.2 mg, 0.46 mmol) and EDCI (52.9 mg, 0.35 mmol) in DCM was added the solution of 2M Methylamine in THF (0.3 mL) and stirred for overnight. After the reaction completed, the Hexane was added to separate out the white solid which was filtered, washed with H$_2$O and ether to obtain the product as a white solid product Compound 120. Yield (72.0 mg, 69% yield).

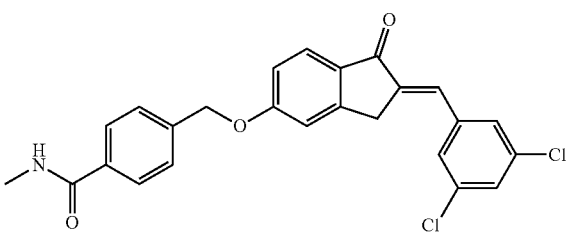

120

Compound 120 $^1$H-NMR (300 MHz, DMSO): δ 8.51 (s, 1H), 7.89-7.69 (m, 6H), 7.58-7.55 (d, 2H), 7.43 (s, 1H), 7.33 (s, 1H), 7.14-7.11 (d, 1H), 5.32 (s, 2H), 4.12 (s, 2H), 2.79 (s, 3H). ESI-MS m/z calcd for C$_{25}$H$_{19}$Cl$_2$NO$_3$ 451.07, found 474.3 [M+Na]$^+$.

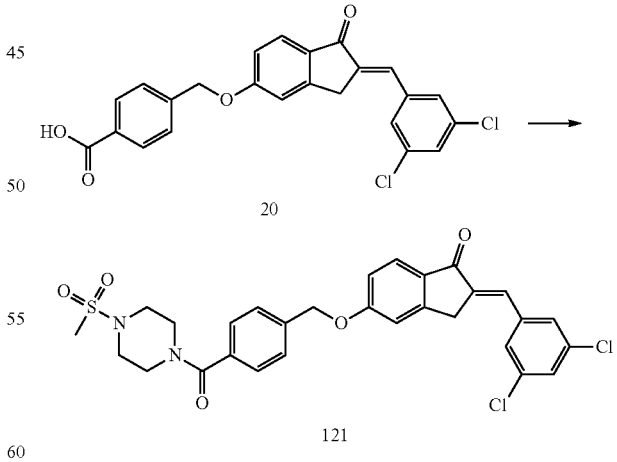

To a mixture solution of the (E)-4-(((2-(3,5-dichlorobenzylidene)-1-oxo-2,3-dihydro-1H-inden-5-yl)oxy)methyl) benzoic acid (Compound 20, 100.0 mg, 0.23 mmol) DMAP (56.2 mg, 0.46 mmol) EDCI (52.9 mg, 0.35 mmol) and 1-(Methylsulfonyl) piperazine (45.3 mg, 0.28 mmol) in DCM was stirred for overnight. After the reaction completed, the crude extracted with NH₄OH and DCM. The combined organics were dried over MgSO₄ and concentrated. The residue was purify with Silica gel (EA only (20 mL) then DCM:MeOH=1:8) to obtain the Compound 121 (80.0 mg, 59% yield).

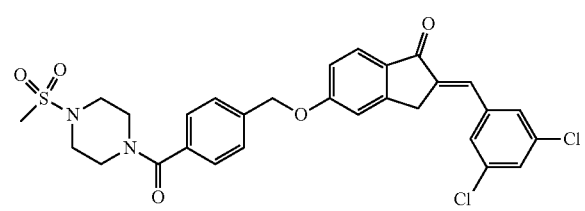

121

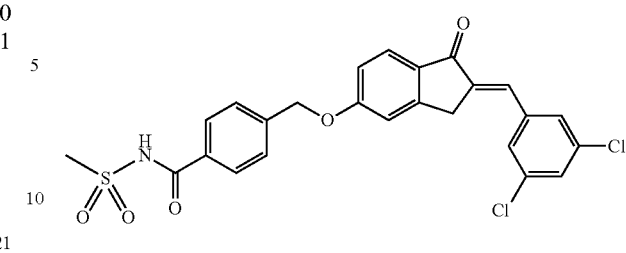

125

Compound 125 ¹H-NMR (300 MHz, DMSO): δ 7.99-7.96 (d, 2H), 7.81 (s, 2H), 7.77-7.74 (d, 1H), 7.69 (s, 1H), 7.60-7.57 (m, 2H), 7.42 (s, 1H), 7.32 (s, 1H), 7.15-7.12 (dd, 1H), 5.35 (s, 2H), 4.12 (s, 2H), 3.33 (s, 3H). ESI-MS m/z calcd for C₂₅H₁₉Cl₂NO₅S 515.04, found 516.3 [M+H]⁺

Compound 121 ¹H-NMR (300 MHz, DMSO): δ7.82 (s, 2H), 7.77-7.75 (d, 1H), 7.69 (s, 1H), 7.59-7.57 (d, 2H), 7.49-7.46 (d, 2H), 7.43 (s, 1H), 7.34 (s, 1H), 7.15-7.12 (d, 1H), 5.31 (d, 2H), 4.13 (d, 2H), 3.70-3.45 (br, 4H), 3.17-3.15 (br, 4H), 2.90 (s, 3H). ESI-MS m/z calcd for C₂₉H₂₆Cl₂N₂O₅S 584.09, found 607.4 [M+Na]⁺.

Compound 125 and 127 were synthesized by using the same method as in Scheme 20-4.

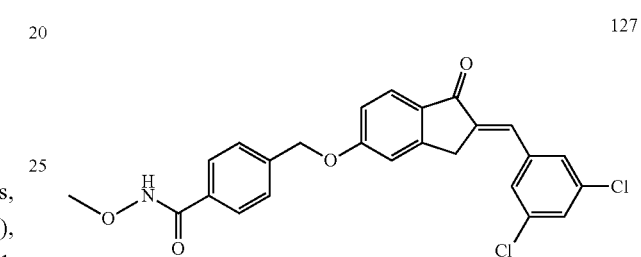

127

Compound 127 ¹H-NMR (300 MHz, DMSO): δ 7.81-7.69 (m, 7H), 7.59-7.56 (d, 2H), 7.42 (s, 1H), 7.32 (s, 1H), 7.14-7.10 (d, 1H), 5.76 (s, 2H), 4.12 (s, 2H), 3.71 (s, 3H). ESI-MS m/z calcd for C₂₅H₁₉Cl₂NO₄ 467.03, found 468.3 [M+H]⁺

21. Compound 122-124, 126 and 130

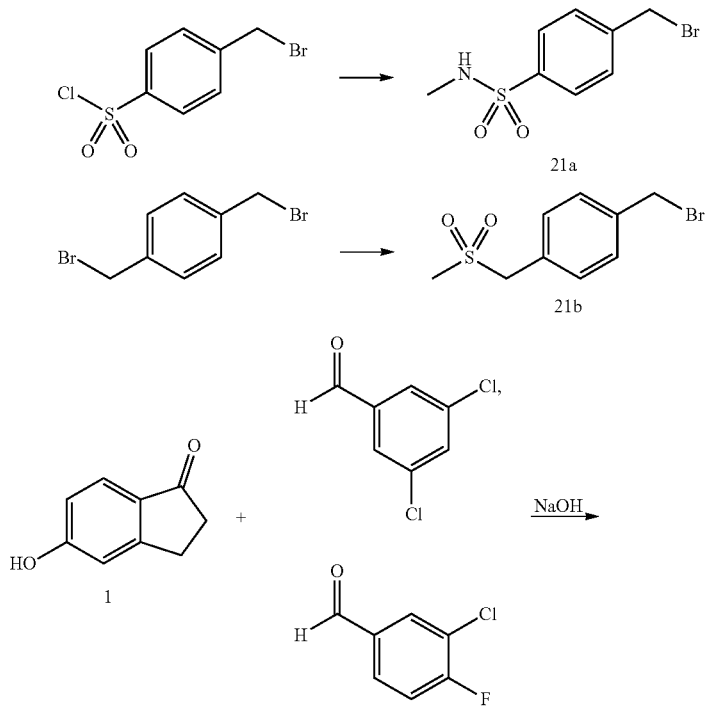

Scheme 21

-continued
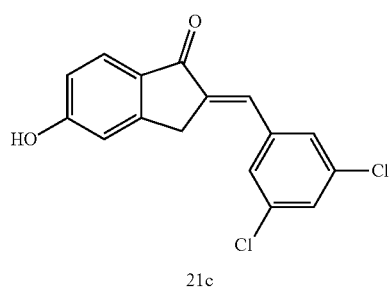
21c
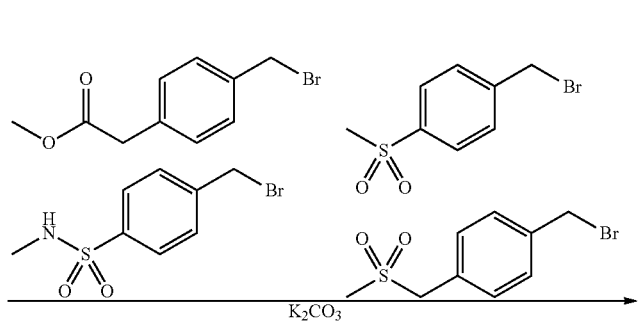
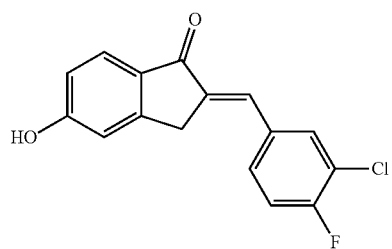
126a
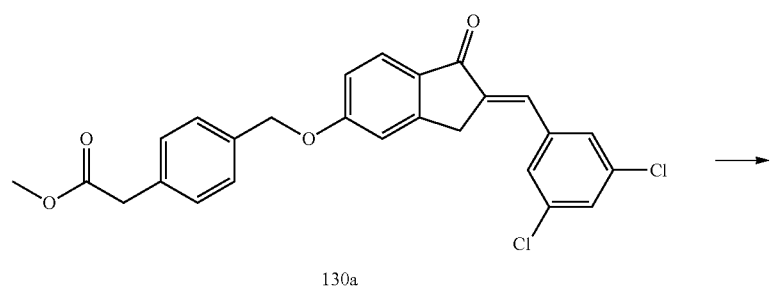
130a
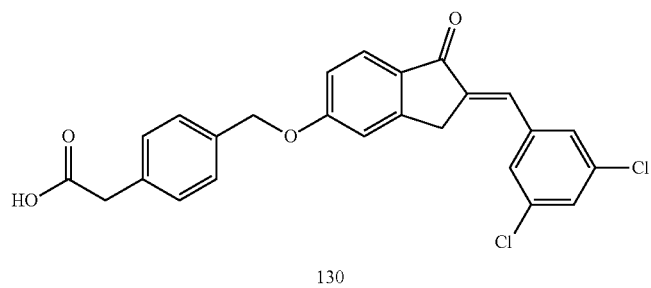
130
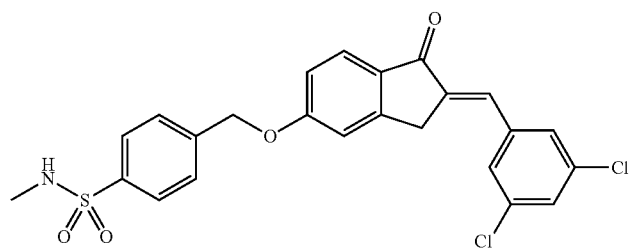
123

-continued

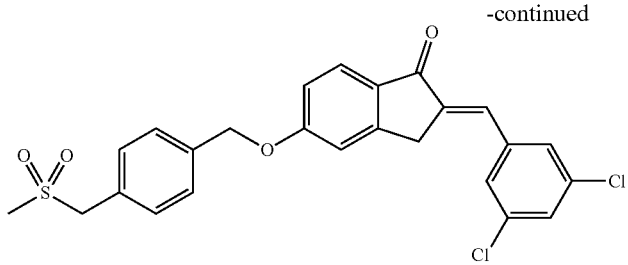

124

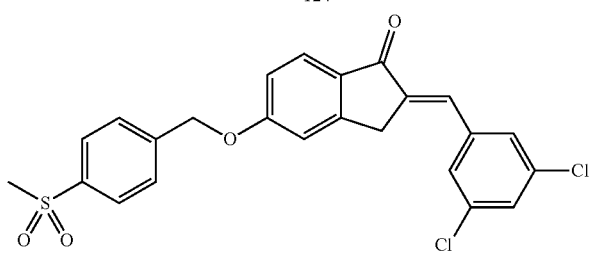

122

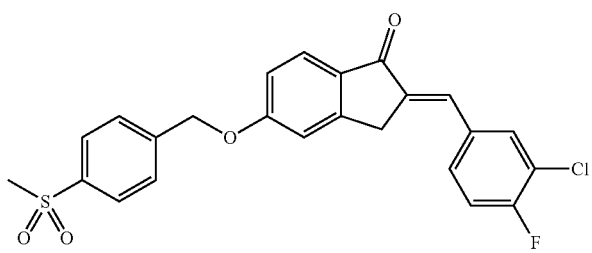

126

Scheme 21-1

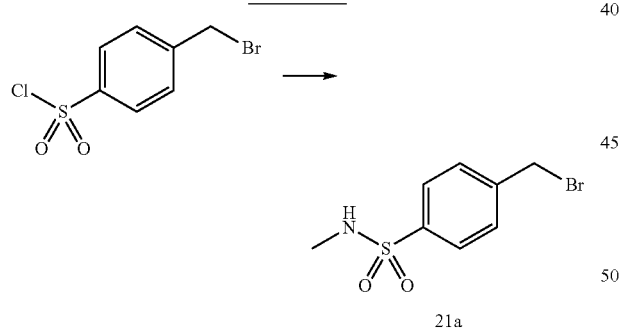

21a

Scheme 21-2

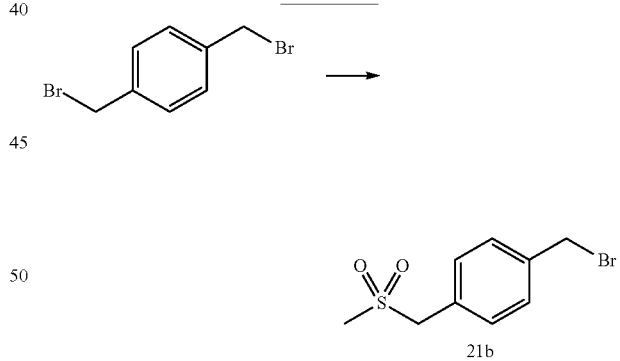

21b

Mix 4-(bromomethyl)benzenesulfonyl chloride (2.7 g, 10 mmol), anhydrous potassium carbonate (1.4 g, 10 mmol) and anhydrous THF (60 mL) under nitrogen. Cool the mixture in an ice bath, add dropwise a 2M solution of methylamine in THF, and stir at this temperature for 30 min. Remove the ice bath and stir at ambient temperature for 16 h. Dilute with EtOAc then wash with 1N aqueous HCl. Separate the organic layer, dry over $Na_2SO_4$ and concentrate in vacuo. The crude product was purified via flash column chromatography on a silica gel column using 1:0, 4:1, 7:3 and 13:7 Hex-EtOAc as the eluent to give Compound 21a, 4-Bromomethyl-N-methyl-benzenesulfonamide. Yield (1.5 g, 71%).

The 1,4-bis (bromomethyl) benzene (3.10 g, 11.75 mmol) and sodium methylsulfinate (0.40 g, 3.92 mmol) was dissolved in DMF (5 mL) and the reaction was warmed to 80 deg.] C. for 6 hours after cooling to room temperature, and then thereto was added water (20 mL), and extracted with ethyl acetate (20 mL×3). The combined organic phases were dried over anhydrous sodium sulfate, filtered, and concentrated under reduced pressure. The crude product was purified via flash column chromatography on a silica gel column using 2:1 petroleum ether-EtOAc as the eluent to give the Compound 21b as a white solid 1-(bromomethyl)-4-((methylsulfone) methyl) benzene (1.4 g, 60.0%).

Scheme 21-3
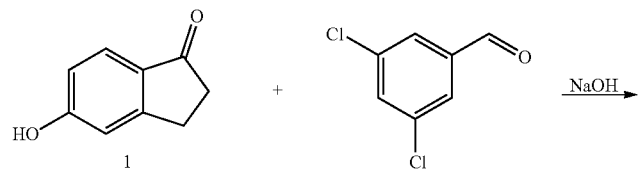
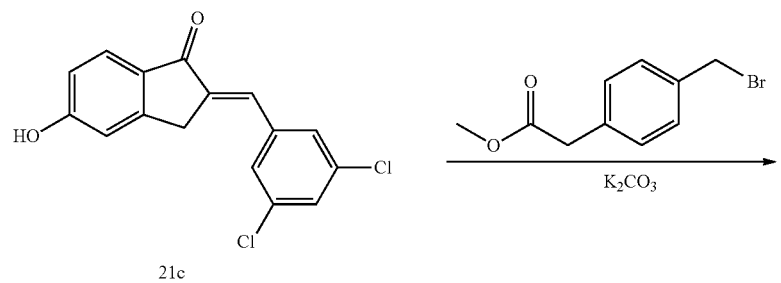
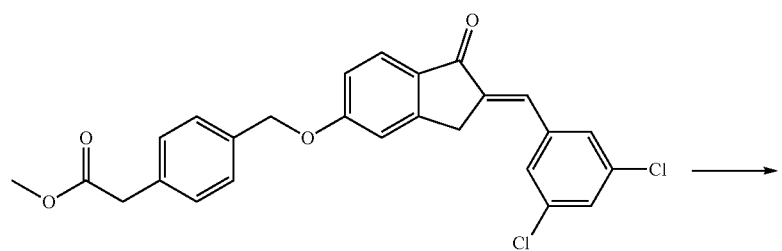
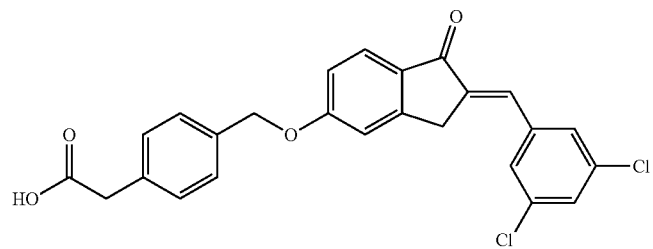

Scheme 21-3a

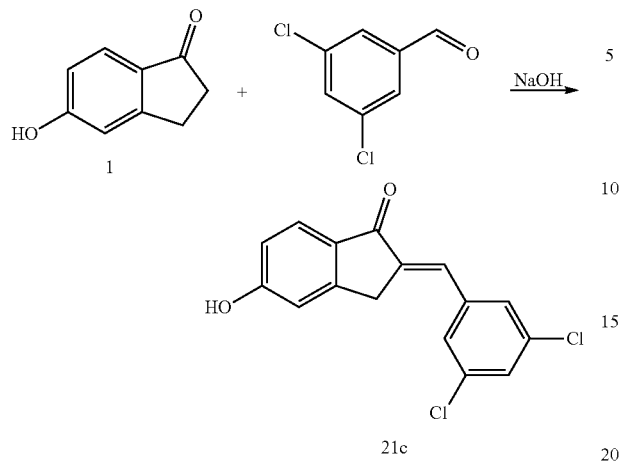

To a solution of 5-hydroxyindanone (Compound 1, 500.0 mg, 3.4 mmol) and 3,5-Dichlorobenz-aldehyde (650.0 mg, 3.7 mol) in MeOH (20 mL) was added 1N NaOH (10 mL). The solution was stirred at RT for overnight. The reaction mixture was concentrated. The residue washed with $H_2O$ and Ether. The solid was further dried by pressing it on a filter paper to obtain the product as a powder. The product Compound 21c, (E)-2-(3,5-dichlorobenzylidene)-5-hydroxy-2,3-dihydro-1H-inden-1-one, was used without further purification (1.02 g, 98% yield).

Scheme 21-3b

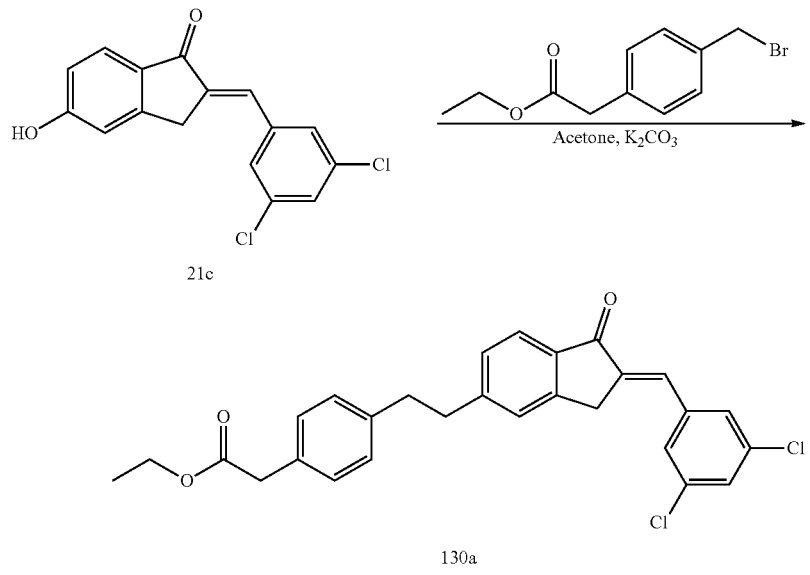

To a mixture of (E)-2-(3,5-dichlorobenzylidene)-5-hydroxy-2,3-dihydro-1H-inden-1-one (0.45 g, 1.47 mmol) and $K_2CO_3$ in acetone (30 mL) was added ethyl 2-(4-(bromomethyl)phenyl)acetate (0.43 g, 1.67 mmol). After addition, the reaction mixture was refluxed for overnight.

After reaction was completed, the solvent was removed under reduced pressure. The residual was diluted with water, then collected precipitated solid by filtration. The crude precipitated solid was recrystallized from toluene to obtain the product Compound 130a, and then used in the next step without further purification. Yield 0.45 g (0.96 mmol)

Scheme 21-3c

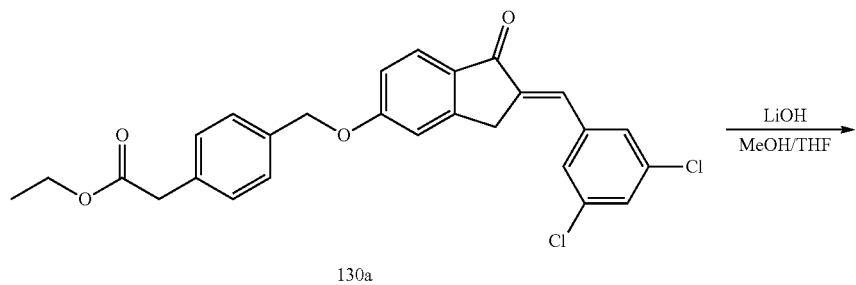

The ethyl (E)-2-(4-(((2-(3,5-dichlorobenzylidene)-1-oxo-2,3-dihydro-1H-inden-5-yl)oxy)methyl)phenyl)acetate (Compound 130a, 0.12 g, 0.25 mmol) was dissolved in MeOH/THF (10 mL, 1:1) and 1N LiOH 1.5 mL was added to the reaction mixture and stirred at RT for overnight.

After reaction was completed, the solvent was removed under reduced pressure. The residual was acidified with 1N HCl and the precipitated solid was collected by filtration. The crude product was purified via flash column chromatography on a silica gel column using 10:1 EtOAc-MeOH as the eluent to obtain the product Compound 130. Yield 2.6 mg (0.005 mmol)

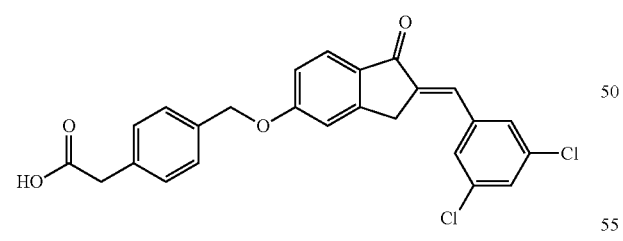

130

Compound 130 $^1$H-NMR (300 MHz, CDCl$_3$): δ7.87-7.84 (d, 1H), 7.49-7.48 (d, 2H), 7.44-7.31 (m, 6H), 7.06-7.03 (m, 2H), 5.17 (s, 2H), 3.97 (s, 2H), 3.68 (s, 2H). ESI-MS m/z calcd for C$_{25}$H$_{18}$Cl$_2$O$_4$ 452.06, found 475.0 [M+Na]$^+$ Compound 122-124 and 126 were synthesized by using the same methods as in Scheme 21.

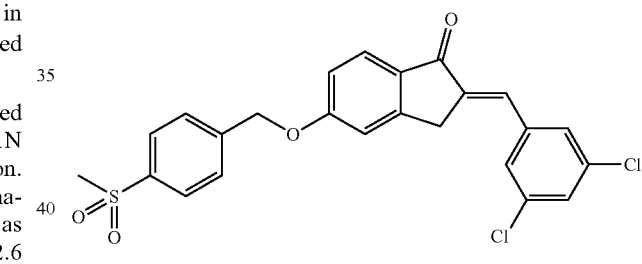

122

Compound 122 $^1$H-NMR (300 MHz, DMSO): δ7.98-7.97 (d, 2H), 7.81 (s, 2H), 7.77-7.71 (m, 3H), 7.69 (s, 1H), 7.42 (s, 1H), 7.34 (s, 1H), 7.18-7.13 (d, 1H), 5.37 (s, 2H), 4.13 (s, 2H), 3.23 (s, 3H). ESI-MS m/z calcd for C$_{24}$H$_{18}$Cl$_2$O$_4$S 472.03, found 495.3 [M+Na]$^+$.

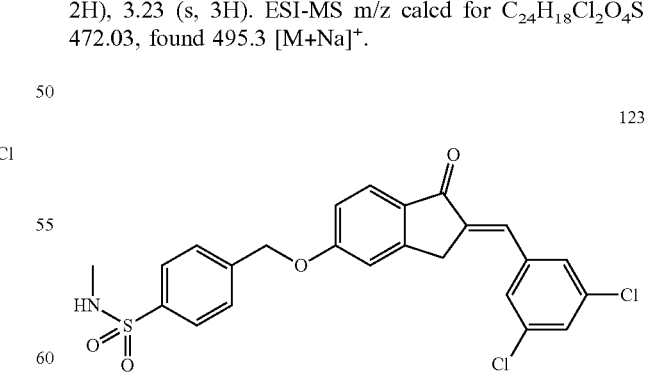

123

Compound 123 $^1$H-NMR (400 MHz, DMSO): δ7.83-7.81 (m, 4H), 7.76 (d, 1H), 7.72-7.69 (m, 3H), 7.50 (s, 1H), 7.43 (m, 1H), 7.34 (m, 1H), 7.14 (dd, 1H), 5.38 (s, 2H), 4.13 (s, 2H), 2.42 (s, 3H). ESI-MS m/z calcd for C$_{24}$H$_{19}$Cl$_2$NO$_4$S 487.04, found 488.3 [M+H]$^+$

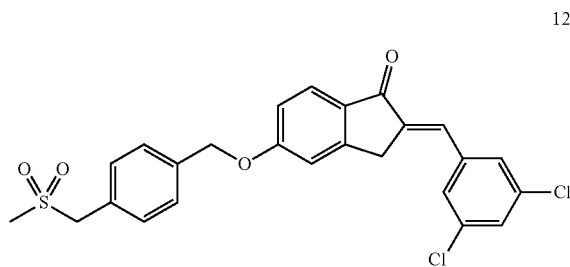
124
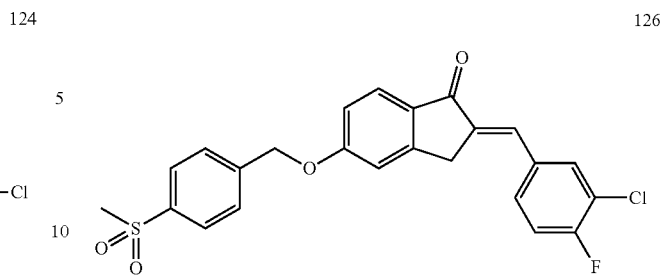
126
Compound 124 ¹H-NMR (300 MHz, DMSO): δ 7.82 (s, 2H), 7.76-7.73 (d, 1H), 7.69 (s, 1H), 7.54-7.42 (m, 5H), 7.39 (s, 1H), 7.18-7.14 (d, 1H), 5.27 (s, 2H), 4.51 (s, 2H), 4.13 (s, 2H), 2.92 (s, 3H). ESI-MS m/z calcd for $C_{25}H_{20}Cl_2O_4S$ 486.05, found 487.3 [M+H]⁺
Compound 126 ¹H-NMR (300 MHz, DMSO): δ 8.01-7.96 (m, 3H), 7.81-7.74 (m, 4H), 7.58-7.52 (m, 1H), 7.44 (s, 1H), 7.30 (s, 1H), 7.16-7.12 (d, 1H), 5.41 (s, 2H), 4.09 (s, 2H), 3.23 (s, 3H). ESI-MS m/z calcd for $C_{24}H_{18}ClFO_4S$ 456.06, found 479.3 [M+Na]⁺
22. Compound 128-129, and 132
Scheme 22
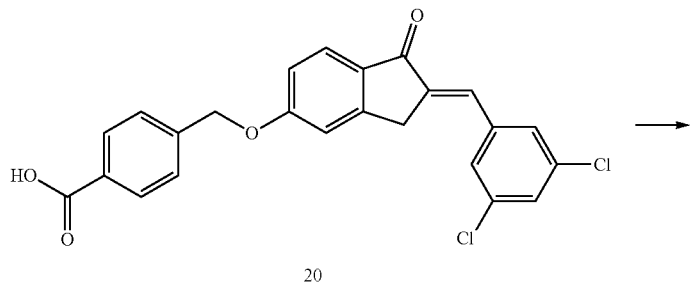
20
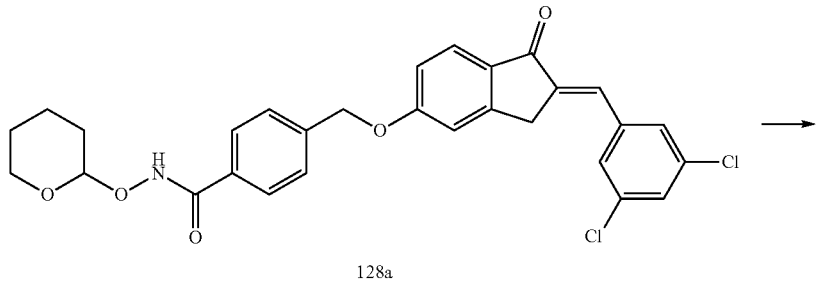
128a
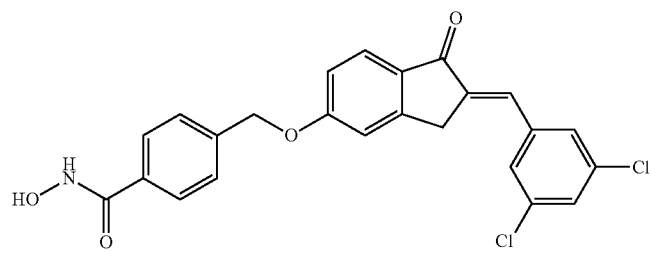
128

To a mixture solution of the (E)-4-(((2-(3,5-dichlorobenzylidene)-1-oxo-2,3-dihydro-1H-inden-5-yl)oxy)methyl)benzoic acid (Compound 20, 100.0 mg, 0.23 mmol) DMAP (56.2 mg, 0.46 mmol) EDCI (52.9 mg, 0.35 mmol) and O-(tetrahydro-2H-pyran-2-yl)hydroxylamine (29.3 mg, 0.25 mmol) in DCM was stirred for overnight. After the reaction completed, the crude extracted with NH₄OH and DCM. The combined organics were dried over MgSO₄ and concentrated. The crude product was purified via flash column chromatography on a silica gel column using 1:1 Hex-EtOAc as the eluent to give the Compound 128a. Yield (100.0 mg, 81% yield).

To a mixture solution of the (E)-4-(((2-(3,5-dichlorobenzylidene)-1-oxo-2,3-dihydro-1H-inden-5-yl)oxy)methyl)-N-((tetrahydro-2H-pyran-2-yl)oxy)benzamide (Compound 128a, 28.0 mg, 0.05 mmol) was added 2N HCl in ether (3 mL) and stirred at r.t for overnight. After the reaction was completed, the mixture was concentrated and washed with ether. The solid was further dried by pressing it on a filter paper to give the product Compound 128 as a white powder. Yield (6.0 mg, 26% yield).

128

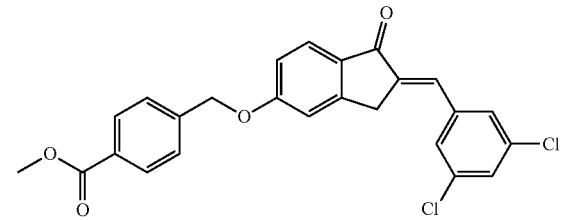

132

Compound 132 $^1$H-NMR (300 MHz, DMSO): δ8.02-7.99 (d, 2H), 7.80 (s, 2H), 7.76-7.74 (d, 1H), 7.68 (s, 1H), 7.67-7.61 (d, 2H), 7.42 (s, 1H), 7.32 (s, 1H), 7.15-7.11 (d, 1H), 5.37 (s, 2H), 4.11 (s, 2H), 3.86 (s, 3H). ESI-MS m/z calcd for $C_{25}H_{18}Cl_2O_4$ 452.06, found 453.0 [M+H]$^+$ 23. Compound 131

Compound 128 $^1$H-NMR (400 MHz, DMSO): δ 9.15 (br, 1H), 7.81-7.74 (m, 6H), 7.69 (s, 1H), 7.57-7.55 (d, 2H), 7.42 (s, 1H), 7.32 (s, 1H), 7.14-7.11 (d, 1H), 5.32 (s, 2H), 4.12 (s, 2H). ESI-MS m/z calcd for $C_{24}H_{17}Cl_2NO_4$ 453.05, found 454.3 [M+H]$^+$ Compound 129 was synthesized by using the same method as in Scheme 20-3.

129

Compound 129 $^1$H-NMR (300 MHz, DMSO): δ8.10-7.90 (m, 5H), 7.75-7.72 (d, 1H), 7.60-7.58 (d, 2H), 7.51 (s, 1H), 7.32 (s, 1H), 7.12-7.10 (d, 1H), 5.34 (s, 2H), 4.12 (s, 2H). ESI-MS m/z calcd for $C_{25}H_{16}ClF_3O_4$ 472.07, found 473.1 [M+H]$^+$ Compound 132 was synthesized by using the same method as in Scheme 12.

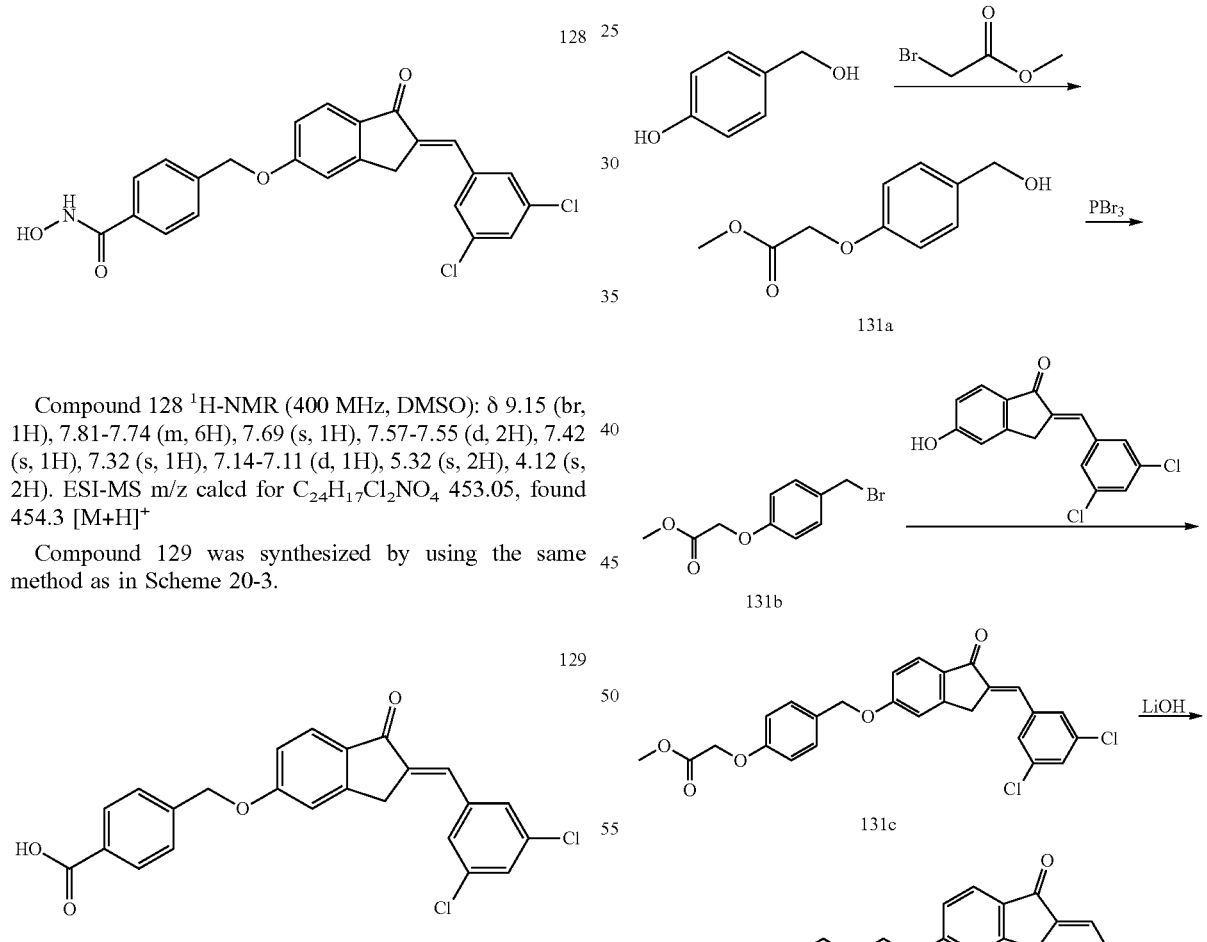

Scheme 23-1

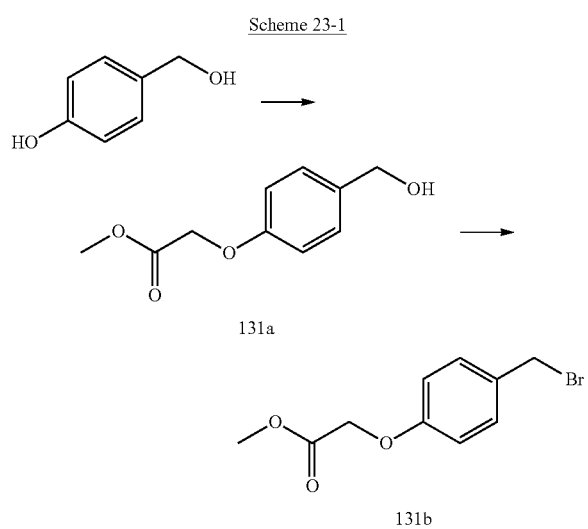

To a mixture solution of the 4-hydroxybenzenemethanol (1.0 g, 8.06 mmol), Methyl bromoacetate (1.36 g, 8.86 mmol) and the K₂CO₃ (2.22 g, 16.1 mmol) in Acetone (30 mL) was stirred at 50° C. for 16 h. After cooling to RT, the mixture solution was concentrated. The residue extracted with EA and H₂O. The combined organics were dried over MgSO₄ and concentrated to obtain the product methyl 2-(4-(hydroxymethyl)phenoxy)acetate (Compound 131a) which without further purification (1.04 g, 66% yield).

To a solution of methyl 2-(4-(hydroxymethyl)phenoxy)acetate (Compound 131a, 1.04 g, 5.3 mmol) in DCM was added the solution of PBr₃ in ether at 0° C. and stirred for 40 min at r.t, After the reaction completed, the reaction mixture was quenched by H₂O and extracted with EA and brine. The combined organics were dried over MgSO₄ and concentrated to obtain the product methyl 2-(4-(bromomethyl)phenoxy)acetate (Compound 131b) which without further purification (1.25 g, 91% yield).

Scheme 23-2

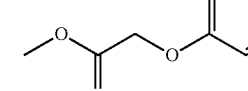

To a mixture solution of the (E)-2-(3,5-dichlorobenzylidene)-5-hydroxy-2,3-dihydro-1H-inden-1-one (100.0 mg, 1.0 mmol), methyl 2-(4-(bromomethyl)phenoxy)acetate (Compound 131b, 157.0 mg, 1.0 mmol) and the K₂CO₃ (141.0 mg, 2.0 mmol) in ACN (10 mL) was stirred at 50° C. for 16 h. After cooling to RT, the mixture solution was concentrated. The residue purify with the silica jel column (EA:Hex.=1:4) to obtain the product Compound 131c (171.0 mg, 70% yield).

Scheme 23-3

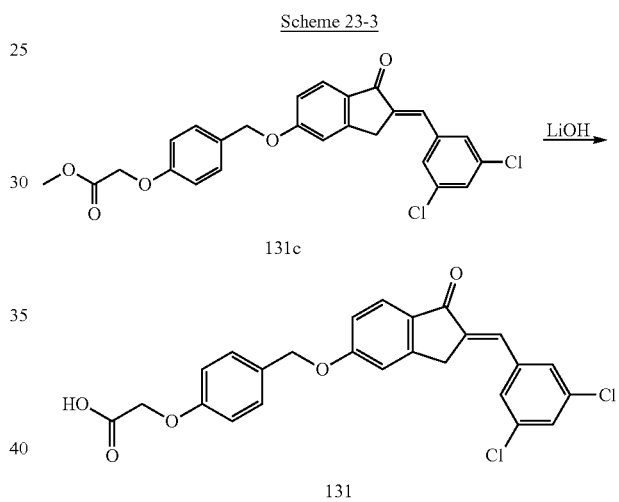

To a solution of the methyl (E)-2-(4-(((2-(3,5-dichlorobenzylidene)-1-oxo-2,3-dihydro-1H-inden-5-yl)oxy) methyl)phenoxy)acetate (Compound 131c, 100.0 mg, 0.21 mmol) in THF (3 mL) was added 1N LiOH (1 mL) and stirred at r.t for 30 min. After the reaction completed, the mixture solution was concentrated. The residue adjusted the pH=4 and filtrated. The collecting solid washed with ether and H₂O to obtain the product Compound 131 (4.0 mg, 4% yield).

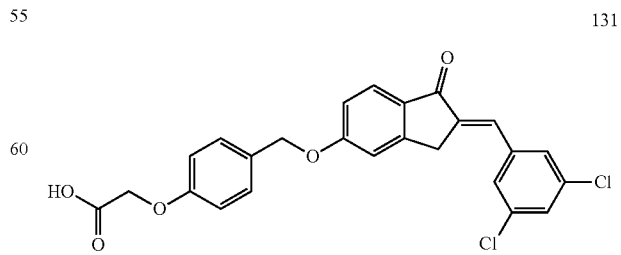

Compound 131 ¹H-NMR (400 MHz, DMSO): δ7.81 (s, 2H), 7.75-7.72 (d, 1H), 7.69 (s, 1H), 7.43-7.41 (m, 3H), 7.32

(s, 1H), 7.11-7.09 (d, 1H), 6.95-6.93 (d, 2H), 5.17 (s, 2H), 4.69 (s, 2H), 4.12 (s, 2H). ESI-MS m/z calcd for $C_{25}H_{18}Cl_2O_5$ 468.05, found 491.0 $[M+Na]^+$ 24. Compound 133

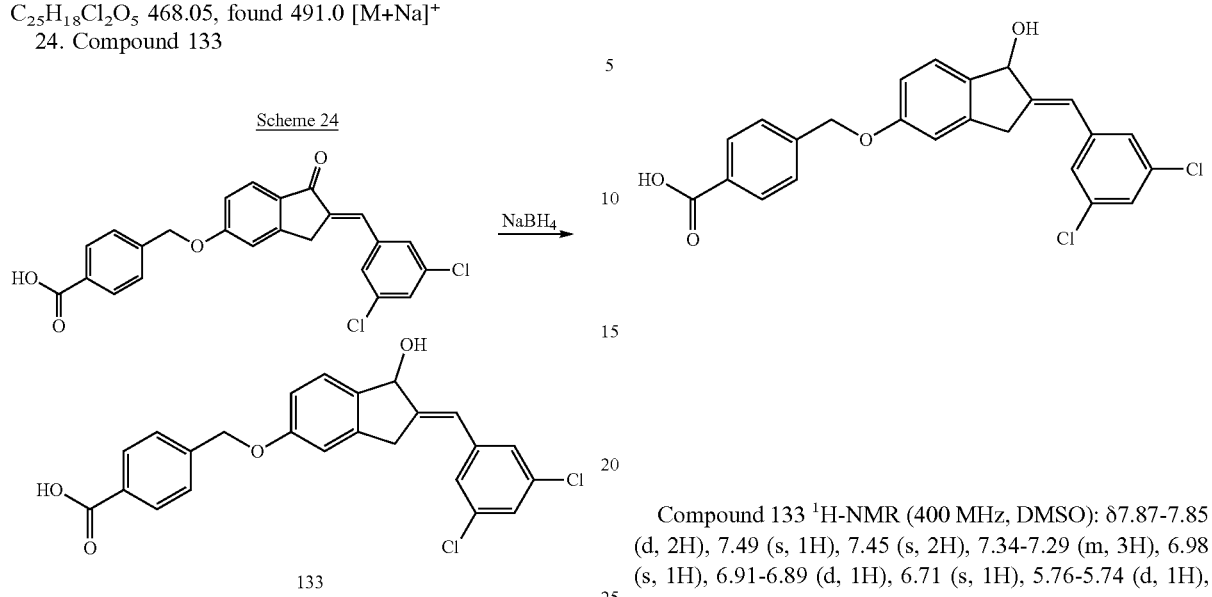

Scheme 24

To a solution of the (E)-4-(((2-(3,5-dichlorobenzylidene)-1-oxo-2,3-dihydro-1H-inden-5-yl)oxy)methyl)benzoic acid (100.0 mg, 0.23 mmol) in the co-solvent of THF/MeOH (2 mL, 1:1) was added $NaBH_4$ (50.0 mg) and stirred at 50° C. for 2 h. After the reaction was completed, the reaction mixture was cooled to room temperature and quenched by $H_2O$ at 0° C. (2 mL). The resulting white precipitate was filtered, washed with $H_2O$ and ether. The solid was further dried by pressing it on a filter paper to obtain the product Compound 133 as a white powder. Yield (20.0 mg, 20% yield).

Compound 133 $^1$H-NMR (400 MHz, DMSO): δ7.87-7.85 (d, 2H), 7.49 (s, 1H), 7.45 (s, 2H), 7.34-7.29 (m, 3H), 6.98 (s, 1H), 6.91-6.89 (d, 1H), 6.71 (s, 1H), 5.76-5.74 (d, 1H), 5.41 (s, 1H), 5.09 (s, 2H), 3.84 (s, 2H). ESI-MS m/z calcd for $C_{24}H_{18}Cl_2O_4$ 440.06, found 463.0 $[M+Na]^+$ 25. Compound 134

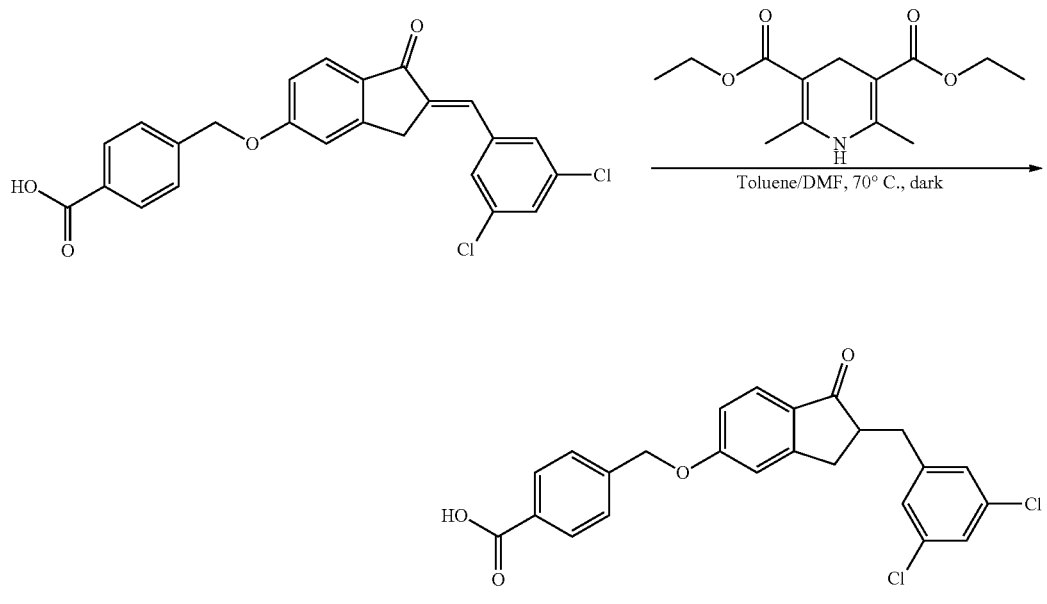

Scheme 25

To a mixture solution of the (E)-4-(((2-(3,5-dichlorobenzylidene)-1-oxo-2,3-dihydro-1H-inden-5-yl)oxy)methyl)benzoic acid (100.0 mg, 0.23 mmol), ethidine (86.5 mg, 0.34 mmol) and $SiO_2$ (250.0 mg) in the Toluene was added DMF (1 mL) and stirred at 70° C. for overnight. The reaction mixture was cooled to room temperature and filtered to remove the $SiO_2$. The filtrate was concentrated and purified with the thick TLC plate to obtain the product Compound 134. Yield (6.0 mg, 6% yield).

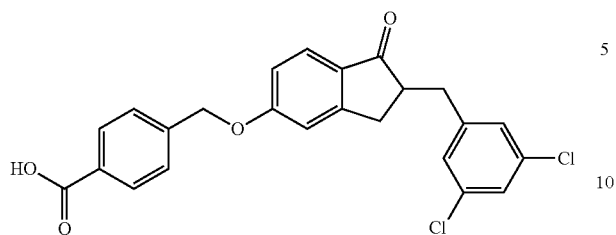

Compound 134 $^1$H-NMR (300 MHz, CD$_3$OD): δ8.04-8.01 (d, 2H), 7.67-7.64 (d, 1H), 7.56-7.53 (d, 2H), 7.34 (s, 1H), 7.25 (s, 2H), 7.13-7.04 (m, 2H), 5.26 (s, 2H), 3.31-3.19 (m, 2H), 3.15-3.13 (m, 1H), 2.83-2.77 (m, 2H). ESI-MS m/z calcd for C$_{24}$H$_{18}$Cl$_2$O$_4$ 440.06, found 441.0 [M+H]$^+$ B. Autotaxin Inhibitor Screening Assay As described above, the compounds in the present disclosure have the effect of inhibiting the activity of autotaxin, and can be used as autotaxin inhibitors. One method for inhibiting activity of autotaxin in environment is administering to the environment an effective amount of the compound of Formula (I). Please refer to the following experiment, the phosphodiesterase activity of autotaxin was measured using the p-nitrophenol that is a yellow product cleaved by autotaxin from the bis-(p-nitrophenyl) phosphate. Compound samples (10 μl) were incubated with autotaxin (10 μl) in a final volume of 200 μl assay buffer (5 mM CaCl$_2$, 50 mM Tris-HCl, pH 9.0) containing bis-(p-nitrophenyl) phosphate (BNPP) at a final concentration of 3 mM at 37° C. After 30 minutes, absorbance at 410 nm of the reacted solution was measured. The percent inhibition for each test article (TA) (compound) was determined using the following equation.

% Inhibition=(O.D.$_{vehicle}$−O.D.$_{TA}$)/O.D.$_{vehicle}$×100

The inhibition rate of the compounds on the activity of autotaxin enzyme are shown in Table 1

TABLE 1

| Compound Number | Inhibition | Compound Number | Inhibition | Compound Number | Inhibition |
|---|---|---|---|---|---|
| Compound 5 | A | Compound 45 | B | Compound 93 | B |
| Compound 6 | C | Compound 46 | B | Compound 96 | B |
| Compound 7 | B | Compound 47 | B | Compound 100 | C |
| Compound 8 | C | Compound 50 | B | Compound 99 | C |
| Compound 9 | C | Compound 52 | B | Compound 101 | C |
| Compound 10 | C | Compound 51 | A | Compound 102 | B |
| Compound 11 | B | Compound 53 | A | Compound 110 | B |
| Compound 12 | A | Compound 56 | C | Compound 117 | C |
| Compound 13 | A | Compound 57 | A | Compound 118 | C |
| Compound 14 | A | Compound 58 | A | Compound 119 | B |
| Compound 15 | B | Compound 59 | B | Compound 120 | A |
| Compound 16 | B | Compound 60 | B | Compound 121 | C |
| Compound 17 | A | Compound 61 | B | Compound 122 | C |
| Compound 18 | B | Compound 62 | A | Compound 123 | C |
| Compound 19 | A | Compound 68 | A | Compound 124 | C |
| Compound 20 | A | Compound 69 | C | Compound 125 | A |
| Compound 21 | A | Compound 70 | A | Compound 126 | C |
| Compound 26 | C | Compound 71 | B | Compound 127 | B |
| Compound 27 | C | Compound 72 | B | Compound 128 | B |
| Compound 28 | C | Compound 77 | B | Compound 129 | B |
| Compound 32 | C | Compound 81 | B | Compound 130 | A |
| Compound 33 | B | Compound 85 | A | Compound 131 | A |
| Compound 34 | B | Compound 88 | A | Compound 132 | C |
| Compound 38 | C | Compound 89 | B | Compound 133 | B |
| Compound 44 | C | Compound 92 | B | Compound 134 | A |

A: above 80% inhibition at 30 μM
B: 50%~80% inhibition at 30 μM
C: below 50% inhibition at 30 μM C. Pharmaceutical Formulation The compound of Formula (I) is present at a level of about 0.1% to 99% by weight, based on the total weight of the pharmaceutical composition. In some embodiments, the compound of Formula (I) is present at a level of at least 1% by weight, based on the total weight of the pharmaceutical composition. In certain embodiments, the compound of Formula (I) is present at a level of at least 5% by weight, based on the total weight of the pharmaceutical composition. In still other embodiments, the compound of Formula (I) is present at a level of at least 10% by weight, based on the total weight of the pharmaceutical composition. In still yet other embodiments, the compound of Formula (I) is present at a level of at least 25% by weight, based on the total weight of the pharmaceutical composition.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of the present disclosure from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:
1. A benzene fused ring derivative of Formula (I):

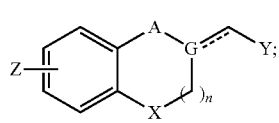

Formula (I)

------ is a single or double bond;
n is an integer of 0 or 1;
A is —$CH_2$—, —CH(OH)—, or —C(O)—;
G is C or N;
X is —$CH_2$—, or —C(O)—;
Y is alkyl, aryl, or heterocyclic alkyl optionally substituted with at least one substituent independently selected from a group consisting of: H, halogen, alkyl, alkyl substituted with at least one halogen, aryl, aryl substituted with at least one halogen, —$NR_{y1}R_{y2}$, —$OR_{y1}$, —$R_{y1}C(O)R_{y3}$, —$C(O)R_{y1}$, —$C(O)OR_{y2}$, —$C(O)OR_{y2}R_{y3}$, —$NR_{y1}C(O)R_{y2}$, —$NR_{y1}C(O)NR_{y2}R_{y3}$, —$NR_{y1}C(O)OR_{y2}R_{y3}$, —$NR_{y1}C(O)R_{y2}OR_{y3}$, —$C(O)NR_{y1}(R_{y2}R_{y3})$, —$C(O)NR_{y1}(R_{y2}OR_{y1})$, —$OR_{y2}R_{y3}$, and —$OR_{y2}OR_{y3}$, wherein each of $R_{y1}$ and $R_{y2}$ is independently selected from a group consisting of H, oxygen, alkyl, and aryl, and $R_{y}a$ is aryl optionally substituted with at least one halogen;
Z is —$NR_{z1}R_{z2}$, —$NR_{z1}R_{z3}$, —$OR_{z1}$, —$OR_{z1}R_{z3}$, —$C(O)R_{z1}R_{z3}$, —$C(O)OR_{z1}R_{z3}$, —$NR_{z1}C(O)R_{z2}R_{z3}$, —$NR_{z1}C(O)OR_{z2}R_{z3}$, —$C(O)NR_{z1}R_{z3}$, or $OR_{z2}OR_{z3}$, wherein each of $R_{z1}$ and $R_{z2}$ is independently selected from a group consisting of H, oxygen, alkyl and aryl, and $R_{z3}$ is aryl optionally substituted with at least one substituent independently selected from a group consisting of halogen, OH, —$R_{za}COOR_{zb}$, —$OR_{za}COOR_{zb}$, —$R_{za}SO_2R_{zb}$, —$R_{za}SO_2NR_{zb}R_{zc}R_{zd}$, —$R_{za}C(O)R_{zb}R_{zc}$, —$R_{za}C(O)NR_{zb}R_{zc}R_{zd}$, —$R_{za}C(O)NR_{zb}SO_2R_{zc}$, wherein $R_{za}$ is nil or alkyl, $R_{zb}$ is H or alkyl, each of $R_{zb}$ and $R_{zc}$ is independently selected from a group consisting of H, OH, alkyl, aryl, alkoxyl, or $NR_{zb}R_{zc}$ is a nitrogen-containing heterocyclic alkyl ring, $R_{zd}$ is nil or a sulfonyl alkyl group.

2. The benzene fused ring derivative as claimed in claim 1, wherein the alkyl is $C_1$-$C_{20}$ alkyl.

3. The benzene fused ring derivative as claimed in claim 1, wherein the aryl is $C_6$-$C_{10}$ aryl.

4. The benzene fused ring derivative as claimed in claim 1, having Formula (II):

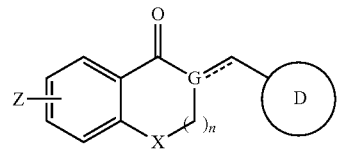

------ is a single or double bond;
n is an integer of 0 or 1;
G is C or N;
X is —$CH_2$—, or —C(O)—;

is aryl or heterocyclic ring optionally substituted with at least one substituent independently selected from a group consisting of:
H, halogen, alkyl, alkyl substituted with at least one halogen, aryl, aryl substituted with at least one halogen, —$NR_{d1}R_{d2}$, —$OR_{d1}$, —$R_{d1}C(O)R_{d3}$, —$C(O)R_{d1}$, —$C(O)OR_{d2}$, —$C(O)OR_{d2}R_{d3}$, —$NR_{d1}C(O)R_{d2}$, —$NR_{d1}C(O)NR_{d2}R_{d3}$, —$NR_{y1}C(O)OR_{d2}R_{d3}$, —$NR_{d1}C(O)R_{d2}OR_{d3}$, —$C(O)NR_{d1}(R_{d2}R_{d3})$, —$C(O)NR_{d1}(R_{d2}\ OR_{d1})$, —$OR_{d2}R_{d3}$, and —$OR_{d2}OR_{d3}$,
wherein each of $R_{d1}$ and $R_{d2}$ is independently selected from a group consisting of H, oxygen, alkyl, and aryl, and $R_{d3}$ is aryl optionally substituted with at least one halogen;
Z is —$NR_{z1}R_{z2}$, —$NR_{z1}R_{z3}$, —$OR_{z1}$, —$OR_{z1}R_{z3}$, —$C(O)R_{z1}R_{z3}$, —$C(O)OR_{z1}R_{z3}$, —$NR_{z1}C(O)R_{z2}R_{z3}$, —$NR_{z1}C(O)OR_{z2}R_{z3}$, —$C(O)NR_{z1}R_{z3}$, or $OR_{z2}OR_{z3}$, wherein each of $R_{z1}$ and $R_{z2}$ is independently selected from a group consisting of H, oxygen, alkyl and aryl, and $R_{z3}$ is aryl optionally substituted with at least one substituent independently selected from a group consisting of halogen, OH, —$R_{za}COOR_{zb}$, —$OR_{za}COOR_{zb}$, —$R_{za}SO_2R_{zb}$, —$R_{za}SO_2NR_{zb}R_{zc}R_{zd}$, —$R_{za}C(O)R_{zb}R_{zc}$, —$R_{za}C(O)NR_{zb}R_{zc}R_{zd}$, —$R_{za}C(O)NR_{zb}SO_2R_{zc}$, wherein $R_{za}$ is nil or alkyl, $R_{zb}$ is H or alkyl, each of $R_{zb}$ and $R_{zc}$ is independently selected from a group consisting of H, OH, alkyl, aryl, alkoxyl, or $NR_{zb}R_{zc}$ is a nitrogen-containing heterocyclic alkyl ring, $R_{zd}$ is nil or a sulfonyl alkyl group.

5. The benzene fused ring derivative as claimed in claim 1, wherein the benzene fused ring derivative is selected from the compounds delineated in Table A or its geometric isomers, enantiomers, diastereomers, racemates, pharmaceutically acceptable salts, prodrugs and solvates thereof:

TABLE A

| Compound Number | Structure |
|---|---|
| 5 | *structure 5* |
| 6 | *structure 6* |
| 7 | *structure 7* |
| 8 | *structure 8* |
| 9 | *structure 9* |

TABLE A-continued
| Compound Number | Structure |
|---|---|
| 10 | 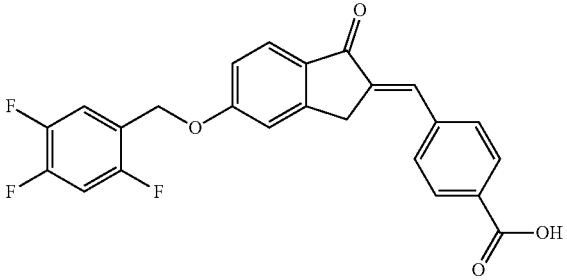 |
| 11 | 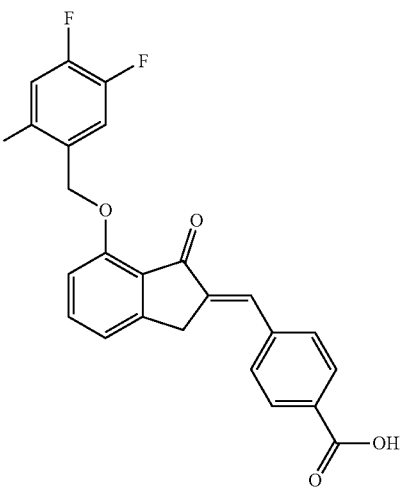 |
| 12 | 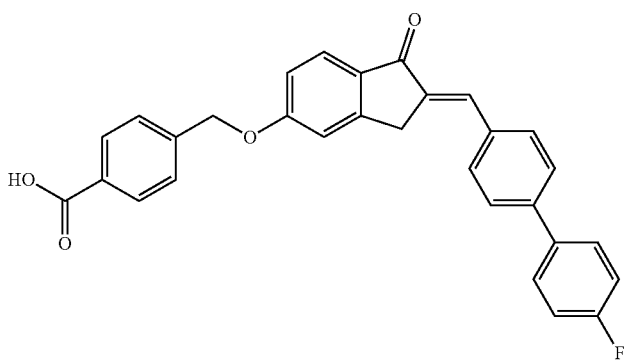 |
| 13 | 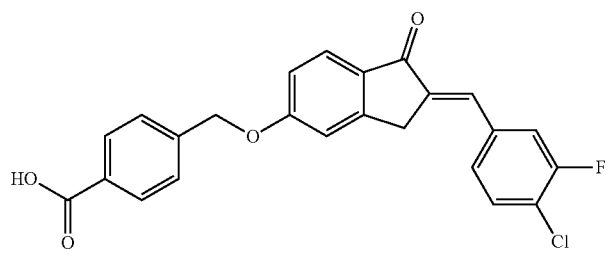 |

TABLE A-continued
| Compound Number | Structure |
|---|---|
| 14 | 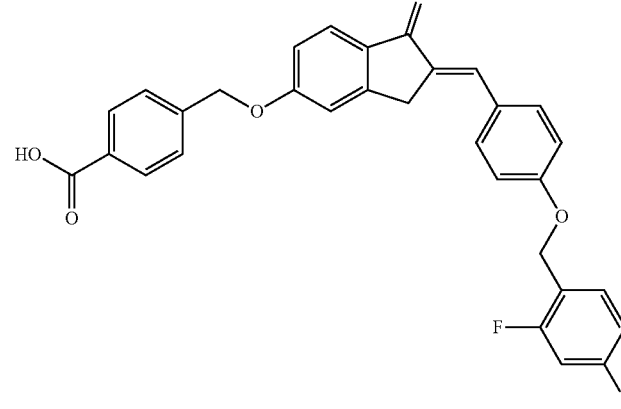 |
| 15 | 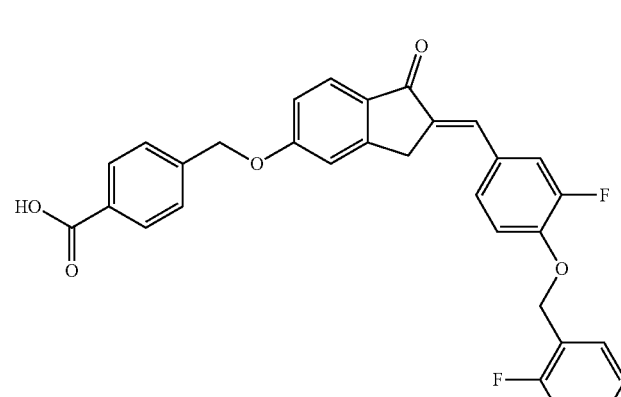 |
| 16 | 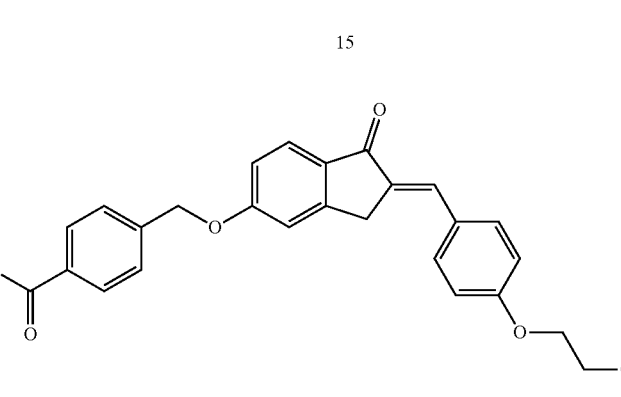 |

TABLE A-continued

| Compound Number | Structure |
|---|---|
| 17 | (4-((1-oxo-2-(3-(3,5-dichlorophenyl)propylidene)-2,3-dihydro-1H-inden-5-yl)oxy)methyl)benzoic acid |
| 18 | 4-(((2-(3,4,5-trifluorobenzylidene)-1-oxo-2,3-dihydro-1H-inden-5-yl)oxy)methyl)benzoic acid |
| 19 | 4-(((2-(2,4-dichlorobenzylidene)-1-oxo-2,3-dihydro-1H-inden-5-yl)oxy)methyl)benzoic acid |
| 20 | 4-(((2-(3,5-dichlorobenzylidene)-1-oxo-2,3-dihydro-1H-inden-5-yl)oxy)methyl)benzoic acid |
| 21 | 4-(((2-(2,4,5-trifluorobenzylidene)-1-oxo-2,3-dihydro-1H-inden-5-yl)oxy)methyl)benzoic acid |

TABLE A-continued
| Compound Number | Structure |
|---|---|
| 26 | 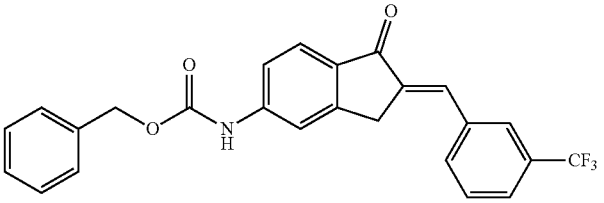 |
| 27 | 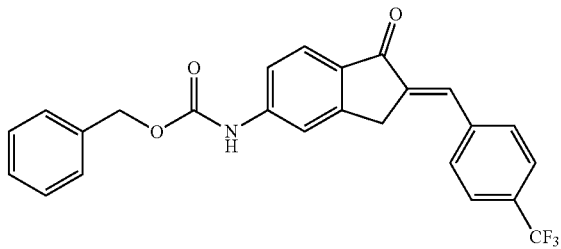 |
| 28 | 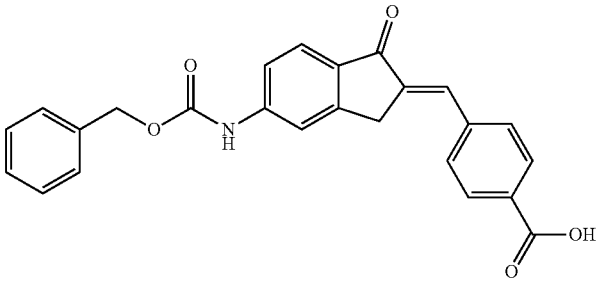 |
| 32 | 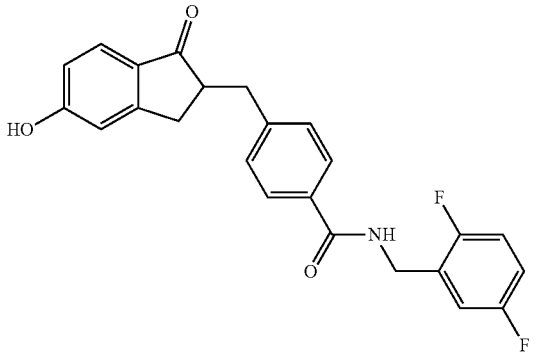 |

TABLE A-continued
| Compound Number | Structure |
| --- | --- |
| 33 | 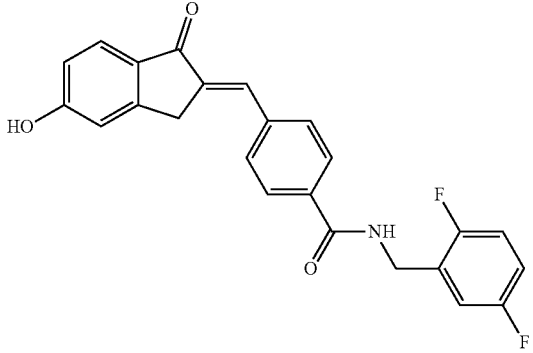 |
| 34 | 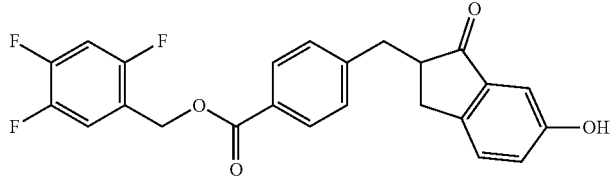 |
| 38 | 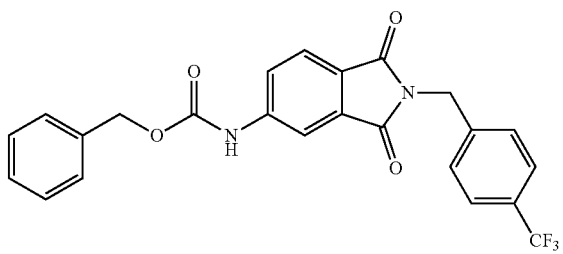 |
| 44 | 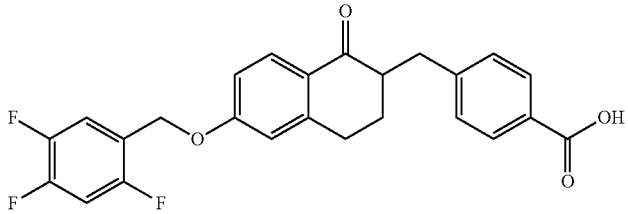 |
| 45 | 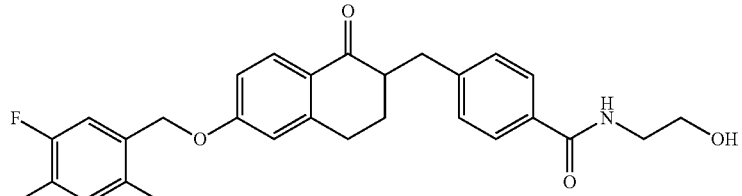 |

TABLE A-continued
| Compound Number | Structure |
|---|---|
| 46 | 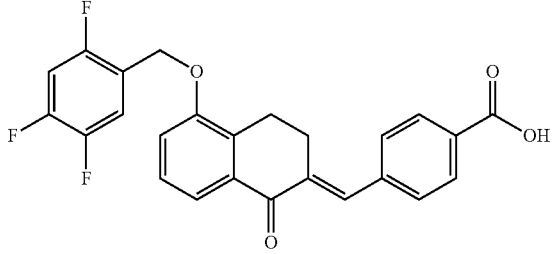 46 |
| 47 | 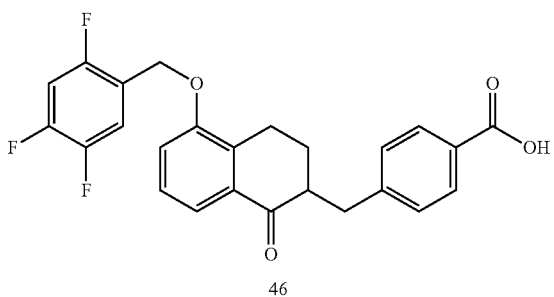 [SMILES: O=C(O)c1ccc(CC2CCc3c(OCc4cc(F)c(F)cc4F)cccc3C2=O)cc1] 46 |
| 50 | 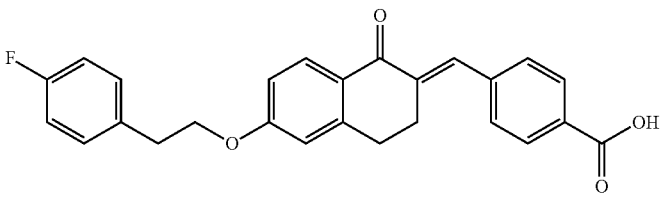 50 |
| 51 | 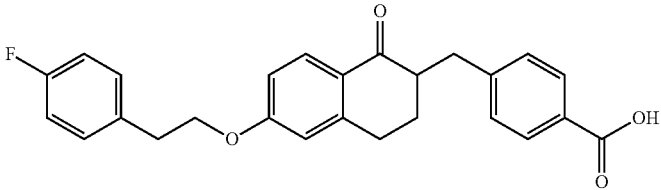 51 |
| 52 | 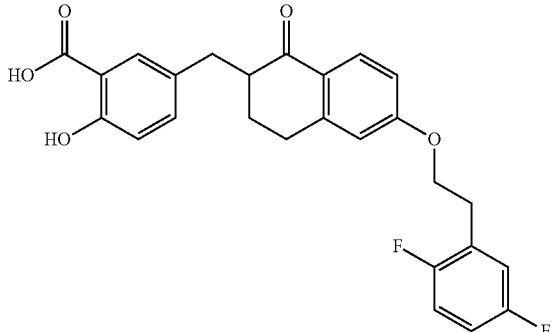 52 |

TABLE A-continued
| Compound Number | Structure |
|---|---|
| 53 | 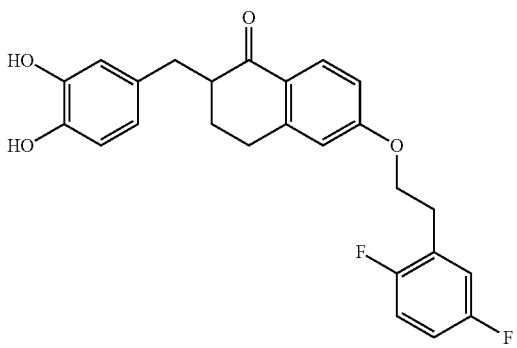<br>53 |
| 56 | 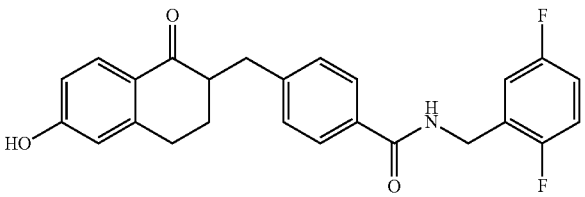<br>56 |
| 57 | 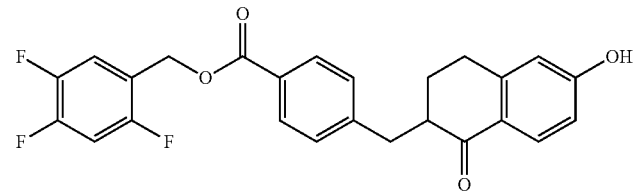<br>57 |
| 58 | 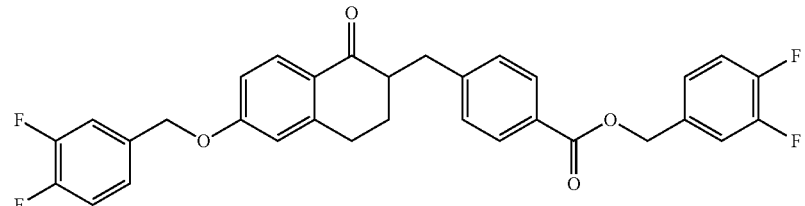<br>58 |
| 59 | 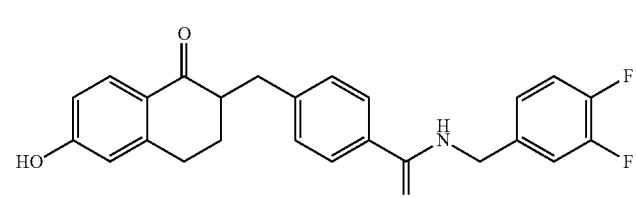<br>59 |

TABLE A-continued
| Compound Number | Structure |
|---|---|
| 60 | 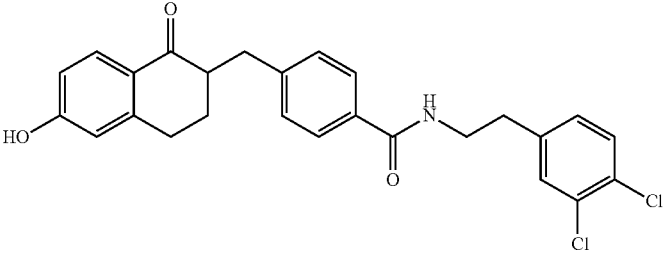<br>60 |
| 61 | 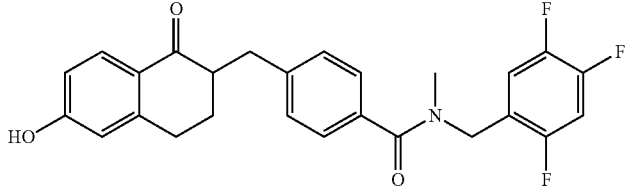<br>61 |
| 62 | 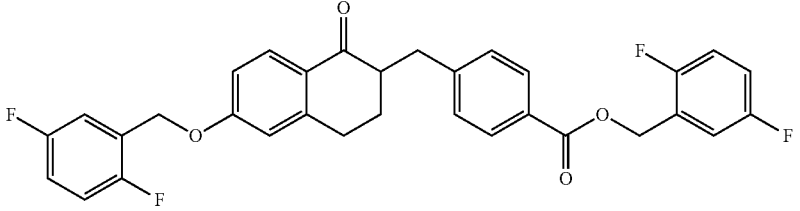<br>62 |
| 68 | 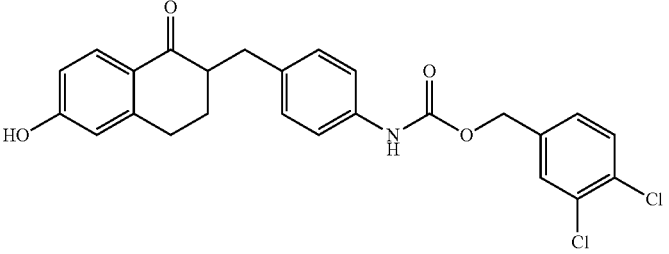<br>68 |
| 69 | 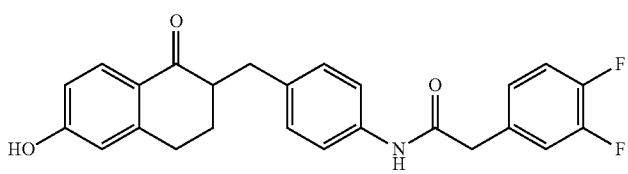<br>69 |

TABLE A-continued
| Compound Number | Structure |
|---|---|
| 70 | 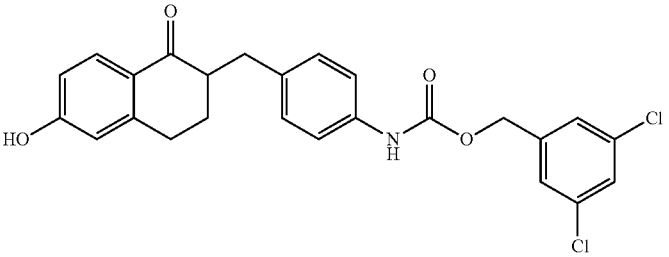 |
| 71 | 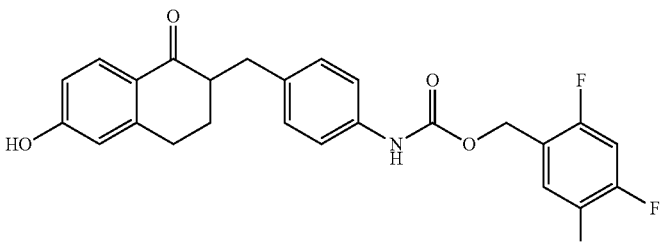 |
| 72 | 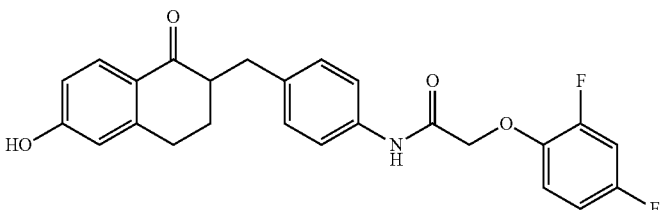 |
| 77 | 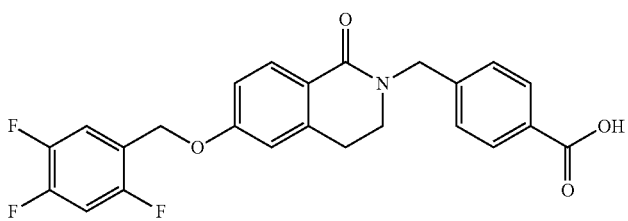 |
| 81 | 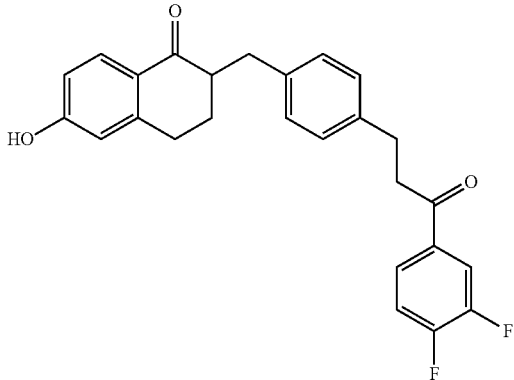 |

TABLE A-continued
| Compound Number | Structure |
|---|---|
| 85 | 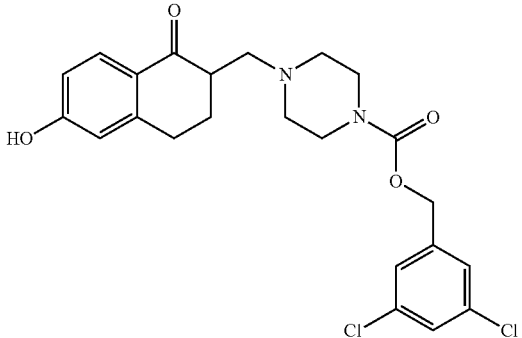 85 |
| 88 | 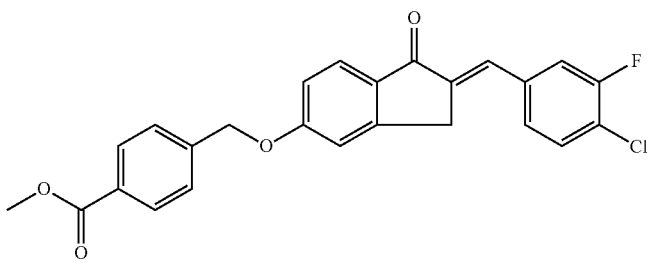 88 |
| 92 | 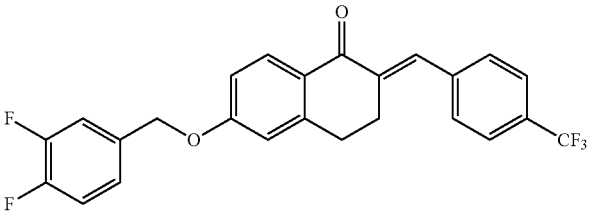 92 |
| 93 | 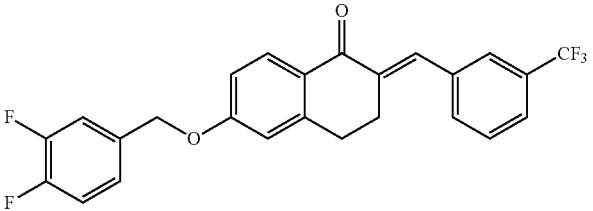 93 |
| 96 | 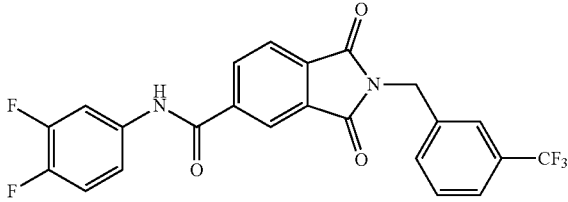 96 |

TABLE A-continued
| Compound Number | Structure |
|---|---|
| 99 | 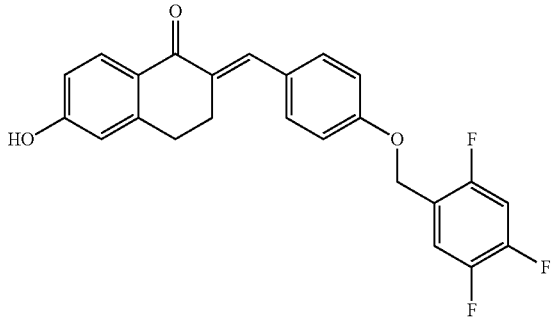<br>99 |
| 100 | 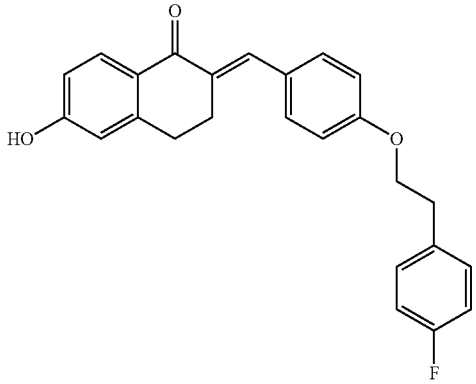<br>100 |
| 101 | 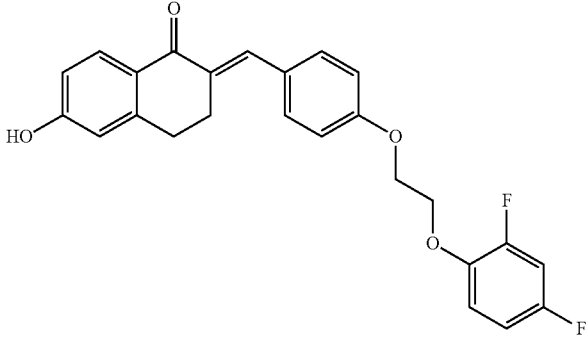<br>101 |
| 102 | 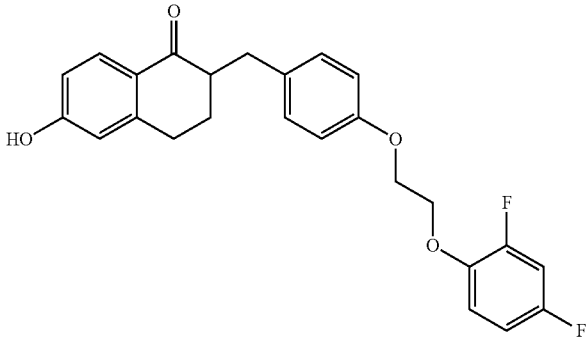<br>102 |

TABLE A-continued
| Compound Number | Structure |
|---|---|
| 110 | 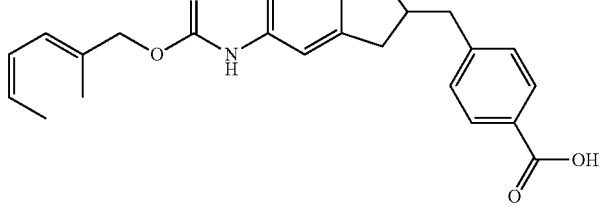<br>110 |
| 117 | 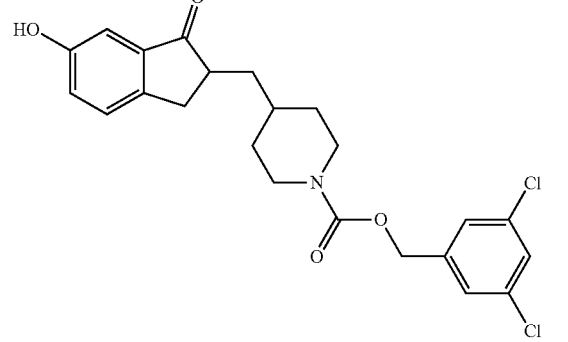<br>117 |
| 118 | 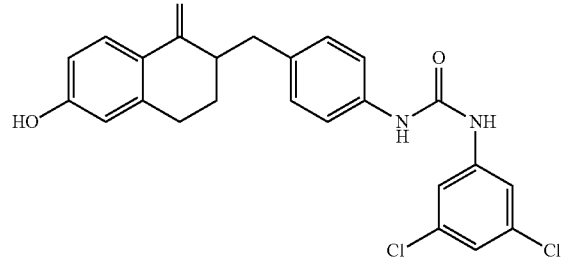<br>118 |
| 119 | 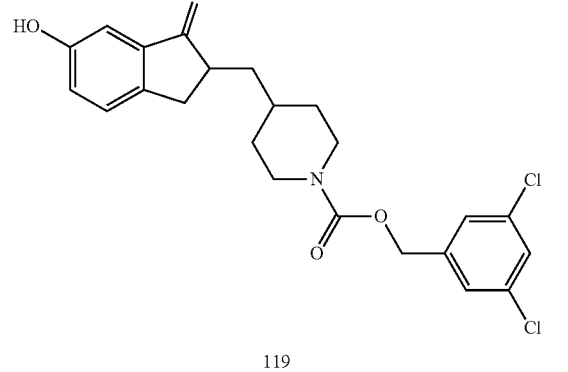<br>119 |

TABLE A-continued
| Compound Number | Structure |
|---|---|
| 120 | 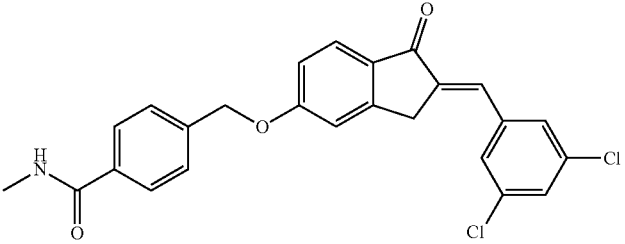<br>120 |
| 121 | 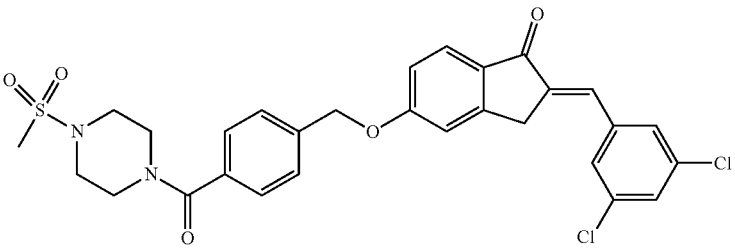<br>121 |
| 122 | 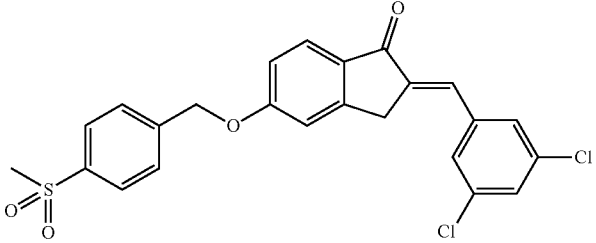<br>122 |
| 123 | 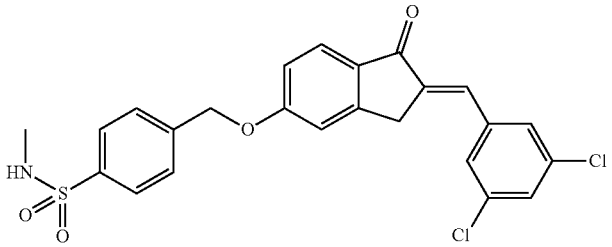<br>123 |
| 124 | 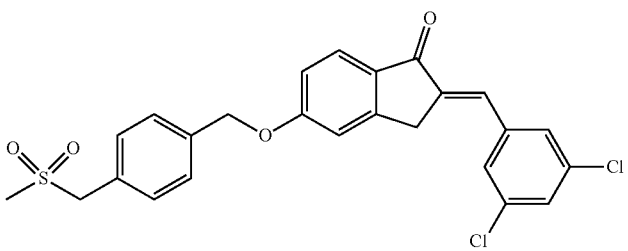<br>124 |

TABLE A-continued
| Compound Number | Structure |
|---|---|
| 125 | 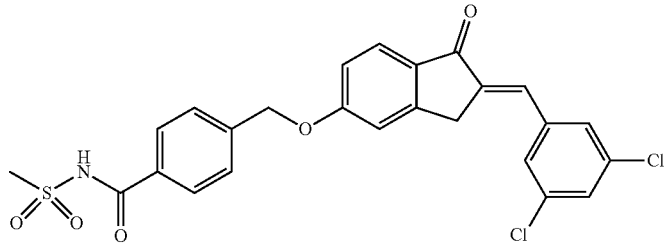<br>125 |
| 126 | 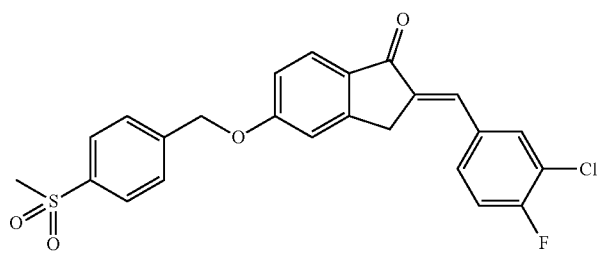<br>126 |
| 127 | 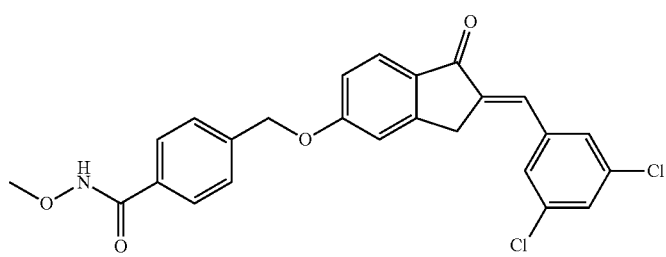<br>127 |
| 128 | 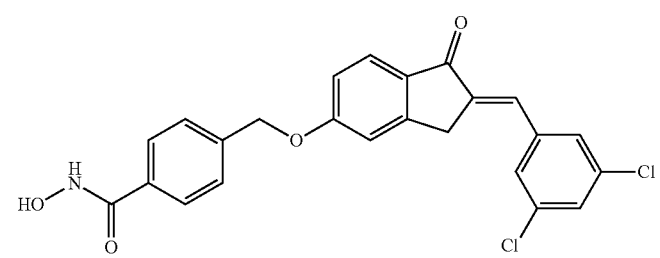<br>128 |
| 129 | 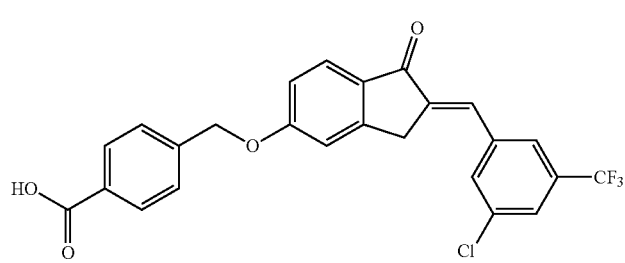<br>129 |

TABLE A-continued

| Compound Number | Structure |
|---|---|
| 130 | 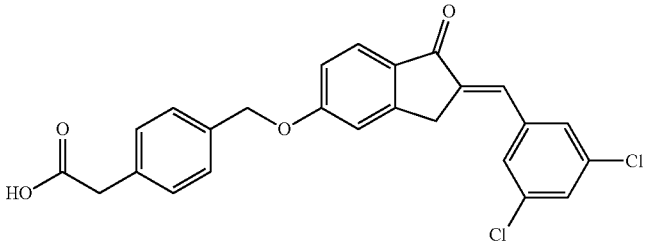<br>130 |
| 131 | 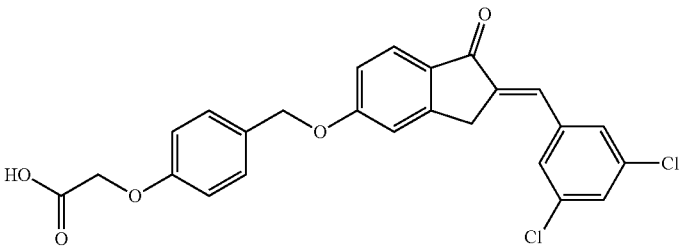<br>131 |
| 132 | 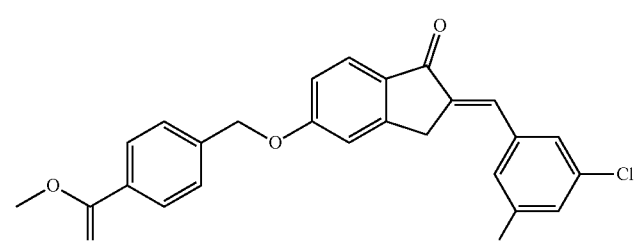<br>132 |
| 133 | 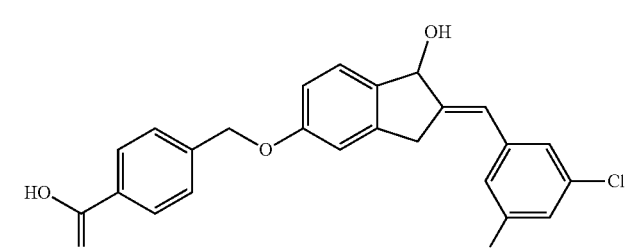<br>133 |
| 134 | 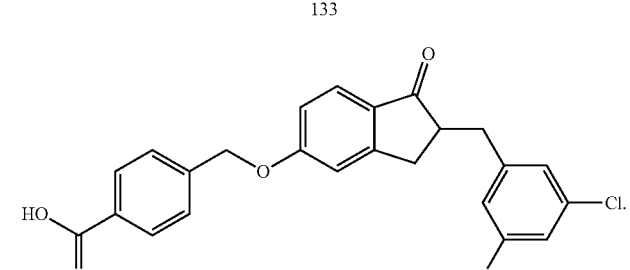<br>134 |

6. A pharmaceutical composition, comprising:
a therapeutically effective amount of the benzene fused ring derivative of claim 1; and
a pharmaceutically acceptable carrier.

7. The pharmaceutical composition of claim 6; wherein the pharmaceutically acceptable carrier is selected from the group consisting of inert diluents, dispersing and/or granulating agents, surface active agents and/or emulsifiers, disintegrating agents, binding agents, preservatives, buffering agents, lubricating agents, and oils.

8. A method for inhibiting activity of autotaxin in environment, comprising:
contacting the environment with an effective amount of the benzene fused ring derivative of claim 1.

9. The method of claim 8, wherein the environment is a cell.

10. A method for inhibiting activity of autotaxin in environment, comprising:
contacting the environment with an effective amount of the pharmaceutical composition of claim 6.

11. The method of claim 10, wherein the environment is a cell.

12. The method of claim 10, wherein the pharmaceutical composition comprises a pharmaceutically acceptable carrier selected from the group consisting of inert diluents, dispersing and/or granulating agents, surface active agents and/or emulsifiers, disintegrating agents, binding agents, preservatives, buffering agents, lubricating agents, and oils.

* * * * *